US 9,109,011 B2

(12) United States Patent
Banchereau et al.

(10) Patent No.: US 9,109,011 B2
(45) Date of Patent: Aug. 18, 2015

(54) DENDRITIC CELL-SPECIFIC ANTIBODY CONJUGATE COMPRISING ANTI-CD40 MONOCLONAL ANTIBODIES CONJUGATED TO HIV-1 GAG/NEF

(75) Inventors: Jacques F. Banchereau, Montclair, NJ (US); Gerard Zurawski, Midlothian, TX (US); Anne-Laure Flamar, Dallas, TX (US); Amanda Cobb, Forth Worth, TX (US); Holly Mead, Plano, TX (US); Monica Montes, Dallas, TX (US); Sandra Zurawski, Midlothian, TX (US); SangKon Oh, Baltimore, MD (US)

(73) Assignee: Baylor Research Institute, Dallas, TX (US)

( * ) Notice: Subject to any disclaimer, the term of this patent is extended or adjusted under 35 U.S.C. 154(b) by 614 days.

(21) Appl. No.: 12/504,463

(22) Filed: Jul. 16, 2009

(65) Prior Publication Data

US 2010/0135994 A1 Jun. 3, 2010

Related U.S. Application Data

(60) Provisional application No. 61/081,234, filed on Jul. 16, 2008.

(51) Int. Cl.
*C07K 14/005* (2006.01)
*C07K 14/15* (2006.01)
*C07K 16/28* (2006.01)
*A61K 47/48* (2006.01)
*A61K 39/21* (2006.01)

(52) U.S. Cl.
CPC .............. *C07K 14/005* (2013.01); *A61K 39/21* (2013.01); *A61K 47/4833* (2013.01); *A61K 47/48538* (2013.01); *A61K 47/48561* (2013.01); *C07K 14/15* (2013.01); *C07K 16/2878* (2013.01); *C07K 2319/01* (2013.01); *C07K 2319/035* (2013.01); *C07K 2319/30* (2013.01); *C07K 2319/33* (2013.01); *C12N 2740/16011* (2013.01); *C12N 2740/16222* (2013.01); *C12N 2740/16234* (2013.01); *C12N 2740/16322* (2013.01); *C12N 2740/16334* (2013.01)

(58) Field of Classification Search
CPC .............. C07K 14/15; C07K 16/2878; C07K 2319/01; A61K 47/48561; C12N 2740/16011
See application file for complete search history.

(56) References Cited

U.S. PATENT DOCUMENTS

| | | | |
|---|---|---|---|
| 3,791,932 | A | 2/1974 | Schuurs et al. |
| 3,949,064 | A | 4/1976 | Bornstein et al. |
| 4,174,384 | A | 11/1979 | Ullman et al. |
| 4,554,101 | A | 11/1985 | Hopp |
| 6,541,011 | B2 | 4/2003 | Punnonen et al. |
| 2005/0013810 | A1 | 1/2005 | Waller et al. |
| 2005/0037001 | A1 | 2/2005 | Germeraad et al. |
| 2005/0106700 | A1 | 5/2005 | Nomura ........................ 435/226 |
| 2006/0193855 | A1 | 8/2006 | Bot et al. |
| 2007/0243203 | A1* | 10/2007 | Abrecht et al. ............ 424/188.1 |
| 2009/0004194 | A1 | 1/2009 | Kedl ........................... 424/139.1 |

FOREIGN PATENT DOCUMENTS

| | | |
|---|---|---|
| EP | 0324625 | 7/1989 |
| JP | 2000-157282 | 6/2000 |
| JP | 2004-236504 | 8/2004 |
| JP | 2005-143444 | 9/2005 |
| WO | WO 99/57157 | 11/1999 |
| WO | WO 00/00156 | 1/2000 |
| WO | WO 01/70253 | 9/2001 |
| WO | WO 03/011334 | 2/2003 |
| WO | WO 03/033695 | 4/2003 |
| WO | WO 2006/013106 | 2/2006 |
| WO | WO 2006/020480 | 2/2006 |
| WO | WO 2007/019949 | 2/2007 |
| WO | WO 2010/009346 | 1/2010 |

OTHER PUBLICATIONS

Gallo, R. C., 2005, The end or the beginning of the drive to an HIV-preventive vaccine: a view from over 20 years, The Lancet, 366:1894-1898.*
Connick, E., et al., 2007, CTL fail to accumulate at sites of HIV-1 replication in lymphoid tissue, J. Immunol. 178:6975-6983.*
Levine, A. J., 2008, Why do we not yet have a human immunodeficiency virus vaccine? J. Virol. 82(24):11998-12000.*
Walker, B. D., and D. R. Burton, 2008, Toward an AIDS vaccine, Science 320:760-764.*
Bozzacco, L., et al., Jan. 2007, DEC-205 rececptor on dendritic cells mediates presentation of HIV gag protein to CD8+ T cells in a spectrum of human MHC haplotypes, PNAS 104(4):1289-1294.*
Schjetne, K. W., et al., 2007, Delivery of antigen to CD40 induces protective immune responses against tumors, J. Immunol. 178:4169-4176.*
Chen, C., et al., Sep. 1992, Generation and analysis of random point mutations in an antibody CDR2 sequence: many mutated antibodies lose their ability to bind antigen, J. Exp. Med. 176:855-866.*
Xiang, J., et al., 1995, Framework residues 71 and 93 of the chimeric B72.3 antibody are major determinants of the conformation of heavy-chain hypervariable loops, J. Mol. Biol. 253:385-390.*

(Continued)

*Primary Examiner* — Jeffrey Parkin
(74) *Attorney, Agent, or Firm* — Norton Rose Fulbright US LLP

(57) ABSTRACT

The present invention includes compositions and methods for making and using a vaccine that includes a DC-specific antibody or fragment thereof to which an engineered Gag antigen is attached to form an antibody-antigen complex, wherein the Gag antigen is less susceptible to proteolytic degradation by eliminating one or more proteolytic sites or a DC-specific antibody or fragment thereof to which an engineered Nef antigen is attached to form an antibody-antigen complex, wherein the Nef antigen comprises one or more codon usage optimization that increase antibody-antigen complex secretion, or both, wherein the vaccine is able to elicit an HIV-specific T cell immune response to Gag p17, Gag p24, Nef and/or Cyclin D1.

5 Claims, 26 Drawing Sheets

(56) References Cited

OTHER PUBLICATIONS

Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*

Boscardin, et al., "Antigen targeting to dendritic cells elicits long-lived T cell help for antibody responses," JEM (2006) vol. 203, No. 3, 599-606.

International Search Report and Written Opinion for PCT/US2009/050903 dated Mar. 3, 2010.

Dengjel, J., et al., "Identification of a naturally processed cyclin D1 T-helper epitope by a novel combination of HLA class II targeting and differential mass spectrometry," Eur J Immunol (2004), 34:3644-3651.

Kavanagh, D. G., et al., "Expansion of HIV-specific CD4+ and CD8+ T cells by dendritic cells transfected with mRNA encoding cytoplasm- or lysosome-targeted Nef," Blood (2006), 107:1963-1969.

Nchinda, G., et al., "The efficacy of DNA vaccination is enhanced in mice by targeting the encoded protein to dendritic cells," J Clin Invest (2008), 118:1427-1436.

Trumpfheller, C., et al., "Intensified and protective CD4+ T cell immunity in mice with anti-dendritic cell HIV gag fusion antibody vaccine," J Exp Med (2006), 203:607-617.

Cote, H.C.F. el al. "Human Immunodeficiency Virus Type 1 Protease Cleavage Site Mutations Associated with Protease Inhibitor Cross-Resistance Selected by Indinavir, Ritonavir, and/or Saquinavir", Journal of Virology, vol. 75, No. 2, Jan. 15, 2001, pp. 589-594.

Leung, Tommy W.C. el al. "Molecular Epidemiology Demonstrated Three Emerging Clusters of Human Immunodeficiency Virus Type 1 Subtype B Infection in Hong Kong", AIDS Research and Human Retroviruses, vol. 24, No. 7, Jul. 1, 2008, pp. 903-910.

Keler, T., et al., "Antibody-Targeted Vaccines," Oncogene, (2007), 26:3758-3767.

Supplemental European Search Report for EP 09798772.1, dated Feb. 16, 2012, 14 pages.

Snider, Denis P., et al., "Targeted Antigen Presentation Using Crosslinked Antibody Heteroaggregates," The Journal of Immunology, Sep. 1, 1987, vol. 138, No. 5, pp. 1609-1616.

Tacken, Paul J., et al., "Dendritic-Cell Immunotherapy: From ex vivo Loading to in vivo Targeting," Nature, Oct. 2007, vol. 7, pp. 790-802.

* cited by examiner

1. DCIR.gag p24 [77 kDa] C241
2. LOX-1.gag p24 [77 kDa]
3. LOX-1.flex HA1-1 [87 kDa]
4. mIgG [50 kDa]

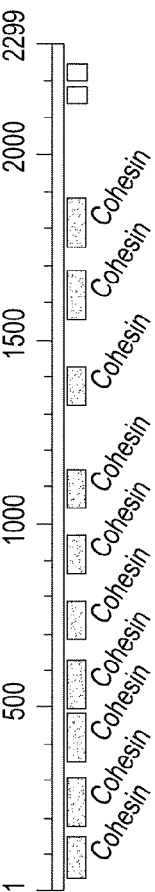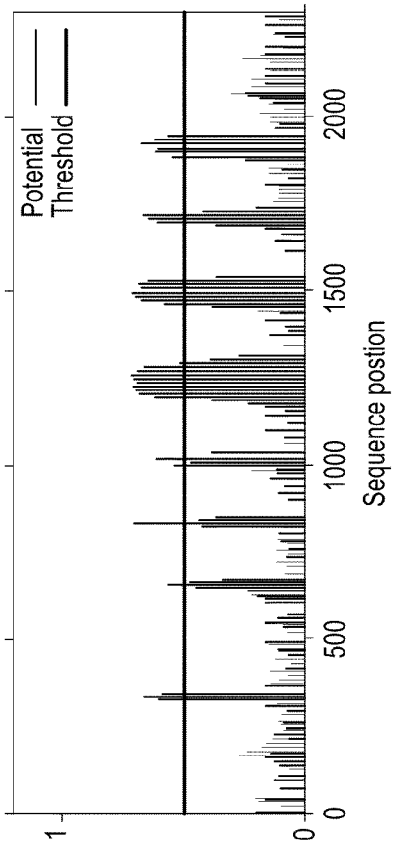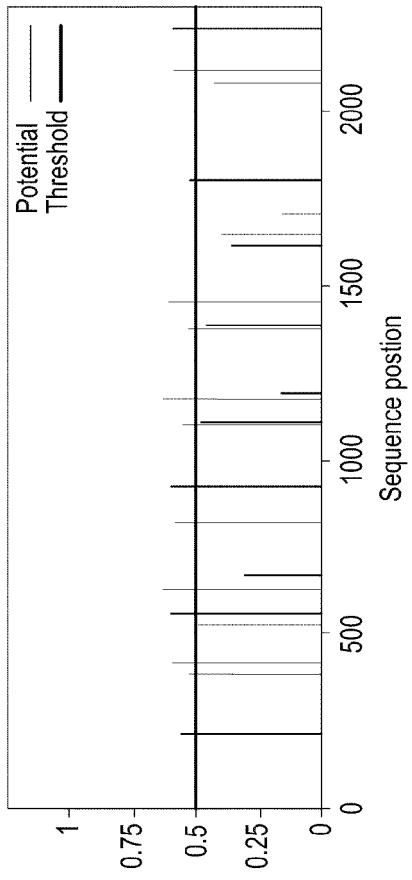
FIG. 4A
FIG. 4B
FIG. 4C

SEQUENCE LISTING

<160> NUMBER OF SEQ ID NOS: 32

<210> SEQ ID NO 1
<211> LENGTH: 701
<212> TYPE: PRT
<213> ORGANISM: Artificial Sequence
<220> FEATURE:
<223> OTHER INFORMATION: Synthesized Sequence

<400> SEQUENCE: 1

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
        130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
                180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Glu
225                 230                 235                 240
```

-continued

```
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
Gln Glu Asp Pro Glu Val Gln Phe Asn Trp Tyr Val Asp Gly Val Glu
                275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Gln Glu Glu Met Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
                420                 425                 430
Met His Glu Ala Leu His Asn His Tyr Thr Gln Lys Ser Leu Ser Leu
                435                 440                 445
Ser Leu Gly Lys Ala Ser Asp Met Ala Lys Lys Glu Thr Val Trp Arg
                450                 455                 460
Leu Glu Glu Phe Gly Arg Pro Ile Val Gln Asn Ile Gln Gly Gln Met
465                 470                 475                 480
Val His Gln Ala Ile Ser Pro Arg Thr Leu Asn Ala Trp Val Lys Val
                485                 490                 495
Val Glu Glu Lys Ala Phe Ser Pro Glu Val Ile Pro Met Phe Ser Ala
                500                 505                 510
Leu Ser Glu Gly Ala Thr Pro Gln Asp Leu Asn Thr Met Leu Asn Thr
                515                 520                 525
Val Gly Gly His Gln Ala Ala Met Gln Met Leu Lys Glu Thr Ile Asn
                530                 535                 540
Glu Glu Ala Ala Glu Trp Asp Arg Val His Pro Val His Ala Gly Pro
545                 550                 555                 560
Ile Ala Pro Gly Gln Met Arg Glu Pro Arg Gly Ser Asp Ile Ala Gly
                565                 570                 575
Thr Thr Ser Thr Leu Gln Glu Gln Ile Gly Trp Met Thr Asn Asn Pro
                580                 585                 590
Pro Ile Pro Val Gly Glu Ile Tyr Lys Arg Trp Ile Ile Leu Gly Leu
                595                 600                 605
Asn Lys Ile Val Arg Met Tyr Ser Pro Thr Ser Ile Leu Asp Ile Arg
                610                 615                 620
Gln Gly Pro Lys Glu Pro Phe Arg Asp Tyr Val Asp Arg Phe Tyr Lys
625                 630                 635                 640
Thr Leu Arg Ala Glu Gln Ala Ser Gln Glu Val Lys Asn Trp Met Thr
                645                 650                 655
```

```
Glu Thr Leu Leu Val Gln Asn Ala Asn Pro Asp Cys Lys Thr Ile Leu
            660                 665                 670

Lys Ala Leu Gly Pro Ala Ala Thr Leu Glu Glu Met Met Thr Ala Cys
        675                 680                 685

Gln Gly Val Gly Gly Pro Gly His Lys Ala Arg Val Leu
    690                 695                 700

<210> SEQ ID NO 2
<211> LENGTH: 783
<212> TYPE: PRT
<213> ORGANISM: Artificial Sequence
<220> FEATURE:
<223> OTHER INFORMATION: Synthesized Sequence

<400> SEQUENCE: 2

Glu Ile Gln Leu Gln Gln Thr Gly Pro Glu Leu Val Lys Pro Gly Ala
1               5                   10                  15

Ser Val Lys Ile Ser Cys Lys Ala Ser Gly Tyr Pro Phe Thr Asp Tyr
            20                  25                  30

Ile Met Val Trp Val Lys Gln Ser His Gly Lys Ser Leu Glu Trp Ile
        35                  40                  45

Gly Asn Ile Ser Pro Tyr Tyr Gly Thr Thr Asn Tyr Asn Leu Lys Phe
    50                  55                  60

Lys Gly Lys Ala Thr Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Pro Asn Trp Asp Gly Ala Trp Phe Ala His Trp Gly Gln
            100                 105                 110

Gly Ala Leu Val Thr Val Ser Ala Ala Lys Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

-continued

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Ala
        435                 440                 445

Ser Asp Thr Thr Glu Pro Ala Thr Pro Thr Thr Pro Val Thr Thr Asp
    450                 455                 460

Thr Ile Cys Ile Gly Tyr His Ala Asn Asn Ser Thr Asp Thr Val Asp
465                 470                 475                 480

Thr Val Leu Glu Lys Asn Val Thr Val Thr His Ser Val Asn Leu Leu
                485                 490                 495

Glu Asp Ser His Asn Gly Lys Leu Cys Arg Leu Lys Gly Ile Ala Pro
                500                 505                 510

Leu Gln Leu Gly Lys Cys Asn Ile Ala Gly Trp Leu Leu Gly Asn Pro
            515                 520                 525

Glu Cys Asp Pro Leu Leu Pro Val Arg Ser Trp Ser Tyr Ile Val Glu
        530                 535                 540

Thr Pro Asn Ser Glu Asn Gly Ile Cys Tyr Pro Gly Asp Phe Ile Asp
545                 550                 555                 560

Tyr Glu Glu Leu Arg Glu Gln Leu Ser Ser Val Ser Ser Phe Glu Arg
                565                 570                 575

Phe Glu Ile Phe Pro Lys Glu Ser Ser Trp Pro Asn His Asn Thr Asn
            580                 585                 590

Gly Val Thr Ala Ala Cys Ser His Glu Gly Lys Ser Ser Phe Tyr Arg
        595                 600                 605

Asn Leu Leu Trp Leu Thr Glu Lys Glu Gly Ser Tyr Pro Lys Leu Lys
    610                 615                 620

Asn Ser Tyr Val Asn Lys Lys Gly Lys Glu Val Leu Val Leu Trp Gly
625                 630                 635                 640

Ile His His Pro Pro Asn Ser Lys Glu Gln Gln Asn Leu Tyr Gln Asn
                645                 650                 655

Glu Asn Ala Tyr Val Ser Val Val Thr Ser Asn Tyr Asn Arg Arg Phe
            660                 665                 670

Thr Pro Glu Ile Ala Glu Arg Pro Lys Val Arg Asp Gln Ala Gly Arg
        675                 680                 685

Met Asn Tyr Tyr Trp Thr Leu Leu Lys Pro Gly Asp Thr Ile Ile Phe
    690                 695                 700

Glu Ala Asn Gly Asn Leu Ile Ala Pro Met Tyr Ala Phe Ala Leu Ser
705                 710                 715                 720

Arg Gly Phe Gly Ser Gly Ile Ile Thr Ser Asn Ala Ser Met His Glu
                725                 730                 735

Cys Asn Thr Lys Cys Gln Thr Pro Leu Gly Ala Ile Asn Ser Ser Leu

```
                  740                 745                 750
Pro Tyr Gln Asn Ile His Pro Val Thr Ile Gly Glu Cys Leu Lys Tyr
            755                 760                 765

Val Arg Ser Ala Lys Leu Arg Met Val His His His His His
770                 775                 780
```

<210> SEQ ID NO 3
<211> LENGTH: 734
<212> TYPE: PRT
<213> ORGANISM: Artificial Sequence
<220> FEATURE:
<223> OTHER INFORMATION: Synthesized Sequence

<400> SEQUENCE: 3

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Ala Thr Tyr Tyr
                85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
```

```
            325                 330                 335
Ile Glu Lys Thr Ile Ser Lys Ala Lys Gly Gln Pro Arg Glu Pro Gln
            340                 345                 350

Val Tyr Thr Leu Pro Pro Ser Gln Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                    405                 410                 415

Val Asp Lys Ser Arg Trp Gln Glu Gly Asn Val Phe Ser Cys Ser Val
                    420                 425                 430

Met His Glu Ala Leu His Asn His Tyr Thr Gln Lys Ser Leu Ser Leu
                    435                 440                 445

Ser Leu Gly Lys Ala Ser Gln Thr Pro Thr Asn Thr Ile Ser Val Thr
            450                 455                 460

Pro Thr Asn Asn Ser Thr Pro Thr Asn Asn Ser Asn Pro Lys Pro Asn
465                 470                 475                 480

Pro Ala Ser Val Asp Ser Glu Phe Ala Gln Gln Ala Ala Asp Thr
                    485                 490                 495

Gly His Ser Asn Gln Val Ser Gln Asn Tyr Pro Ile Val Gln Asn Ile
                    500                 505                 510

Gln Gly Gln Met Val His Gln Ala Ile Ser Pro Arg Thr Leu Asn Ala
            515                 520                 525

Trp Val Lys Val Val Glu Glu Lys Ala Phe Ser Pro Glu Val Ile Pro
530                 535                 540

Met Phe Ser Ala Leu Ser Glu Gly Ala Thr Pro Gln Asp Leu Asn Thr
545                 550                 555                 560

Met Leu Asn Thr Val Gly Gly His Gln Ala Ala Met Gln Met Leu Lys
                    565                 570                 575

Glu Thr Ile Asn Glu Glu Ala Ala Glu Trp Asp Arg Val His Pro Val
                    580                 585                 590

His Ala Gly Pro Ile Ala Pro Gly Gln Met Arg Glu Pro Arg Gly Ser
            595                 600                 605

Asp Ile Ala Gly Thr Thr Ser Thr Leu Gln Glu Gln Ile Gly Trp Met
610                 615                 620

Thr His Asn Pro Pro Ile Pro Val Gly Glu Ile Tyr Lys Arg Trp Ile
625                 630                 635                 640

Ile Leu Gly Leu Asn Lys Ile Val Arg Met Tyr Ser Pro Thr Ser Ile
                    645                 650                 655

Leu Asp Ile Arg Gln Gly Pro Lys Glu Pro Phe Arg Asp Tyr Val Asp
                    660                 665                 670

Arg Phe Tyr Lys Thr Leu Arg Ala Glu Gln Ala Ser Gln Glu Val Lys
                    675                 680                 685

Asn Trp Met Thr Glu Thr Leu Leu Val Gln Asn Ala Asn Pro Asp Cys
            690                 695                 700

Lys Thr Ile Leu Lys Ala Leu Gly Pro Gly Ala Thr Leu Glu Glu Met
705                 710                 715                 720

Met Thr Ala Cys Gln Gly Val Gly His His His His His
                    725                 730

<210> SEQ ID NO 4
```

```
<211> LENGTH: 27
<212> TYPE: PRT
<213> ORGANISM: Artificial Sequence
<220> FEATURE:
<223> OTHER INFORMATION: Synthesized Sequence

<400> SEQUENCE: 4

Gln Thr Pro Thr Asn Thr Ile Ser Val Thr Pro Thr Asn Asn Ser Thr
1               5                   10                  15

Pro Thr Asn Asn Ser Asn Pro Lys Pro Asn Pro
            20                  25

<210> SEQ ID NO 5
<211> LENGTH: 1853
<212> TYPE: PRT
<213> ORGANISM: Artificial Sequence
<220> FEATURE:
<223> OTHER INFORMATION: Synthesized Sequence

<400> SEQUENCE: 5

Met Arg Lys Val Ile Ser Met Leu Leu Val Val Ala Met Leu Thr Thr
1               5                   10                  15

Ile Phe Ala Ala Met Ile Pro Gln Thr Val Ser Ala Ala Thr Met Thr
                20                  25                  30

Val Glu Ile Gly Lys Val Thr Ala Ala Val Gly Ser Lys Val Glu Ile
            35                  40                  45

Pro Ile Thr Leu Lys Gly Val Pro Ser Lys Gly Met Ala Asn Cys Asp
        50                  55                  60

Phe Val Leu Gly Tyr Asp Pro Asn Val Leu Glu Val Thr Glu Val Lys
65                  70                  75                  80

Pro Gly Ser Ile Ile Lys Asp Pro Asp Pro Ser Lys Ser Phe Asp Ser
                85                  90                  95

Ala Ile Tyr Pro Asp Arg Lys Met Ile Val Phe Leu Phe Ala Glu Asp
                100                 105                 110

Ser Gly Arg Gly Thr Tyr Ala Ile Thr Gln Asp Gly Val Phe Ala Thr
            115                 120                 125

Ile Val Ala Thr Val Lys Ser Ala Ala Ala Pro Ile Thr Leu Leu
        130                 135                 140

Glu Val Gly Ala Phe Ala Asp Asn Asp Leu Val Glu Ile Ser Thr Thr
145                 150                 155                 160

Phe Val Ala Gly Gly Val Asn Leu Gly Ser Ser Val Pro Thr Thr Gln
                165                 170                 175

Pro Asn Val Pro Ser Asp Gly Val Val Val Glu Ile Gly Lys Val Thr
            180                 185                 190

Gly Ser Val Gly Thr Thr Val Glu Ile Pro Val Tyr Phe Arg Gly Val
        195                 200                 205

Pro Ser Lys Gly Ile Ala Asn Cys Asp Phe Val Phe Arg Tyr Asp Pro
    210                 215                 220

Asn Val Leu Glu Ile Ile Gly Ile Asp Pro Gly Asp Ile Ile Val Asp
225                 230                 235                 240

Pro Asn Pro Thr Lys Ser Phe Asp Thr Ala Ile Tyr Pro Asp Arg Lys
                245                 250                 255

Ile Ile Val Phe Leu Phe Ala Glu Asp Ser Gly Thr Gly Ala Tyr Ala
            260                 265                 270

Ile Thr Lys Asp Gly Val Phe Ala Lys Ile Arg Ala Thr Val Lys Ser
        275                 280                 285

Ser Ala Pro Gly Tyr Ile Thr Phe Asp Glu Val Gly Gly Phe Ala Asp
```

-continued

```
            290                 295                 300
Asn Asp Leu Val Glu Gln Lys Val Ser Phe Ile Asp Gly Gly Val Asn
305                 310                 315                 320

Val Gly Asn Ala Thr Pro Thr Lys Gly Ala Thr Pro Thr Asn Thr Ala
                325                 330                 335

Thr Pro Thr Lys Ser Ala Thr Ala Thr Pro Thr Arg Pro Ser Val Pro
                340                 345                 350

Thr Asn Thr Pro Thr Asn Thr Pro Ala Asn Thr Pro Val Ser Gly Asn
                355                 360                 365

Leu Lys Val Glu Phe Tyr Asn Ser Asn Pro Ser Asp Thr Thr Asn Ser
370                 375                 380

Ile Asn Pro Gln Phe Lys Val Thr Asn Thr Gly Ser Ser Ala Ile Asp
385                 390                 395                 400

Leu Ser Lys Leu Thr Leu Arg Tyr Tyr Tyr Thr Val Asp Gly Gln Lys
                405                 410                 415

Asp Gln Thr Phe Trp Cys Asp His Ala Ala Ile Ile Gly Ser Asn Gly
                420                 425                 430

Ser Tyr Asn Gly Ile Thr Ser Asn Val Lys Gly Thr Phe Val Lys Met
                435                 440                 445

Ser Ser Ser Thr Asn Asn Ala Asp Thr Tyr Leu Glu Ile Ser Phe Thr
                450                 455                 460

Gly Gly Thr Leu Glu Pro Gly Ala His Val Gln Ile Gln Gly Arg Phe
465                 470                 475                 480

Ala Lys Asn Asp Trp Ser Asn Tyr Thr Gln Ser Asn Asp Tyr Ser Phe
                485                 490                 495

Lys Ser Ala Ser Gln Phe Val Glu Trp Asp Gln Val Thr Ala Tyr Leu
                500                 505                 510

Asn Gly Val Leu Val Trp Gly Lys Glu Pro Gly Gly Ser Val Val Pro
                515                 520                 525

Ser Thr Gln Pro Val Thr Thr Pro Ala Thr Thr Lys Pro Pro Ala
530                 535                 540

Thr Thr Lys Pro Pro Ala Thr Thr Ile Pro Pro Ser Asp Asp Pro Asn
545                 550                 555                 560

Ala Ile Lys Ile Lys Val Asp Thr Val Asn Ala Lys Pro Gly Asp Thr
                565                 570                 575

Val Asn Ile Pro Val Arg Phe Ser Gly Ile Pro Ser Lys Gly Ile Ala
                580                 585                 590

Asn Cys Asp Phe Val Tyr Ser Tyr Asp Pro Asn Val Leu Glu Ile Ile
                595                 600                 605

Glu Ile Lys Pro Gly Glu Leu Ile Val Asp Pro Asn Pro Asp Lys Ser
610                 615                 620

Phe Asp Thr Ala Val Tyr Pro Asp Arg Lys Ile Ile Val Phe Leu Phe
625                 630                 635                 640

Ala Glu Asp Ser Gly Thr Gly Ala Tyr Ala Ile Thr Lys Asp Gly Val
                645                 650                 655

Phe Ala Thr Ile Val Ala Lys Val Lys Ser Gly Ala Pro Asn Gly Leu
                660                 665                 670

Ser Val Ile Lys Phe Val Glu Val Gly Gly Phe Ala Asn Asn Asp Leu
                675                 680                 685

Val Glu Gln Arg Thr Gln Phe Phe Asp Gly Gly Val Asn Val Gly Asp
                690                 695                 700

Thr Thr Val Pro Thr Thr Pro Thr Thr Pro Val Thr Thr Pro Thr Asp
705                 710                 715                 720
```

```
Asp Ser Asn Ala Val Arg Ile Lys Val Asp Thr Val Asn Ala Lys Pro
                725                 730                 735

Gly Asp Thr Val Arg Ile Pro Val Arg Phe Ser Gly Ile Pro Ser Lys
                740                 745                 750

Gly Ile Ala Asn Cys Asp Phe Val Tyr Ser Tyr Asp Pro Asn Val Leu
                755                 760                 765

Glu Ile Ile Glu Ile Glu Pro Gly Asp Ile Val Asp Pro Asn Pro
770                 775                 780

Asp Lys Ser Phe Asp Thr Ala Val Tyr Pro Asp Arg Lys Ile Ile Val
785                 790                 795                 800

Phe Leu Phe Ala Glu Asp Ser Gly Thr Gly Ala Tyr Ala Ile Thr Lys
                805                 810                 815

Asp Gly Val Phe Ala Thr Ile Val Ala Lys Val Lys Ser Gly Ala Pro
                820                 825                 830

Asn Gly Leu Ser Val Ile Lys Phe Val Glu Val Gly Gly Phe Ala Asn
                835                 840                 845

Asn Asp Leu Val Glu Gln Lys Thr Gln Phe Phe Asp Gly Gly Val Asn
                850                 855                 860

Val Gly Asp Thr Thr Glu Pro Ala Thr Pro Thr Thr Pro Val Thr Thr
865                 870                 875                 880

Pro Thr Thr Thr Asp Asp Leu Asp Ala Val Arg Ile Lys Val Asp Thr
                885                 890                 895

Val Asn Ala Lys Pro Gly Asp Thr Val Arg Ile Pro Val Arg Phe Ser
                900                 905                 910

Gly Ile Pro Ser Lys Gly Ile Ala Asn Cys Asp Phe Val Tyr Ser Tyr
                915                 920                 925

Asp Pro Asn Val Leu Glu Ile Ile Glu Ile Glu Pro Gly Asp Ile Ile
                930                 935                 940

Val Asp Pro Asn Pro Asp Lys Ser Phe Asp Thr Ala Val Tyr Pro Asp
945                 950                 955                 960

Arg Lys Ile Ile Val Phe Leu Phe Ala Glu Asp Ser Gly Thr Gly Ala
                965                 970                 975

Tyr Ala Ile Thr Lys Asp Gly Val Phe Ala Thr Ile Val Ala Lys Val
                980                 985                 990

Lys Ser Gly Ala Pro Asn Gly Leu Ser Val Ile Lys Phe Val Glu Val
                995                 1000                1005

Gly Gly Phe Ala Asn Asn Asp Leu Val Glu Gln Lys Thr Gln Phe
        1010                1015                1020

Phe Asp Gly Gly Val Asn Val Gly Asp Thr Thr Glu Pro Ala Thr
        1025                1030                1035

Pro Thr Thr Pro Val Thr Thr Pro Thr Thr Thr Asp Asp Leu Asp
        1040                1045                1050

Ala Val Arg Ile Lys Val Asp Thr Val Asn Ala Lys Pro Gly Asp
        1055                1060                1065

Thr Val Arg Ile Pro Val Arg Phe Ser Gly Ile Pro Ser Lys Gly
        1070                1075                1080

Ile Ala Asn Cys Asp Phe Val Tyr Ser Tyr Asp Pro Asn Val Leu
        1085                1090                1095

Glu Ile Ile Glu Ile Glu Pro Gly Asp Ile Ile Val Asp Pro Asn
        1100                1105                1110

Pro Asp Lys Ser Phe Asp Thr Ala Val Tyr Pro Asp Arg Lys Ile
        1115                1120                1125
```

```
Ile Val Phe Leu Phe Ala Glu Asp Ser Gly Thr Gly Ala Tyr Ala
1130                1135                1140

Ile Thr Lys Asp Gly Val Phe Ala Thr Ile Val Ala Lys Val Lys
1145                1150                1155

Glu Gly Ala Pro Asn Gly Leu Ser Val Ile Lys Phe Val Glu Val
1160                1165                1170

Gly Gly Phe Ala Asn Asn Asp Leu Val Glu Gln Lys Thr Gln Phe
1175                1180                1185

Phe Asp Gly Gly Val Asn Val Gly Asp Thr Thr Glu Pro Ala Thr
1190                1195                1200

Pro Thr Thr Pro Val Thr Thr Pro Thr Thr Thr Asp Asp Leu Asp
1205                1210                1215

Ala Val Arg Ile Lys Val Asp Thr Val Asn Ala Lys Pro Gly Asp
1220                1225                1230

Thr Val Arg Ile Pro Val Arg Phe Ser Gly Ile Pro Ser Lys Gly
1235                1240                1245

Ile Ala Asn Cys Asp Phe Val Tyr Ser Tyr Asp Pro Asn Val Leu
1250                1255                1260

Glu Ile Ile Glu Ile Glu Pro Gly Glu Leu Ile Val Asp Pro Asn
1265                1270                1275

Pro Thr Lys Ser Phe Asp Thr Ala Val Tyr Pro Asp Arg Lys Met
1280                1285                1290

Ile Val Phe Leu Phe Ala Glu Asp Ser Gly Thr Gly Ala Tyr Ala
1295                1300                1305

Ile Thr Glu Asp Gly Val Phe Ala Thr Ile Val Ala Lys Val Lys
1310                1315                1320

Ser Gly Ala Pro Asn Gly Leu Ser Val Ile Lys Phe Val Glu Val
1325                1330                1335

Gly Gly Phe Ala Asn Asn Asp Leu Val Glu Gln Lys Thr Gln Phe
1340                1345                1350

Phe Asp Gly Gly Val Asn Val Gly Asp Thr Thr Glu Pro Ala Thr
1355                1360                1365

Pro Thr Thr Pro Val Thr Thr Pro Thr Thr Thr Asp Asp Leu Asp
1370                1375                1380

Ala Val Arg Ile Lys Val Asp Thr Val Asn Ala Lys Pro Gly Asp
1385                1390                1395

Thr Val Arg Ile Pro Val Arg Phe Ser Gly Ile Pro Ser Lys Gly
1400                1405                1410

Ile Ala Asn Cys Asp Phe Val Tyr Ser Tyr Asp Pro Asn Val Leu
1415                1420                1425

Glu Ile Ile Glu Ile Glu Pro Gly Asp Ile Ile Val Asp Pro Asn
1430                1435                1440

Pro Asp Lys Ser Phe Asp Thr Ala Val Tyr Pro Asp Arg Lys Ile
1445                1450                1455

Ile Val Phe Leu Phe Ala Glu Asp Ser Gly Thr Gly Ala Tyr Ala
1460                1465                1470

Ile Thr Lys Asp Gly Val Phe Ala Thr Ile Val Ala Lys Val Lys
1475                1480                1485

Glu Gly Ala Pro Asn Gly Leu Ser Val Ile Lys Phe Val Glu Val
1490                1495                1500

Gly Gly Phe Ala Asn Asn Asp Leu Val Glu Gln Lys Thr Gln Phe
1505                1510                1515

Phe Asp Gly Gly Val Asn Val Gly Asp Thr Thr Val Pro Thr Thr
```

```
                    1520                1525                1530

Ser Pro Thr Thr Thr Pro Pro Glu Pro Thr Ile Thr Pro Asn Lys
    1535                1540                1545

Leu Thr Leu Lys Ile Gly Arg Ala Glu Gly Arg Pro Gly Asp Thr
1550                1555                1560

Val Glu Ile Pro Val Asn Leu Tyr Gly Val Pro Gln Lys Gly Ile
1565                1570                1575

Ala Ser Gly Asp Phe Val Val Ser Tyr Asp Pro Asn Val Leu Glu
1580                1585                1590

Ile Ile Glu Ile Glu Pro Gly Glu Leu Ile Val Asp Pro Asn Pro
1595                1600                1605

Thr Lys Ser Phe Asp Thr Ala Val Tyr Pro Asp Arg Lys Met Ile
1610                1615                1620

Val Phe Leu Phe Ala Glu Asp Ser Gly Thr Gly Ala Tyr Ala Ile
1625                1630                1635

Thr Glu Asp Gly Val Phe Ala Thr Ile Val Ala Lys Val Lys Glu
1640                1645                1650

Gly Ala Pro Glu Gly Phe Ser Ala Ile Glu Ile Ser Glu Phe Gly
1655                1660                1665

Ala Phe Ala Asp Asn Asp Leu Val Glu Val Glu Thr Asp Leu Ile
1670                1675                1680

Asn Gly Gly Val Leu Val Thr Asn Lys Pro Val Ile Glu Gly Tyr
1685                1690                1695

Lys Val Ser Gly Tyr Ile Leu Pro Asp Phe Ser Phe Asp Ala Thr
1700                1705                1710

Val Ala Pro Leu Val Lys Ala Gly Phe Lys Val Glu Ile Val Gly
1715                1720                1725

Thr Glu Leu Tyr Ala Val Thr Asp Ala Asn Gly Tyr Phe Glu Ile
1730                1735                1740

Thr Gly Val Pro Ala Asn Ala Ser Gly Tyr Thr Leu Lys Ile Ser
1745                1750                1755

Arg Ala Thr Tyr Leu Asp Arg Val Ile Ala Asn Val Val Val Thr
1760                1765                1770

Gly Asp Thr Ser Val Ser Thr Ser Gln Ala Pro Ile Met Met Trp
1775                1780                1785

Val Gly Asp Ile Val Lys Asp Asn Ser Ile Asn Leu Leu Asp Val
1790                1795                1800

Ala Glu Val Ile Arg Cys Phe Asn Ala Thr Lys Gly Ser Ala Asn
1805                1810                1815

Tyr Val Glu Glu Leu Asp Ile Asn Arg Asn Gly Ala Ile Asn Met
1820                1825                1830

Gln Asp Ile Met Ile Val His Lys His Phe Gly Ala Thr Ser Ser
1835                1840                1845

Asp Tyr Asp Ala Gln
    1850

<210> SEQ ID NO 6
<211> LENGTH: 27
<212> TYPE: PRT
<213> ORGANISM: Artificial Sequence
<220> FEATURE:
<223> OTHER INFORMATION: Synthesized Sequence

<400> SEQUENCE: 6

Gln Thr Pro Thr Asn Thr Ile Ser Val Thr Pro Thr Asn Asn Ser Thr
```

```
1               5                   10                  15
Pro Thr Asn Thr Ser Thr Pro Lys Pro Asn Pro
                20                  25

<210> SEQ ID NO 7
<211> LENGTH: 2299
<212> TYPE: PRT
<213> ORGANISM: Artificial Sequence
<220> FEATURE:
<223> OTHER INFORMATION: Synthesized Sequence

<400> SEQUENCE: 7

Met Gln Ser Pro Arg Leu Lys Arg Lys Ile Leu Ser Val Ile Leu Ala
1               5                   10                  15

Val Cys Tyr Ile Ile Ser Ser Phe Ser Ile Gln Phe Ala Ala Thr Pro
                20                  25                  30

Gln Val Asn Ile Ile Gly Ser Ala Gln Gly Ile Pro Gly Ser Thr
                35                  40              45

Val Lys Val Pro Ile Asn Leu Gln Asn Val Pro Glu Ile Gly Ile Asn
    50                  55                  60

Asn Cys Asp Phe Thr Ile Lys Phe Asp Ser Asp Ile Leu Asp Phe Asn
65                  70                  75                  80

Ser Val Glu Ala Gly Asp Ile Val Pro Leu Pro Val Ala Ser Phe Ser
                85                  90                  95

Ser Asn Asn Ser Lys Asp Ile Ile Lys Phe Leu Phe Ser Asp Ala Thr
                100                 105                 110

Gln Gly Asn Met Pro Ile Asn Glu Asn Gly Leu Phe Ala Val Ile Ser
                115                 120                 125

Phe Lys Ile Lys Asp Asn Ala Gln Lys Gly Ile Ser Asn Ile Lys Val
    130                 135                 140

Ser Ser Tyr Gly Ser Phe Ser Gly Met Ser Gly Lys Glu Met Gln Ser
145                 150                 155                 160

Leu Ser Pro Thr Phe Phe Ser Gly Ser Ile Asp Val Ser Asp Val Ser
                165                 170                 175

Thr Ser Lys Leu Asp Val Lys Val Gly Asn Val Glu Gly Ile Ala Gly
                180                 185                 190

Thr Glu Val Asn Val Pro Ile Thr Phe Glu Asn Val Pro Asp Asn Gly
                195                 200                 205

Ile Asn Asn Cys Asn Phe Thr Leu Ser Tyr Asp Ser Asn Ala Leu Glu
    210                 215                 220

Phe Leu Thr Thr Glu Ala Gly Asn Ile Ile Pro Leu Ala Ile Ala Asp
225                 230                 235                 240

Tyr Ser Ser Tyr Arg Ser Met Glu Gly Lys Ile Lys Phe Leu Phe Ser
                245                 250                 255

Asp Ser Ser Gln Gly Thr Arg Ser Ile Lys Asn Asp Gly Val Phe Ala
                260                 265                 270

Asn Ile Lys Phe Lys Ile Lys Gly Asn Ala Ile Arg Asp Thr Tyr Arg
    275                 280                 285

Ile Asp Leu Ser Glu Leu Gly Ser Phe Ser Ser Lys Gln Asn Asn Asn
    290                 295                 300

Leu Lys Ser Ile Ala Thr Gln Phe Leu Ser Gly Ser Val Asn Val Lys
305                 310                 315                 320

Asp Ile Glu Ser Ser Val Ser Pro Thr Thr Ser Val His Pro Thr Pro
                325                 330                 335

Thr Ser Val Pro Pro Thr Pro Thr Lys Ser Ser Pro Gly Asn Lys Met
```

-continued

```
                340                 345                 350
Lys Ile Gln Ile Gly Asp Val Lys Ala Asn Gln Gly Asp Thr Val Ile
        355                 360                 365

Val Pro Ile Thr Phe Asn Glu Val Pro Val Met Gly Val Asn Asn Cys
370                 375                 380

Asn Phe Thr Leu Ala Tyr Asp Lys Asn Ile Met Glu Phe Ile Ser Ala
385                 390                 395                 400

Asp Ala Gly Asp Ile Val Thr Leu Pro Met Ala Asn Tyr Ser Tyr Asn
                405                 410                 415

Met Pro Ser Asp Gly Leu Val Lys Phe Leu Tyr Asn Asp Gln Ala Gln
        420                 425                 430

Gly Ala Met Ser Ile Lys Glu Asp Gly Thr Phe Ala Asn Val Lys Phe
            435                 440                 445

Lys Ile Lys Gln Ser Ala Ala Phe Gly Lys Tyr Ser Val Gly Ile Lys
450                 455                 460

Ala Ile Gly Ser Ile Ser Ala Leu Ser Asn Ser Lys Leu Ile Pro Ile
465                 470                 475                 480

Glu Ser Ile Phe Lys Asp Gly Ser Ile Thr Val Thr Asn Lys Pro Ile
                485                 490                 495

Val Asn Ile Glu Ile Gly Lys Val Lys Val Lys Ala Gly Asp Lys Ile
            500                 505                 510

Lys Val Pro Val Glu Ile Lys Asp Ile Pro Ser Ile Gly Ile Asn Asn
        515                 520                 525

Cys Asn Phe Thr Leu Lys Tyr Asn Ser Asn Val Leu Lys Tyr Val Ser
    530                 535                 540

Asn Glu Ala Gly Thr Ile Val Pro Ala Pro Leu Ala Asn Leu Ser Ile
545                 550                 555                 560

Asn Lys Pro Asp Glu Gly Ile Ile Lys Leu Leu Phe Ser Asp Ala Ser
                565                 570                 575

Gln Gly Gly Met Pro Ile Lys Asp Asn Gly Ile Phe Val Asn Leu Glu
            580                 585                 590

Phe Gln Ala Val Asn Asp Ala Asn Ile Gly Val Tyr Gly Leu Glu Leu
        595                 600                 605

Asp Thr Ile Gly Ala Phe Ser Gly Ile Ser Ser Ala Lys Met Thr Ser
    610                 615                 620

Ile Glu Pro Gln Phe Asn Asn Gly Ser Ile Glu Ile Phe Asn Ser Ala
625                 630                 635                 640

Gln Thr Pro Val Pro Ser Asn Thr Glu Val Gln Thr Pro Thr Asn Thr
                645                 650                 655

Ile Ser Val Thr Pro Thr Asn Asn Ser Thr Pro Thr Asn Asn Ser Thr
            660                 665                 670

Pro Lys Pro Asn Pro Leu Tyr Asn Leu Asn Val Asn Ile Gly Glu Ile
        675                 680                 685

Ser Gly Glu Ala Gly Val Ile Glu Val Pro Ile Glu Phe Lys Asn
    690                 695                 700

Val Pro Asp Phe Gly Ile Asn Asn Cys Asp Phe Ser Val Lys Tyr Asp
705                 710                 715                 720

Lys Ser Ile Phe Glu Tyr Val Thr Tyr Glu Ala Gly Ser Ile Val Lys
                725                 730                 735

Asp Ser Ile Val Asn Leu Ala Cys Met Glu Asn Ser Gly Ile Ile Asn
            740                 745                 750

Leu Leu Phe Asn Asp Ala Thr Gln Ser Ser Pro Ile Lys Asn Asn
        755                 760                 765
```

```
Gly Val Phe Ala Lys Leu Lys Phe Lys Ile Asn Ser Asn Ala Ala Ser
    770             775             780

Gly Thr Tyr Gln Ile Asn Ala Glu Gly Tyr Gly Lys Phe Ser Gly Asn
785             790             795             800

Leu Asn Gly Lys Leu Thr Ser Ile Asn Pro Ile Phe Glu Asn Gly Ile
                805             810             815

Ile Asn Ile Gly Asn Val Thr Val Lys Pro Thr Ser Thr Pro Ala Asp
            820             825             830

Ser Ser Thr Ile Thr Pro Thr Ala Thr Pro Ala Thr Pro Thr Ile
        835             840             845

Lys Gly Thr Pro Thr Val Thr Pro Ile Tyr Trp Met Asn Val Leu Ile
    850             855             860

Gly Asn Met Asn Ala Ala Ile Gly Glu Glu Val Val Pro Ile Glu
865             870             875             880

Phe Lys Asn Val Pro Pro Phe Gly Ile Asn Asn Cys Asp Phe Lys Leu
                885             890             895

Val Tyr Asp Ser Asn Ala Leu Glu Leu Lys Lys Val Glu Ala Gly Asp
            900             905             910

Ile Val Pro Glu Pro Leu Ala Asn Leu Ser Ser Asn Lys Ser Glu Gly
            915             920             925

Lys Ile Gln Phe Leu Phe Asn Asp Ala Ser Gln Gly Ser Met Gln Ile
    930             935             940

Glu Asn Gly Gly Val Phe Ala Lys Ile Thr Phe Lys Val Lys Ser Thr
945             950             955             960

Ala Ala Ser Gly Ile Tyr Asn Ile Arg Lys Asp Ser Val Gly Ser Phe
            965             970             975

Ser Gly Leu Ile Asp Asn Lys Met Thr Ser Ile Gly Pro Lys Phe Thr
            980             985             990

Asp Gly Ser Ile Val Val Gly Thr Val Thr Pro Thr Ala Thr Ala Thr
            995             1000            1005

Pro Ser Ala Ile Val Thr Thr Ile Thr Pro Thr Ala Thr Thr Lys
    1010            1015            1020

Pro Ile Ala Thr Pro Thr Ile Lys Gly Pro Thr Ala Thr Pro
    1025            1030            1035

Met Tyr Trp Met Asn Val Val Ile Gly Lys Met Asn Ala Glu Val
    1040            1045            1050

Gly Gly Glu Val Val Pro Ile Glu Phe Asn Val Pro Ser
1055            1060            1065

Phe Gly Ile Asn Asn Cys Asp Phe Lys Leu Val Tyr Asp Ala Thr
    1070            1075            1080

Ala Leu Glu Leu Lys Asn Val Glu Ala Gly Asp Ile Ile Lys Thr
    1085            1090            1095

Pro Leu Ala Asn Phe Ser Asn Asn Lys Ser Glu Glu Gly Lys Ile
    1100            1105            1110

Ser Phe Leu Phe Asn Asp Ala Ser Gln Gly Ser Met Gln Ile Glu
    1115            1120            1125

Asn Gly Gly Val Phe Ala Lys Ile Thr Phe Lys Val Lys Ser Thr
    1130            1135            1140

Thr Ala Thr Gly Val Tyr Asp Leu Arg Lys Asp Leu Val Gly Ser
    1145            1150            1155

Phe Ser Gly Leu Lys Asp Asn Lys Met Thr Ser Ile Gly Ala Glu
    1160            1165            1170
```

```
Phe Thr Asn Gly Ser Ile Thr Val Ala Ala Thr Ala Pro Thr Val
1175                1180                1185

Thr Pro Thr Val Asn Ala Thr Pro Ser Ala Ala Thr Pro Thr Val
1190                1195                1200

Thr Pro Thr Ala Thr Ala Thr Pro Ser Val Thr Ile Pro Thr Val
1205                1210                1215

Thr Pro Thr Ala Thr Ala Thr Pro Ser Val Thr Ile Pro Thr Val
1220                1225                1230

Thr Pro Thr Ala Thr Ala Thr Pro Ser Ala Ala Thr Pro Thr Val
1235                1240                1245

Thr Pro Thr Ala Thr Ala Thr Pro Ser Val Thr Ile Pro Thr Val
1250                1255                1260

Thr Pro Thr Val Thr Ala Thr Pro Ser Asp Thr Ile Pro Thr Val
1265                1270                1275

Thr Pro Thr Ala Thr Ala Thr Pro Ser Ala Ile Val Thr Thr Ile
1280                1285                1290

Thr Pro Thr Ala Thr Ala Lys Pro Ile Ala Thr Pro Thr Ile Lys
1295                1300                1305

Gly Thr Pro Thr Ala Thr Pro Met Tyr Trp Met Asn Val Val Ile
1310                1315                1320

Gly Lys Met Asn Ala Glu Val Gly Gly Glu Val Val Val Pro Ile
1325                1330                1335

Glu Phe Lys Asn Val Pro Ser Phe Gly Ile Asn Asn Cys Asp Phe
1340                1345                1350

Lys Leu Val Tyr Asp Ala Thr Ala Leu Glu Leu Lys Asn Val Glu
1355                1360                1365

Ala Gly Asp Ile Ile Lys Thr Pro Leu Ala Asn Phe Ser Asn Asn
1370                1375                1380

Lys Ser Glu Glu Gly Lys Ile Ser Phe Leu Phe Asn Asp Ala Ser
1385                1390                1395

Gln Gly Ser Met Gln Ile Glu Asn Gly Gly Val Ser Ala Lys Ile
1400                1405                1410

Thr Phe Lys Val Lys Ser Thr Thr Ala Ile Gly Val Tyr Asp Ile
1415                1420                1425

Arg Lys Asp Leu Ile Gly Ser Phe Ser Gly Leu Lys Asp Ser Lys
1430                1435                1440

Met Thr Ser Ile Gly Ala Glu Phe Thr Asn Gly Ser Ile Thr Val
1445                1450                1455

Ala Thr Thr Ala Pro Thr Val Thr Pro Thr Ala Thr Ala Thr Pro
1460                1465                1470

Ser Val Thr Ile Pro Thr Val Thr Pro Thr Ala Thr Ala Thr Pro
1475                1480                1485

Gly Thr Ala Thr Pro Gly Thr Ala Thr Pro Thr Ala Thr Ala Thr
1490                1495                1500

Pro Gly Ala Ala Thr Pro Thr Glu Thr Ala Thr Pro Ser Val Met
1505                1510                1515

Ile Pro Thr Val Thr Pro Thr Ala Thr Ala Thr Pro Thr Ala Thr
1520                1525                1530

Ala Thr Pro Thr Val Lys Gly Thr Pro Thr Ile Lys Pro Val Tyr
1535                1540                1545

Lys Met Asn Val Val Ile Gly Arg Val Asn Val Ala Gly Glu
1550                1555                1560

Glu Val Val Val Pro Val Glu Phe Lys Asn Ile Pro Ala Ile Gly
```

-continued

```
            1565                1570                1575
Val Asn Asn Cys Asn Phe Val Leu Glu Tyr Asp Ala Asn Val Leu
        1580                1585                1590
Glu Val Lys Lys Val Asp Ala Gly Glu Ile Val Pro Asp Ala Leu
        1595                1600                1605
Ile Asn Phe Gly Ser Asn Asn Ser Asp Glu Gly Lys Val Tyr Phe
        1610                1615                1620
Leu Phe Asn Asp Ala Leu Gln Gly Arg Met Gln Ile Ala Asn Asp
        1625                1630                1635
Gly Ile Phe Ala Asn Ile Thr Phe Lys Val Lys Ser Ser Ala Ala
        1640                1645                1650
Ala Gly Ile Tyr Asn Ile Arg Lys Asp Ser Val Gly Ala Phe Ser
        1655                1660                1665
Gly Leu Val Asp Lys Leu Val Pro Ile Ser Ala Glu Phe Thr Asp
        1670                1675                1680
Gly Ser Ile Ser Val Glu Ser Ala Lys Ser Thr Pro Thr Ala Thr
        1685                1690                1695
Ala Thr Gly Thr Asn Val Thr Pro Thr Val Ala Ala Thr Val Thr
        1700                1705                1710
Pro Thr Ala Thr Pro Ala Ser Thr Thr Pro Thr Ala Thr Pro Thr
        1715                1720                1725
Ala Thr Ser Thr Val Lys Gly Thr Pro Thr Ala Thr Pro Leu Tyr
        1730                1735                1740
Ser Met Asn Val Ile Ile Gly Lys Val Asn Ala Glu Ala Ser Gly
        1745                1750                1755
Glu Val Val Val Pro Val Glu Phe Lys Asp Val Pro Ser Ile Gly
        1760                1765                1770
Ile Asn Asn Cys Asn Phe Ile Leu Glu Tyr Asp Ala Ser Ala Leu
        1775                1780                1785
Glu Leu Asp Ser Ala Glu Ala Gly Glu Ile Val Pro Val Pro Leu
        1790                1795                1800
Gly Asn Phe Ser Ser Asn Asn Lys Asp Glu Gly Lys Ile Tyr Phe
        1805                1810                1815
Leu Phe Ser Asp Gly Thr Gln Gly Arg Met Gln Ile Val Asn Asp
        1820                1825                1830
Gly Ile Phe Ala Lys Ile Lys Phe Lys Val Lys Ser Thr Ala Ser
        1835                1840                1845
Asp Gly Thr Tyr Tyr Ile Arg Lys Asp Ser Val Gly Ala Phe Ser
        1850                1855                1860
Gly Leu Ile Glu Lys Lys Ile Ile Lys Ile Gly Ala Glu Phe Thr
        1865                1870                1875
Asp Gly Ser Ile Thr Val Arg Ser Leu Thr Pro Thr Pro Thr Val
        1880                1885                1890
Thr Pro Asn Val Ala Ser Pro Thr Pro Thr Lys Val Val Ala Glu
        1895                1900                1905
Pro Thr Ser Asn Gln Pro Ala Gly Pro Gly Pro Ile Thr Gly Thr
        1910                1915                1920
Ile Pro Thr Ala Thr Thr Thr Ala Thr Ala Thr Pro Thr Lys Ala
        1925                1930                1935
Ser Val Ala Thr Ala Thr Pro Thr Ala Thr Pro Ile Val Val Val
        1940                1945                1950
Glu Pro Thr Ile Val Arg Pro Gly Tyr Asn Lys Asp Ala Asp Leu
        1955                1960                1965
```

```
Ala Val Phe Ile Ser Ser Asp Lys Ser Arg Tyr Glu Glu Ser Ser
    1970                1975                1980

Ile Ile Thr Tyr Ser Ile Glu Tyr Lys Asn Ile Gly Lys Val Asn
    1985                1990                1995

Ala Thr Asn Val Lys Ile Ala Ala Gln Ile Pro Lys Phe Thr Lys
    2000                2005                2010

Val Tyr Asp Ala Ala Lys Gly Ala Val Lys Gly Ser Glu Ile Val
    2015                2020                2025

Trp Met Ile Gly Asn Leu Ala Val Gly Glu Ser Tyr Thr Lys Glu
    2030                2035                2040

Tyr Lys Val Lys Val Asp Ser Leu Thr Lys Ser Glu Glu Tyr Thr
    2045                2050                2055

Asp Asn Thr Val Thr Ile Ser Ser Asp Gln Thr Val Asp Ile Pro
    2060                2065                2070

Glu Asn Ile Thr Thr Gly Asn Asp Asp Lys Ser Thr Ile Arg Val
    2075                2080                2085

Met Leu Tyr Ser Asn Arg Phe Thr Pro Gly Ser His Ser Ser Tyr
    2090                2095                2100

Ile Leu Gly Tyr Lys Asp Lys Thr Phe Lys Pro Lys Gln Asn Val
    2105                2110                2115

Thr Arg Ala Glu Val Ala Ala Met Phe Ala Arg Ile Met Gly Leu
    2120                2125                2130

Thr Val Lys Asp Gly Ala Lys Ser Ser Tyr Lys Asp Val Ser Asn
    2135                2140                2145

Lys His Trp Ala Leu Lys Tyr Ile Glu Ala Val Thr Lys Ser Gly
    2150                2155                2160

Ile Phe Lys Gly Tyr Lys Asp Ser Thr Phe His Pro Asn Ala Pro
    2165                2170                2175

Ile Thr Arg Ala Glu Leu Ser Thr Val Ile Phe Asn Tyr Leu His
    2180                2185                2190

Leu Asn Asn Ile Ala Pro Ser Lys Val His Phe Thr Asp Ile Asn
    2195                2200                2205

Lys His Trp Ala Lys Asn Tyr Ile Glu Glu Ile Tyr Arg Phe Lys
    2210                2215                2220

Leu Ile Gln Gly Tyr Ser Asp Gly Ser Phe Lys Pro Asn Asn Asn
    2225                2230                2235

Ile Thr Arg Ala Glu Val Val Thr Met Ile Asn Arg Met Leu Tyr
    2240                2245                2250

Arg Gly Pro Leu Lys Val Lys Val Gly Ser Phe Pro Asp Val Ser
    2255                2260                2265

Pro Lys Tyr Trp Ala Tyr Gly Asp Ile Glu Glu Ala Ser Arg Asn
    2270                2275                2280

His Lys Tyr Thr Arg Asp Glu Lys Asp Gly Ser Glu Ile Leu Ile
    2285                2290                2295

Glu

<210> SEQ ID NO 8
<211> LENGTH: 810
<212> TYPE: PRT
<213> ORGANISM: Artificial Sequence
<220> FEATURE:
<223> OTHER INFORMATION: Synthesized Sequence

<400> SEQUENCE: 8
```

-continued

```
Gln Val Thr Leu Lys Glu Ser Gly Pro Gly Ile Leu Gln Pro Ser Gln
 1               5                  10                  15
Thr Leu Ser Leu Thr Cys Ser Phe Ser Gly Phe Ser Leu Ser Thr Ser
                20                  25                  30
Gly Met Gly Leu Ser Trp Ile Arg Gln Pro Ser Gly Lys Gly Leu Glu
            35                  40                  45
Trp Leu Ala His Ile Tyr Trp Asp Asp Lys Arg Tyr Asn Pro Ser
 50                  55                  60
Leu Lys Ser Arg Leu Thr Ile Ser Lys Asp Thr Ser Ser Asn Gln Val
 65                  70                  75                  80
Phe Leu Lys Ile Thr Ile Val Asp Thr Ala Asp Ala Thr Tyr Tyr
                    85                  90                  95
Cys Ala Arg Ser Ser His Tyr Tyr Gly Tyr Gly Tyr Gly Tyr Phe
                100                 105                 110
Asp Val Trp Gly Ala Gly Thr Thr Val Thr Val Ser Ser Ala Lys Thr
            115                 120                 125
Lys Gly Pro Ser Val Phe Pro Leu Ala Pro Cys Ser Arg Ser Thr Ser
        130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Arg Val Glu
    210                 215                 220
Ser Lys Tyr Gly Pro Pro Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
```

```
            420                 425                 430
Met His Glu Ala Leu His Asn His Tyr Thr Gln Lys Ser Leu Ser Leu
                435                 440                 445

Ser Leu Gly Lys Ala Ser Leu Glu Met Gly Ala Arg Ala Ser Ile Leu
    450                 455                 460

Ser Gly Gly Glu Leu Asp Arg Trp Glu Lys Ile Arg Leu Arg Pro Gly
465                 470                 475                 480

Gly Lys Lys Tyr Lys Leu Lys His Ile Val Trp Ala Ser Arg Glu
                485                 490                 495

Leu Glu Arg Phe Ala Val Asn Pro Gly Leu Leu Glu Thr Ser Glu Gly
                500                 505                 510

Cys Arg Gln Ile Leu Gly Gln Leu Gln Pro Ser Leu Gln Thr Gly Ser
            515                 520                 525

Glu Glu Leu Arg Ser Leu Tyr Asn Thr Val Ala Thr Leu Tyr Cys Val
        530                 535                 540

His Gln Arg Ile Glu Ile Lys Asp Thr Lys Glu Ala Leu Asp Lys Ile
545                 550                 555                 560

Glu Glu Glu Gln Asn Lys Ser Lys Lys Ala Gln Gln Ala Ala Ala
                565                 570                 575

Asp Thr Gly His Ser Asn Gln Val Ser Gln Asn Tyr Pro Ile Val Gln
            580                 585                 590

Asn Ile Gln Gly Gln Met Val His Gln Ala Ile Ser Pro Arg Thr Leu
        595                 600                 605

Asn Ala Trp Val Lys Val Val Glu Lys Ala Phe Ser Pro Glu Val
610                 615                 620

Ile Pro Met Phe Ser Ala Leu Ser Glu Gly Ala Thr Pro Gln Asp Leu
625                 630                 635                 640

Asn Thr Met Leu Asn Thr Val Gly Gly His Gln Ala Ala Met Gln Met
                645                 650                 655

Leu Lys Glu Thr Ile Asn Glu Glu Ala Ala Glu Trp Asp Arg Val His
            660                 665                 670

Pro Val His Ala Gly Pro Ile Ala Pro Gly Gln Met Arg Glu Pro Arg
        675                 680                 685

Gly Ser Asp Ile Ala Gly Thr Thr Ser Thr Leu Gln Glu Gln Ile Gly
690                 695                 700

Trp Met Thr His Asn Pro Pro Ile Pro Val Gly Glu Ile Tyr Lys Arg
705                 710                 715                 720

Trp Ile Ile Leu Gly Leu Asn Lys Ile Val Arg Met Tyr Ser Pro Thr
                725                 730                 735

Ser Ile Leu Asp Ile Arg Gln Gly Pro Lys Glu Pro Phe Arg Asp Tyr
            740                 745                 750

Val Asp Arg Phe Tyr Lys Thr Leu Arg Ala Glu Gln Ala Ser Gln Glu
        755                 760                 765

Val Lys Asn Trp Met Thr Glu Thr Leu Leu Val Gln Asn Ala Asn Pro
770                 775                 780

Asp Cys Lys Thr Ile Leu Lys Ala Leu Gly Pro Gly Ala Thr Leu Glu
785                 790                 795                 800

Glu Met Met Thr Ala Cys Gln Gly Val Gly
                805                 810

<210> SEQ ID NO 9
<211> LENGTH: 847
<212> TYPE: PRT
<213> ORGANISM: Artificial Sequence
```

<220> FEATURE:
<223> OTHER INFORMATION: Synthesized Sequence

<400> SEQUENCE: 9

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400
```

-continued

```
Pro Val Leu Asp Ser Asp Gly Ser Phe Phe Leu Tyr Ser Arg Leu Thr
            405                 410                 415
Val Asp Lys Ser Arg Trp Gln Glu Gly Asn Val Phe Ser Cys Ser Val
        420                 425                 430
Met His Glu Ala Leu His Asn His Tyr Thr Gln Lys Ser Leu Ser Leu
            435                 440                 445
Ser Leu Gly Lys Ala Ser Gln Thr Pro Thr Asn Thr Ile Ser Val Thr
    450                 455                 460
Pro Thr Asn Asn Ser Thr Pro Thr Asn Asn Ser Asn Pro Lys Pro Asn
465                 470                 475                 480
Pro Ala Ser Leu Glu Met Gly Ala Arg Ala Ser Ile Leu Ser Gly Gly
                485                 490                 495
Glu Leu Asp Arg Trp Glu Lys Ile Arg Leu Arg Pro Gly Gly Lys Lys
            500                 505                 510
Lys Tyr Lys Leu Lys His Ile Val Trp Ala Ser Arg Glu Leu Glu Arg
        515                 520                 525
Phe Ala Val Asn Pro Gly Leu Leu Glu Thr Ser Glu Gly Cys Arg Gln
    530                 535                 540
Ile Leu Gly Gln Leu Gln Pro Ser Leu Gln Thr Gly Ser Glu Glu Leu
545                 550                 555                 560
Arg Ser Leu Tyr Asn Thr Val Ala Thr Leu Tyr Cys Val His Gln Arg
                565                 570                 575
Ile Glu Ile Lys Asp Thr Lys Glu Ala Leu Asp Lys Ile Glu Glu Glu
            580                 585                 590
Gln Asn Lys Ser Val Asp Ser Glu Phe Ala Gln Gln Ala Ala Ala Asp
        595                 600                 605
Thr Gly His Ser Asn Gln Val Ser Gln Asn Tyr Pro Ile Val Gln Asn
    610                 615                 620
Ile Gln Gly Gln Met Val His Gln Ala Ile Ser Pro Arg Thr Leu Asn
625                 630                 635                 640
Ala Trp Val Lys Val Val Glu Glu Lys Ala Phe Ser Pro Glu Val Ile
                645                 650                 655
Pro Met Phe Ser Ala Leu Ser Glu Gly Ala Thr Pro Gln Asp Leu Asn
            660                 665                 670
Thr Met Leu Asn Thr Val Gly Gly His Gln Ala Ala Met Gln Met Leu
        675                 680                 685
Lys Glu Thr Ile Asn Glu Glu Ala Ala Glu Trp Asp Arg Val His Pro
    690                 695                 700
Val His Ala Gly Pro Ile Ala Pro Gly Gln Met Arg Glu Pro Arg Gly
705                 710                 715                 720
Ser Asp Ile Ala Gly Thr Thr Ser Thr Leu Gln Glu Gln Ile Gly Trp
                725                 730                 735
Met Thr His Asn Pro Pro Ile Pro Val Gly Glu Ile Tyr Lys Arg Trp
            740                 745                 750
Ile Ile Leu Gly Leu Asn Lys Ile Val Arg Met Tyr Ser Pro Thr Ser
        755                 760                 765
Ile Leu Asp Ile Arg Gln Gly Pro Lys Glu Pro Phe Arg Asp Tyr Val
    770                 775                 780
Asp Arg Phe Tyr Lys Thr Leu Arg Ala Glu Gln Ala Ser Gln Glu Val
785                 790                 795                 800
Lys Asn Trp Met Thr Glu Thr Leu Leu Val Gln Asn Ala Asn Pro Asp
                805                 810                 815
```

-continued

```
Cys Lys Thr Ile Leu Lys Ala Leu Gly Pro Gly Ala Thr Leu Glu Glu
                 820                 825                 830

Met Met Thr Ala Cys Gln Gly Val Gly His His His His His His
                835                 840                 845

<210> SEQ ID NO 10
<211> LENGTH: 689
<212> TYPE: PRT
<213> ORGANISM: Artificial Sequence
<220> FEATURE:
<223> OTHER INFORMATION: Synthesized Sequence

<400> SEQUENCE: 10

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Gly Met Gly Leu Ser Trp Ile Arg Gln Pro Ser Gly Lys Gly Leu Glu
            35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
                100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
    450                 455                 460

Pro Thr Asn Asn Ser Thr Pro Thr Asn Asn Ser Asn Pro Lys Pro Asn
465                 470                 475                 480

Pro Ala Ser Met Gly Gly Lys Trp Ser Lys Arg Ser Val Val Gly Trp
                485                 490                 495

Pro Thr Val Arg Glu Arg Met Arg Arg Ala Glu Pro Ala Ala Asp Gly
            500                 505                 510

Val Gly Ala Val Ser Arg Asp Leu Glu Lys His Gly Ala Ile Thr Ser
        515                 520                 525

Ser Asn Thr Ala Ala Asn Asn Ala Asp Cys Ala Trp Leu Glu Ala Gln
    530                 535                 540

Glu Glu Glu Glu Val Gly Phe Pro Val Arg Pro Gln Val Pro Leu Arg
545                 550                 555                 560

Pro Met Thr Tyr Lys Gly Ala Leu Asp Leu Ser His Phe Leu Lys Glu
                565                 570                 575

Lys Gly Gly Leu Glu Gly Leu Ile Tyr Ser Gln Lys Arg Gln Asp Ile
            580                 585                 590

Leu Asp Leu Trp Val Tyr His Thr Gln Gly Tyr Phe Pro Asp Trp Gln
        595                 600                 605

Asn Tyr Thr Pro Gly Pro Gly Ile Arg Tyr Pro Leu Thr Phe Gly Trp
    610                 615                 620

Cys Phe Lys Leu Val Pro Val Glu Pro Glu Lys Val Glu Glu Ala Asn
625                 630                 635                 640

Glu Gly Glu Asn Asn Ser Leu Leu His Pro Met Ser Leu His Gly Met
                645                 650                 655

Asp Asp Pro Glu Arg Glu Val Leu Val Trp Lys Phe Asp Ser Arg Leu
            660                 665                 670

Ala Phe His His Met Ala Arg Glu Leu His Pro Glu Tyr Tyr Lys Asp
        675                 680                 685

Cys

<210> SEQ ID NO 11
<211> LENGTH: 1051
<212> TYPE: PRT
<213> ORGANISM: Artificial Sequence
<220> FEATURE:
<223> OTHER INFORMATION: Synthesized Sequence

<400> SEQUENCE: 11

Gln Val Thr Leu Lys Glu Ser Gly Pro Gly Ile Leu Gln Pro Ser Gln
```

-continued

```
1               5                   10                  15
Thr Leu Ser Leu Thr Cys Ser Phe Ser Gly Phe Ser Leu Ser Thr Ser
            20                  25                  30
Gly Met Gly Leu Ser Trp Ile Arg Gln Pro Ser Gly Lys Gly Leu Glu
            35                  40                  45
Trp Leu Ala His Ile Tyr Trp Asp Asp Lys Arg Tyr Asn Pro Ser
 50                  55                  60
Leu Lys Ser Arg Leu Thr Ile Ser Lys Asp Thr Ser Ser Asn Gln Val
 65                  70                  75                  80
Phe Leu Lys Ile Thr Ile Val Asp Thr Ala Asp Ala Thr Tyr Tyr
                85                  90                  95
Cys Ala Arg Ser Ser His Tyr Tyr Gly Tyr Gly Tyr Gly Gly Tyr Phe
                100                 105                 110
Asp Val Trp Gly Ala Gly Thr Thr Val Thr Val Ser Ser Ala Lys Thr
                115                 120                 125
Lys Gly Pro Ser Val Phe Pro Leu Ala Pro Cys Ser Arg Ser Thr Ser
                130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
Val Val Thr Val Pro Ser Ser Ser Leu Gly Thr Lys Thr Tyr Thr Cys
                195                 200                 205
Asn Val Asp His Lys Pro Ser Asn Thr Lys Val Asp Lys Arg Val Glu
                210                 215                 220
Ser Lys Tyr Gly Pro Pro Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
Gln Glu Asp Pro Glu Val Gln Phe Asn Trp Tyr Val Asp Gly Val Glu
                275                 280                 285
Val His Asn Ala Lys Thr Lys Pro Arg Glu Glu Gln Phe Asn Ser Thr
                290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Gln Glu Glu Met Thr Lys Asn Gln Val
                355                 360                 365
Ser Leu Thr Cys Leu Val Lys Gly Phe Tyr Pro Ser Asp Ile Ala Val
                370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
                420                 425                 430
```

```
Met His Glu Ala Leu His Asn His Tyr Thr Gln Lys Ser Leu Ser Leu
            435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Leu Glu Met Gly Ala Arg Ala Ser Ile Leu Ser Gly Gly
            485                 490                 495

Glu Leu Asp Arg Trp Glu Lys Ile Arg Leu Arg Pro Gly Gly Lys Lys
            500                 505                 510

Lys Tyr Lys Leu Lys His Ile Val Trp Ala Ser Arg Glu Leu Glu Arg
            515                 520                 525

Phe Ala Val Asn Pro Gly Leu Leu Glu Thr Ser Glu Gly Cys Arg Gln
530                 535                 540

Ile Leu Gly Gln Leu Gln Pro Ser Leu Gln Thr Gly Ser Glu Glu Leu
545                 550                 555                 560

Arg Ser Leu Tyr Asn Thr Val Ala Thr Leu Tyr Cys Val His Gln Arg
            565                 570                 575

Ile Glu Ile Lys Asp Thr Lys Glu Ala Leu Asp Lys Ile Glu Glu Glu
            580                 585                 590

Gln Asn Lys Ser Val Asp Ser Glu Phe Ala Gln Gln Ala Ala Ala Asp
            595                 600                 605

Thr Gly His Ser Asn Gln Val Ser Gln Asn Tyr Pro Ile Val Gln Asn
            610                 615                 620

Ile Gln Gly Gln Met Val His Gln Ala Ile Ser Pro Arg Thr Leu Asn
625                 630                 635                 640

Ala Trp Val Lys Val Val Glu Glu Lys Ala Phe Ser Pro Glu Val Ile
            645                 650                 655

Pro Met Phe Ser Ala Leu Ser Glu Gly Ala Thr Pro Gln Asp Leu Asn
            660                 665                 670

Thr Met Leu Asn Thr Val Gly Gly His Gln Ala Ala Met Gln Met Leu
            675                 680                 685

Lys Glu Thr Ile Asn Glu Glu Ala Ala Glu Trp Asp Arg Val His Pro
            690                 695                 700

Val His Ala Gly Pro Ile Ala Pro Gly Gln Met Arg Glu Pro Arg Gly
705                 710                 715                 720

Ser Asp Ile Ala Gly Thr Thr Ser Thr Leu Gln Glu Gln Ile Gly Trp
            725                 730                 735

Met Thr His Asn Pro Pro Ile Pro Val Gly Glu Ile Tyr Lys Arg Trp
            740                 745                 750

Ile Ile Leu Gly Leu Asn Lys Ile Val Arg Met Tyr Ser Pro Thr Ser
            755                 760                 765

Ile Leu Asp Ile Arg Gln Gly Pro Lys Glu Pro Phe Arg Asp Tyr Val
770                 775                 780

Asp Arg Phe Tyr Lys Thr Leu Arg Ala Glu Gln Ala Ser Gln Glu Val
785                 790                 795                 800

Lys Asn Trp Met Thr Glu Thr Leu Leu Val Gln Asn Ala Asn Pro Asp
            805                 810                 815

Cys Lys Thr Ile Leu Lys Ala Leu Gly Pro Gly Ala Thr Leu Glu Glu
            820                 825                 830

Met Met Thr Ala Cys Gln Gly Val Gly Gly Pro Ala Ser Met Gly Gly
            835                 840                 845
```

```
Lys Trp Ser Lys Arg Ser Val Val Gly Trp Pro Thr Val Arg Glu Arg
            850                 855                 860
Met Arg Arg Ala Glu Pro Ala Asp Gly Val Gly Ala Val Ser Arg
865                 870                 875                 880
Asp Leu Glu Lys His Gly Ala Ile Thr Ser Ser Asn Thr Ala Ala Asn
                885                 890                 895
Asn Ala Asp Cys Ala Trp Leu Glu Ala Gln Glu Glu Glu Val Gly
            900                 905                 910
Phe Pro Val Arg Pro Gln Val Pro Leu Arg Pro Met Thr Tyr Lys Gly
                915                 920                 925
Ala Leu Asp Leu Ser His Phe Leu Lys Glu Lys Gly Gly Leu Glu Gly
            930                 935                 940
Leu Ile Tyr Ser Gln Lys Arg Gln Asp Ile Leu Asp Leu Trp Val Tyr
945                 950                 955                 960
His Thr Gln Gly Tyr Phe Pro Asp Trp Gln Asn Tyr Thr Pro Gly Pro
                965                 970                 975
Gly Ile Arg Tyr Pro Leu Thr Phe Gly Trp Cys Phe Lys Leu Val Pro
            980                 985                 990
Val Glu Pro Glu Lys Val Glu Glu Ala Asn Glu Gly Glu Asn Asn Ser
                995                 1000                1005
Leu Leu His Pro Met Ser Leu His Gly Met Asp Asp Pro Glu Arg
        1010            1015            1020
Glu Val Leu Val Trp Lys Phe Asp Ser Arg Leu Ala Phe His His
        1025            1030            1035
Met Ala Arg Glu Leu His Pro Gly Tyr Tyr Lys Asp Cys
        1040            1045            1050

<210> SEQ ID NO 12
<211> LENGTH: 1078
<212> TYPE: PRT
<213> ORGANISM: Artificial Sequence
<220> FEATURE:
<223> OTHER INFORMATION: Synthesized Sequence

<400> SEQUENCE: 12

Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Ser Thr Ser
            20                  25                  30
Gly Met Gly Leu Ser Trp Ile Arg Gln Pro Ser Gly Lys Gly Leu Glu
        35                  40                  45
Trp Leu Ala His Ile Tyr Trp Asp Asp Asp Lys Arg Tyr Asn Pro Ser
50                  55                  60
Leu Lys Ser Arg Leu Thr Ile Ser Lys Asp Thr Ser Ser Asn Gln Val
65                  70                  75                  80
Phe Leu Lys Ile Thr Ile Val Asp Thr Ala Asp Ala Thr Tyr Tyr
                85                  90                  95
Cys Ala Arg Ser Ser His Tyr Tyr Gly Tyr Gly Tyr Gly Gly Tyr Phe
            100                 105                 110
Asp Val Trp Gly Ala Gly Thr Thr Val Thr Val Ser Ser Ala Lys Thr
        115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
            165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
            195                 200                 205
Asn Val Asp His Lys Pro Ser Asn Thr Lys Val Asp Lys Arg Val Glu
            210                 215                 220
Ser Lys Tyr Gly Pro Pro Cys Pro Pro Cys Pro Ala Pro Glu Phe Glu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
                260                 265                 270
Gln Glu Asp Pro Glu Val Gln Phe Asn Trp Tyr Val Asp Gly Val Glu
                275                 280                 285
Val His Asn Ala Lys Thr Lys Pro Arg Glu Gln Phe Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
                340                 345                 350
Val Tyr Thr Leu Pro Pro Ser Gln Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
                420                 425                 430
Met His Glu Ala Leu His Asn His Tyr Thr Gln Lys Ser Leu Ser Leu
            435                 440                 445
Ser Leu Gly Lys Ala Ser Gln Thr Pro Thr Asn Thr Ile Ser Val Thr
            450                 455                 460
Pro Thr Asn Asn Ser Thr Pro Thr Asn Asn Ser Asn Pro Lys Pro Asn
465                 470                 475                 480
Pro Ala Ser Leu Glu Met Gly Ala Arg Ala Ser Ile Leu Ser Gly Gly
                485                 490                 495
Glu Leu Asp Arg Trp Glu Lys Ile Arg Leu Arg Pro Gly Gly Lys Lys
                500                 505                 510
Lys Tyr Lys Leu Lys His Ile Val Trp Ala Ser Arg Glu Leu Glu Arg
            515                 520                 525
Phe Ala Val Asn Pro Gly Leu Leu Glu Thr Ser Glu Gly Cys Arg Gln
            530                 535                 540
Ile Leu Gly Gln Leu Gln Pro Ser Leu Gln Thr Gly Ser Glu Glu Leu
545                 550                 555                 560
Arg Ser Leu Tyr Asn Thr Val Ala Thr Leu Tyr Cys Val His Gln Arg
                565                 570                 575
Ile Glu Ile Lys Asp Thr Lys Glu Ala Leu Asp Lys Ile Glu Glu Glu
```

```
                580              585              590
    Gln Asn Lys Ser Val Asp Ser Glu Phe Ala Gln Gln Ala Ala Asp
                    595              600              605
    Thr Gly His Ser Asn Gln Val Ser Gln Asn Tyr Pro Ile Val Gln Asn
        610              615              620
    Ile Gln Gly Gln Met Val His Gln Ala Ile Ser Pro Arg Thr Leu Asn
    625              630              635              640
    Ala Trp Val Lys Val Val Glu Glu Lys Ala Phe Ser Pro Glu Val Ile
                    645              650              655
    Pro Met Phe Ser Ala Leu Ser Glu Gly Ala Thr Pro Gln Asp Leu Asn
                660              665              670
    Thr Met Leu Asn Thr Val Gly Gly His Gln Ala Ala Met Gln Met Leu
                675              680              685
    Lys Glu Thr Ile Asn Glu Glu Ala Ala Glu Trp Asp Arg Val His Pro
    690              695              700
    Val His Ala Gly Pro Ile Ala Pro Gly Gln Met Arg Glu Pro Arg Gly
    705              710              715              720
    Ser Asp Ile Ala Gly Thr Thr Ser Thr Leu Gln Glu Gln Ile Gly Trp
                    725              730              735
    Met Thr His Asn Pro Pro Ile Pro Val Gly Glu Ile Tyr Lys Arg Trp
                740              745              750
    Ile Ile Leu Gly Leu Asn Lys Ile Val Arg Met Tyr Ser Pro Thr Ser
                755              760              765
    Ile Leu Asp Ile Arg Gln Gly Pro Lys Glu Pro Phe Arg Asp Tyr Val
    770              775              780
    Asp Arg Phe Tyr Lys Thr Leu Arg Ala Glu Gln Ala Ser Gln Glu Val
    785              790              795              800
    Lys Asn Trp Met Thr Glu Thr Leu Leu Val Gln Asn Ala Asn Pro Asp
                    805              810              815
    Cys Lys Thr Ile Leu Lys Ala Leu Gly Pro Gly Ala Thr Leu Glu Glu
                820              825              830
    Met Met Thr Ala Cys Gln Gly Val Gly Gly Pro Thr Asn Gly Ser Ile
                835              840              845
    Thr Val Ala Ala Thr Ala Pro Thr Val Thr Pro Thr Val Asn Ala Thr
        850              855              860
    Pro Ser Ala Ala Gly Pro Ala Ser Met Gly Gly Lys Trp Ser Lys Arg
    865              870              875              880
    Ser Val Val Gly Trp Pro Thr Val Arg Glu Arg Met Arg Arg Ala Glu
                    885              890              895
    Pro Ala Ala Asp Gly Val Gly Ala Val Ser Arg Asp Leu Glu Lys His
                900              905              910
    Gly Ala Ile Thr Ser Ser Asn Thr Ala Ala Asn Asn Ala Asp Cys Ala
                915              920              925
    Trp Leu Glu Ala Gln Glu Glu Glu Val Gly Phe Pro Val Arg Pro
        930              935              940
    Gln Val Pro Leu Arg Pro Met Thr Tyr Lys Gly Ala Leu Asp Leu Ser
    945              950              955              960
    His Phe Leu Lys Glu Lys Gly Gly Leu Glu Gly Leu Ile Tyr Ser Gln
                    965              970              975
    Lys Arg Gln Asp Ile Leu Asp Leu Trp Val Tyr His Thr Gln Gly Tyr
                980              985              990
    Phe Pro Asp Trp Gln Asn Tyr Thr  Pro Gly Pro Gly Ile  Arg Tyr Pro
                995              1000              1005
```

```
Leu Thr Phe Gly Trp Cys Phe Lys Leu Val Pro Val Glu Pro Glu
    1010            1015                1020

Lys Val Glu Glu Ala Asn Glu Gly Glu Asn Asn Ser Leu Leu His
    1025            1030                1035

Pro Met Ser Leu His Gly Met Asp Asp Pro Glu Arg Glu Val Leu
    1040            1045                1050

Val Trp Lys Phe Asp Ser Arg Leu Ala Phe His His Met Ala Arg
    1055            1060                1065

Glu Leu His Pro Glu Tyr Tyr Lys Asp Cys
    1070            1075
```

<210> SEQ ID NO 13
<211> LENGTH: 1079
<212> TYPE: PRT
<213> ORGANISM: Artificial Sequence
<220> FEATURE:
<223> OTHER INFORMATION: Synthesized Sequence

<400> SEQUENCE: 13

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Lys Arg Tyr Asn Pro Ser
50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Tyr Phe
            100                 105                 110

Asp Val Trp Gly Ala Gly Thr Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285
```

```
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly Lys Ala Ser Gln Thr Pro Thr Asn Thr Ile Ser Val Thr
    450                 455                 460
Pro Thr Asn Asn Ser Thr Pro Thr Asn Asn Ser Asn Pro Lys Pro Asn
465                 470                 475                 480
Pro Ala Ser Leu Glu Met Gly Ala Arg Ala Ser Ile Leu Ser Gly Gly
                485                 490                 495
Glu Leu Asp Arg Trp Glu Lys Ile Arg Leu Arg Pro Gly Gly Lys Lys
            500                 505                 510
Lys Tyr Lys Leu Lys His Ile Val Trp Ala Ser Arg Glu Leu Glu Arg
        515                 520                 525
Phe Ala Val Asn Pro Gly Leu Leu Glu Thr Ser Glu Gly Cys Arg Gln
    530                 535                 540
Ile Leu Gly Gln Leu Gln Pro Ser Leu Gln Thr Gly Ser Glu Glu Leu
545                 550                 555                 560
Arg Ser Leu Tyr Asn Thr Val Ala Thr Leu Tyr Cys Val His Gln Arg
                565                 570                 575
Ile Glu Ile Lys Asp Thr Lys Glu Ala Leu Asp Lys Ile Glu Glu Glu
            580                 585                 590
Gln Asn Lys Ser Val Asp Met Gly Gly Lys Trp Ser Lys Arg Ser Val
        595                 600                 605
Val Gly Trp Pro Thr Val Arg Glu Arg Met Arg Arg Ala Glu Pro Ala
    610                 615                 620
Ala Asp Gly Val Gly Ala Val Ser Arg Asp Leu Glu Lys His Gly Ala
625                 630                 635                 640
Ile Thr Ser Ser Asn Thr Ala Ala Asn Asn Ala Asp Cys Ala Trp Leu
                645                 650                 655
Glu Ala Gln Glu Glu Glu Glu Val Gly Phe Pro Val Arg Pro Gln Val
            660                 665                 670
Pro Leu Arg Pro Met Thr Tyr Lys Gly Ala Leu Asp Leu Ser His Phe
        675                 680                 685
Leu Lys Glu Lys Gly Gly Leu Glu Gly Leu Ile Tyr Ser Gln Lys Arg
    690                 695                 700
```

```
Gln Asp Ile Leu Asp Leu Trp Val Tyr His Thr Gln Gly Tyr Phe Pro
705                 710                 715                 720

Asp Trp Gln Asn Tyr Thr Pro Gly Pro Gly Ile Arg Tyr Pro Leu Thr
            725                 730                 735

Phe Gly Trp Cys Phe Lys Leu Val Pro Val Glu Pro Glu Lys Val Glu
        740                 745                 750

Glu Ala Asn Glu Gly Glu Asn Asn Ser Leu Leu His Pro Met Ser Leu
    755                 760                 765

His Gly Met Asp Asp Pro Glu Arg Glu Val Leu Val Trp Lys Phe Asp
770                 775                 780

Ser Arg Leu Ala Phe His His Met Ala Arg Glu Leu His Pro Glu Tyr
785                 790                 795                 800

Tyr Lys Asp Cys Glu Phe Thr Asn Gly Ser Ile Thr Val Ala Ala Thr
                805                 810                 815

Ala Pro Thr Val Thr Pro Thr Val Asn Ala Thr Pro Ser Ala Ala Gln
            820                 825                 830

Phe Ala Gln Gln Ala Ala Ala Asp Thr Gly His Ser Asn Gln Val Ser
        835                 840                 845

Gln Asn Tyr Pro Ile Val Gln Asn Ile Gln Gly Gln Met Val His Gln
850                 855                 860

Ala Ile Ser Pro Arg Thr Leu Asn Ala Trp Val Lys Val Glu Glu
865                 870                 875                 880

Lys Ala Phe Ser Pro Glu Val Ile Pro Met Phe Ser Ala Leu Ser Glu
                885                 890                 895

Gly Ala Thr Pro Gln Asp Leu Asn Thr Met Leu Asn Thr Val Gly Gly
            900                 905                 910

His Gln Ala Ala Met Gln Met Leu Lys Glu Thr Ile Asn Glu Glu Ala
        915                 920                 925

Ala Glu Trp Asp Arg Val His Pro Val His Ala Gly Pro Ile Ala Pro
930                 935                 940

Gly Gln Met Arg Glu Pro Arg Gly Ser Asp Ile Ala Gly Thr Thr Ser
945                 950                 955                 960

Thr Leu Gln Glu Gln Ile Gly Trp Met Thr His Asn Pro Pro Ile Pro
                965                 970                 975

Val Gly Glu Ile Tyr Lys Arg Trp Ile Ile Leu Gly Leu Asn Lys Ile
            980                 985                 990

Val Arg Met Tyr Ser Pro Thr Ser Ile Leu Asp Ile Arg Gln Gly Pro
        995                 1000                1005

Lys Glu Pro Phe Arg Asp Tyr Val Asp Arg Phe Tyr Lys Thr Leu
1010                1015                1020

Arg Ala Glu Gln Ala Ser Gln Glu Val Lys Asn Trp Met Thr Glu
1025                1030                1035

Thr Leu Leu Val Gln Asn Ala Asn Pro Asp Cys Lys Thr Ile Leu
1040                1045                1050

Lys Ala Leu Gly Pro Gly Ala Thr Leu Glu Glu Met Met Thr Ala
1055                1060                1065

Cys Gln Gly Val Gly His His His His His
1070                1075

<210> SEQ ID NO 14
<211> LENGTH: 1079
<212> TYPE: PRT
<213> ORGANISM: Artificial Sequence
<220> FEATURE:
<223> OTHER INFORMATION: Synthesized Sequence
```

<400> SEQUENCE: 14

```
Gln Val Thr Leu Lys Glu Ser Gly Pro Gly Ile Leu Gln Pro Ser Gln
  1               5                  10                  15

Thr Leu Ser Leu Thr Cys Ser Phe Ser Gly Phe Ser Leu Ser Thr Ser
             20                  25                  30

Gly Met Gly Leu Ser Trp Ile Arg Gln Pro Ser Gly Lys Gly Leu Glu
         35                  40                  45

Trp Leu Ala His Ile Tyr Trp Asp Asp Lys Arg Tyr Asn Pro Ser
     50                  55                  60

Leu Lys Ser Arg Leu Thr Ile Ser Lys Asp Thr Ser Ser Asn Gln Val
 65                  70                  75                  80

Phe Leu Lys Ile Thr Ile Val Asp Thr Ala Asp Ala Thr Tyr Tyr
                 85                  90                  95

Cys Ala Arg Ser Ser His Tyr Tyr Gly Tyr Gly Tyr Gly Gly Tyr Phe
            100                 105                 110

Asp Val Trp Gly Ala Gly Thr Thr Val Thr Val Ser Ser Ala Lys Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
```

```
                405                 410                 415
Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Leu Glu Met Gly Ala Arg Ala Ser Ile Leu Ser Gly Gly
                485                 490                 495

Glu Leu Asp Arg Trp Glu Lys Ile Arg Leu Arg Pro Gly Gly Lys Lys
            500                 505                 510

Lys Tyr Lys Leu Lys His Ile Val Trp Ala Ser Arg Glu Leu Glu Arg
        515                 520                 525

Phe Ala Val Asn Pro Gly Leu Leu Glu Thr Ser Glu Gly Cys Arg Gln
530                 535                 540

Ile Leu Gly Gln Leu Gln Pro Ser Leu Gln Thr Gly Ser Glu Glu Leu
545                 550                 555                 560

Arg Ser Leu Tyr Asn Thr Val Ala Thr Leu Tyr Cys Val His Gln Arg
                565                 570                 575

Ile Glu Ile Lys Asp Thr Lys Glu Ala Leu Asp Lys Ile Glu Glu Glu
            580                 585                 590

Gln Asn Lys Ser Val Asp Thr Val Thr Pro Thr Ala Thr Ala Thr Pro
        595                 600                 605

Ser Ala Ile Val Thr Thr Ile Thr Pro Thr Ala Thr Thr Lys Pro Val
610                 615                 620

Asp Met Gly Gly Lys Trp Ser Lys Arg Ser Val Val Gly Trp Pro Thr
625                 630                 635                 640

Val Arg Glu Arg Met Arg Arg Ala Glu Pro Ala Ala Asp Gly Val Gly
                645                 650                 655

Ala Val Ser Arg Asp Leu Glu Lys His Gly Ala Ile Thr Ser Ser Asn
            660                 665                 670

Thr Ala Ala Asn Asn Ala Asp Cys Ala Trp Leu Glu Ala Gln Glu Glu
        675                 680                 685

Glu Glu Val Gly Phe Pro Val Arg Pro Gln Val Pro Leu Arg Pro Met
690                 695                 700

Thr Tyr Lys Gly Ala Leu Asp Leu Ser His Phe Leu Lys Glu Lys Gly
705                 710                 715                 720

Gly Leu Glu Gly Leu Ile Tyr Ser Gln Lys Arg Gln Asp Ile Leu Asp
                725                 730                 735

Leu Trp Val Tyr His Thr Gln Gly Tyr Phe Pro Asp Trp Gln Asn Tyr
            740                 745                 750

Thr Pro Gly Pro Gly Ile Arg Tyr Pro Leu Thr Phe Gly Trp Cys Phe
        755                 760                 765

Lys Leu Val Pro Val Glu Pro Glu Lys Val Glu Glu Ala Asn Glu Gly
770                 775                 780

Glu Asn Asn Ser Leu Leu His Pro Met Ser Leu His Gly Met Asp Asp
785                 790                 795                 800

Pro Glu Arg Glu Val Leu Val Trp Lys Phe Asp Ser Arg Leu Ala Phe
                805                 810                 815

His His Met Ala Arg Glu Leu His Pro Glu Tyr Tyr Lys Asp Cys Glu
            820                 825                 830
```

```
Phe Ala Gln Gln Ala Ala Ala Asp Thr Gly His Ser Asn Gln Val Ser
            835                 840                 845

Gln Asn Tyr Pro Ile Val Gln Asn Ile Gln Gly Gln Met Val His Gln
    850                 855                 860

Ala Ile Ser Pro Arg Thr Leu Asn Ala Trp Val Lys Val Val Glu Glu
865                 870                 875                 880

Lys Ala Phe Ser Pro Glu Val Ile Pro Met Phe Ser Ala Leu Ser Glu
                885                 890                 895

Gly Ala Thr Pro Gln Asp Leu Asn Thr Met Leu Asn Thr Val Gly Gly
                900                 905                 910

His Gln Ala Ala Met Gln Met Leu Lys Glu Thr Ile Asn Glu Glu Ala
            915                 920                 925

Ala Glu Trp Asp Arg Val His Pro Val His Ala Gly Pro Ile Ala Pro
    930                 935                 940

Gly Gln Met Arg Glu Pro Arg Gly Ser Asp Ile Ala Gly Thr Thr Ser
945                 950                 955                 960

Thr Leu Gln Glu Gln Ile Gly Trp Met Thr His Asn Pro Pro Ile Pro
                965                 970                 975

Val Gly Glu Ile Tyr Lys Arg Trp Ile Ile Leu Gly Leu Asn Lys Ile
                980                 985                 990

Val Arg Met Tyr Ser Pro Thr Ser Ile Leu Asp Ile Arg Gln Gly Pro
    995                 1000                1005

Lys Glu Pro Phe Arg Asp Tyr Val Asp Arg Phe Tyr Lys Thr Leu
    1010                1015                1020

Arg Ala Glu Gln Ala Ser Gln Glu Val Lys Asn Trp Met Thr Glu
    1025                1030                1035

Thr Leu Leu Val Gln Asn Ala Asn Pro Asp Cys Lys Thr Ile Leu
    1040                1045                1050

Lys Ala Leu Gly Pro Gly Ala Thr Leu Glu Glu Met Met Thr Ala
    1055                1060                1065

Cys Gln Gly Val Gly His His His His His His
    1070                1075

<210> SEQ ID NO 15
<211> LENGTH: 1106
<212> TYPE: PRT
<213> ORGANISM: Artificial Sequence
<220> FEATURE:
<223> OTHER INFORMATION: Synthesized Sequence

<400> SEQUENCE: 15

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Leu Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Ser Asn Gln Val
65                  70                  75                  80

Phe Leu Lys Ile Thr Ile Val Asp Thr Ala Asp Ala Thr Tyr Tyr
                85                  90                  95

Cys Ala Arg Ser Ser His Tyr Tyr Gly Tyr Gly Tyr Gly Gly Tyr Phe
                100                 105                 110
```

```
Asp Val Trp Gly Ala Gly Thr Val Thr Val Ser Ser Ala Lys Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                    165                 170                 175

Thr Phe Pro Ala Val Leu Gln Ser Ser Gly Leu Tyr Ser Leu Ser Ser
                180                 185                 190

Val Val Thr Val Pro Ser Ser Leu Gly Thr Lys Thr Tyr Thr Cys
            195                 200                 205

Asn Val Asp His Lys Pro Ser Asn Thr Lys Val Asp Lys Arg Val Glu
            210                 215                 220

Ser Lys Tyr Gly Pro Pro Cys Pro Pro Cys Pro Ala Pro Glu Phe Glu
225                 230                 235                 240

Gly Gly Pro Ser Val Phe Leu Phe Pro Pro Lys Pro Lys Asp Thr Leu
                    245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
    355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
    435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Leu Glu Met Gly Ala Arg Ala Ser Ile Leu Ser Gly Gly
                485                 490                 495

Glu Leu Asp Arg Trp Glu Lys Ile Arg Leu Arg Pro Gly Gly Lys Lys
            500                 505                 510

Lys Tyr Lys Leu Lys His Ile Val Trp Ala Ser Arg Glu Leu Glu Arg
    515                 520                 525
```

```
Phe Ala Val Asn Pro Gly Leu Leu Glu Thr Ser Glu Gly Cys Arg Gln
    530                 535                 540

Ile Leu Gly Gln Leu Gln Pro Ser Leu Gln Thr Gly Ser Glu Leu
545                 550                 555                 560

Arg Ser Leu Tyr Asn Thr Val Ala Thr Leu Tyr Cys Val His Gln Arg
                565                 570                 575

Ile Glu Ile Lys Asp Thr Lys Glu Ala Leu Asp Lys Ile Glu Glu Glu
            580                 585                 590

Gln Asn Lys Ser Val Asp Thr Val Thr Pro Thr Ala Thr Ala Thr Pro
        595                 600                 605

Ser Ala Ile Val Thr Thr Ile Thr Pro Thr Ala Thr Thr Lys Pro Val
610                 615                 620

Asp Met Gly Gly Lys Trp Ser Lys Arg Ser Val Val Gly Trp Pro Thr
625                 630                 635                 640

Val Arg Glu Arg Met Arg Ala Glu Pro Ala Ala Asp Gly Val Gly
                645                 650                 655

Ala Val Ser Arg Asp Leu Glu Lys His Gly Ala Ile Thr Ser Ser Asn
                660                 665                 670

Thr Ala Ala Asn Asn Ala Asp Cys Ala Trp Leu Glu Ala Gln Glu Glu
            675                 680                 685

Glu Glu Val Gly Phe Pro Val Arg Pro Gln Val Pro Leu Arg Pro Met
    690                 695                 700

Thr Tyr Lys Gly Ala Leu Asp Leu Ser His Phe Leu Lys Glu Lys Gly
705                 710                 715                 720

Gly Leu Glu Gly Leu Ile Tyr Ser Gln Lys Arg Gln Asp Ile Leu Asp
                725                 730                 735

Leu Trp Val Tyr His Thr Gln Gly Tyr Phe Pro Asp Trp Gln Asn Tyr
                740                 745                 750

Thr Pro Gly Pro Gly Ile Arg Tyr Pro Leu Thr Phe Gly Trp Cys Phe
            755                 760                 765

Lys Leu Val Pro Val Glu Pro Lys Val Glu Ala Asn Glu Gly
    770                 775                 780

Glu Asn Asn Ser Leu Leu His Pro Met Ser Leu His Gly Met Asp Asp
785                 790                 795                 800

Pro Glu Arg Glu Val Leu Val Trp Lys Phe Asp Ser Arg Leu Ala Phe
                805                 810                 815

His His Met Ala Arg Glu Leu His Pro Glu Tyr Tyr Lys Asp Cys Glu
            820                 825                 830

Phe Thr Asn Gly Ser Ile Thr Val Ala Ala Thr Ala Pro Thr Val Thr
    835                 840                 845

Pro Thr Val Asn Ala Thr Pro Ser Ala Ala Gln Phe Ala Gln Ala
850                 855                 860

Ala Ala Asp Thr Gly His Ser Asn Gln Val Ser Gln Asn Tyr Pro Ile
865                 870                 875                 880

Val Gln Asn Ile Gln Gly Gln Met Val His Gln Ala Ile Ser Pro Arg
                885                 890                 895

Thr Leu Asn Ala Trp Val Lys Val Val Glu Glu Lys Ala Phe Ser Pro
            900                 905                 910

Glu Val Ile Pro Met Phe Ser Ala Leu Ser Glu Gly Ala Thr Pro Gln
    915                 920                 925

Asp Leu Asn Thr Met Leu Asn Thr Val Gly Gly His Gln Ala Ala Met
930                 935                 940

Gln Met Leu Lys Glu Thr Ile Asn Glu Glu Ala Ala Glu Trp Asp Arg
```

```
945                 950                 955                 960
Val His Pro Val His Ala Gly Pro Ile Ala Pro Gly Gln Met Arg Glu
                965                 970                 975
Pro Arg Gly Ser Asp Ile Ala Gly Thr Thr Ser Thr Leu Gln Glu Gln
                    980                 985                 990
Ile Gly Trp Met Thr His Asn Pro Pro Ile Pro Val Gly Glu Ile Tyr
        995                 1000                1005
Lys Arg Trp Ile Ile Leu Gly Leu Asn Lys Ile Val Arg Met Tyr
    1010                1015                1020
Ser Pro Thr Ser Ile Leu Asp Ile Arg Gln Gly Pro Lys Glu Pro
    1025                1030                1035
Phe Arg Asp Tyr Val Asp Arg Phe Tyr Lys Thr Leu Arg Ala Glu
    1040                1045                1050
Gln Ala Ser Gln Glu Val Lys Asn Trp Met Thr Glu Thr Leu Leu
    1055                1060                1065
Val Gln Asn Ala Asn Pro Asp Cys Lys Thr Ile Leu Lys Ala Leu
    1070                1075                1080
Gly Pro Gly Ala Thr Leu Glu Glu Met Met Thr Ala Cys Gln Gly
    1085                1090                1095
Val Gly His His His His His His
    1100                1105

<210> SEQ ID NO 16
<211> LENGTH: 1106
<212> TYPE: PRT
<213> ORGANISM: Artificial Sequence
<220> FEATURE:
<223> OTHER INFORMATION: Synthesized Sequence

<400> SEQUENCE: 16

Gln Val Thr Leu Lys Glu Ser Gly Pro Gly Ile Leu Gln Pro Ser Gln
1               5                   10                  15
Thr Leu Ser Leu Thr Cys Ser Phe Ser Gly Phe Ser Leu Ser Thr Ser
            20                  25                  30
Gly Met Gly Leu Ser Trp Ile Arg Gln Pro Ser Gly Lys Gly Leu Glu
        35                  40                  45
Trp Leu Ala His Ile Tyr Trp Asp Asp Asp Lys Arg Tyr Asn Pro Ser
    50                  55                  60
Leu Lys Ser Arg Leu Thr Ile Ser Lys Asp Thr Ser Ser Asn Gln Val
65                  70                  75                  80
Phe Leu Lys Ile Thr Ile Val Asp Thr Ala Asp Ala Ala Thr Tyr Tyr
                85                  90                  95
Cys Ala Arg Ser Ser His Tyr Tyr Gly Tyr Gly Tyr Gly Tyr Phe
            100                 105                 110
Asp Val Trp Gly Ala Gly Thr Thr Val Thr Val Ser Ser Ala Lys Thr
        115                 120                 125
Lys Gly Pro Ser Val Phe Pro Leu Ala Pro Cys Ser Arg Ser Thr Ser
    130                 135                 140
Glu Ser Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
                180                 185                 190
Val Val Thr Val Pro Ser Ser Ser Leu Gly Thr Lys Thr Tyr Thr Cys
```

```
                195                 200                 205
Asn Val Asp His Lys Pro Ser Asn Thr Lys Val Asp Lys Arg Val Glu
210                 215                 220

Ser Lys Tyr Gly Pro Pro Cys Pro Cys Pro Ala Pro Glu Phe Glu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Ala Ser Gln Thr Pro Thr Asn Thr Ile Ser Val Thr
450                 455                 460

Pro Thr Asn Asn Ser Thr Pro Thr Asn Asn Ser Asn Pro Lys Pro Asn
465                 470                 475                 480

Pro Ala Ser Leu Glu Met Gly Ala Arg Ala Ser Ile Leu Ser Gly Gly
                485                 490                 495

Glu Leu Asp Arg Trp Glu Lys Ile Arg Leu Arg Pro Gly Gly Asn Lys
            500                 505                 510

Gln Tyr Lys Leu Lys His Ile Val Trp Ala Ser Arg Glu Leu Glu Arg
        515                 520                 525

Phe Ala Val Asn Pro Gly Leu Leu Glu Thr Ser Glu Gly Cys Arg Gln
530                 535                 540

Ile Leu Gly Gln Leu Gln Pro Ser Leu Gln Thr Gly Ser Glu Glu Leu
545                 550                 555                 560

Arg Ser Leu Tyr Asn Thr Val Ala Thr Leu Tyr Cys Val His Gln Arg
                565                 570                 575

Ile Glu Ile Lys Asp Thr Lys Glu Ala Leu Asp Lys Ile Glu Glu Glu
            580                 585                 590

Gln Asn Lys Ser Val Asp Thr Val Thr Pro Thr Ala Thr Ala Thr Pro
        595                 600                 605

Ser Ala Ile Val Thr Thr Ile Thr Pro Thr Ala Thr Thr Lys Pro Val
610                 615                 620
```

```
Asp Met Gly Gly Lys Trp Ser Lys Arg Ser Val Val Gly Trp Pro Thr
625                 630                 635                 640

Val Arg Glu Arg Met Arg Ala Glu Pro Ala Ala Asp Gly Val Gly
                645                 650                 655

Ala Val Ser Arg Asp Leu Glu Lys His Gly Ala Ile Thr Ser Ser Asn
            660                 665                 670

Thr Ala Ala Asn Asn Ala Asp Cys Ala Trp Leu Glu Ala Gln Glu Glu
            675                 680                 685

Glu Glu Val Gly Phe Pro Val Arg Pro Gln Val Pro Leu Arg Pro Met
690                 695                 700

Thr Tyr Lys Gly Ala Leu Asp Leu Ser His Phe Leu Lys Glu Lys Gly
705                 710                 715                 720

Gly Leu Glu Gly Leu Ile Tyr Ser Gln Lys Arg Gln Asp Ile Leu Asp
                725                 730                 735

Leu Trp Val Tyr His Thr Gln Gly Tyr Phe Pro Asp Trp Gln Asn Tyr
            740                 745                 750

Thr Pro Gly Pro Gly Ile Arg Tyr Pro Leu Thr Phe Gly Trp Cys Phe
            755                 760                 765

Lys Leu Val Pro Val Glu Pro Glu Lys Val Glu Glu Ala Asn Glu Gly
770                 775                 780

Glu Asn Asn Ser Leu Leu His Pro Met Ser Leu His Gly Met Asp Asp
785                 790                 795                 800

Pro Glu Arg Glu Val Leu Val Trp Lys Phe Asp Ser Arg Leu Ala Phe
                805                 810                 815

His His Met Ala Arg Glu Leu His Pro Glu Tyr Tyr Lys Asp Cys Glu
            820                 825                 830

Phe Thr Asn Gly Ser Ile Thr Val Ala Ala Thr Ala Pro Thr Val Thr
            835                 840                 845

Pro Thr Val Asn Ala Thr Pro Ser Ala Ala Gln Phe Ala Gln Gln Ala
850                 855                 860

Ala Ala Asp Thr Gly His Ser Asn Gln Val Ser Gln Asn Tyr Pro Ile
865                 870                 875                 880

Val Gln Asn Ile Gln Gly Gln Met Val His Gln Ala Ile Ser Pro Arg
                885                 890                 895

Thr Leu Asn Ala Trp Val Lys Val Val Glu Glu Lys Ala Phe Ser Pro
            900                 905                 910

Glu Val Ile Pro Met Phe Ser Ala Leu Ser Glu Gly Ala Thr Pro Gln
            915                 920                 925

Asp Leu Asn Thr Met Leu Asn Thr Val Gly Gly His Gln Ala Ala Met
930                 935                 940

Gln Met Leu Lys Glu Thr Ile Asn Glu Glu Ala Ala Glu Trp Asp Arg
945                 950                 955                 960

Val His Pro Val His Ala Gly Pro Ile Ala Pro Gly Gln Met Arg Glu
                965                 970                 975

Pro Arg Gly Ser Asp Ile Ala Gly Thr Thr Ser Thr Leu Gln Glu Gln
            980                 985                 990

Ile Gly Trp Met Thr His Asn Pro Pro Ile Pro Val Gly Glu Ile Tyr
            995                 1000                1005

Lys Arg Trp Ile Ile Leu Gly Leu Asn Lys Ile Val Arg Met Tyr
        1010            1015            1020

Ser Pro Thr Ser Ile Leu Asp Ile Arg Gln Gly Pro Lys Glu Pro
        1025            1030            1035
```

```
Phe Arg Asp Tyr Val Asp Arg Phe Tyr Lys Thr Leu Arg Ala Glu
    1040                1045                1050

Gln Ala Ser Gln Glu Val Lys Asn Trp Met Thr Glu Thr Leu Leu
    1055                1060                1065

Val Gln Asn Ala Asn Pro Asp Cys Lys Thr Ile Leu Lys Ala Leu
    1070                1075                1080

Gly Pro Gly Ala Thr Leu Glu Glu Met Met Thr Ala Cys Gln Gly
    1085                1090                1095

Val Gly His His His His His His
    1100                1105
```

```
<210> SEQ ID NO 17
<211> LENGTH: 627
<212> TYPE: DNA
<213> ORGANISM: Artificial Sequence
<220> FEATURE:
<223> OTHER INFORMATION: Synthetic Oligonucleotide

<400> SEQUENCE: 17
gctagcatgg gaggcaaatg gagtaaaaga agtgttgtgg gttggccaac tgtgagagaa      60
agaatgagaa gggctgaacc agccgctgat ggtgtaggtg ctgtgtcacg agatctggaa     120
aaacacggag caataacatc ctctaatacc gccgcaaata cgcagactg tgcctggctc      180 gaagctcaag aagaagaaga agtcggattc cccgtgcgac cccaagttcc cctcagacca     240
atgacttata aaggcgctct ggatcttagc cactttctta agaaaaagg aggactggaa      300 ggacttattt attcacaaaa aagacaagac atcctcgatt tgtgggtata tcatactcaa     360
ggttatttcc cagactggca aaattatact cctggacccg gcattcgata tccccttacc    420
tttggatggt gctttaaact tgtccccgtc gaacctgaaa aagtagaaga agcaaatgaa     480
ggcgaaaata attcactgct ccaccctatg tcactgcacg gaatggatga ccccgaacgc    540
gaagttctgg tatggaaatt tgattcaaga cttgcttttc accacatggc tagagaactt     600 cacccgaat attataaaga ctgttga                                           627
```

```
<210> SEQ ID NO 18
<211> LENGTH: 1965
<212> TYPE: DNA
<213> ORGANISM: Artificial Sequence
<220> FEATURE:
<223> OTHER INFORMATION: Synthetic Oligonucleotide

<400> SEQUENCE: 18
gctagtcaga cccccaccaa caccatcagc gtgacccca ccaacaacag cacccccacc        60
aacaacagca accccaagcc caaccccgct agcctcgaga tgggtgcgag agcgtcaata     120
ttaagcggtg gcgaattaga tagatgggaa aaaattcggt taaggccagg gggaaagaaa     180
aaatataaat taaaacatat agtatgggca agcagggagc tagaacgatt cgcagttaat     240
cctggcctgt tagaaacatc agaaggctgt agacaaatac tgggacagct acaaccatcc     300
cttcagacag gatcagaaga acttagatca ttatataata cagtagcaac cctctattgt     360
gtgcatcaaa ggatagagat aaaagacacc aaggaagctt tagacaagat agaggaagag     420
caaaacaaaa gtgtcgatac cgtgaccccc accgccaccg ccaccccag cgccatcgtg     480 accaccatca cccccaccgc caccaccaag cccgtcgaca tgggaggcaa atggagtaaa     540
agaagtgttg tgggttggcc aactgtgaga gaaagaatga aagggctga accagccgct    600 gatggtgtag gtgctgtgtc acgagatctg gaaaaacacg gagcaataac atcctctaat   660
```

```
accgccgcaa ataacgcaga ctgtgcctgg ctcgaagctc aagaagaaga agaagtcgga    720
ttccccgtgc gaccccaagt tcccctcaga ccaatgactt ataaaggcgc tctggatctt    780
agccactttc ttaaagaaaa aggaggactg gaaggactta tttattcaca aaaaagacaa    840
gacatcctcg atttgtgggt atatcatact caaggttatt tcccagactg gcaaaattat    900
actcctggac ccggcattcg atatcccctt acctttggat ggtgctttaa acttgtcccc    960
gtcgaacctg aaaaagtaga agaagcaaat gaaggcgaaa ataattcact gctccaccct   1020
atgtcactgc acggaatgga tgaccccgaa cgcgaagttc tggtatggaa atttgattca   1080
agacttgctt ttcaccacat ggctagagaa cttcaccccg aatattataa agactgtgaa   1140
ttcaccaacg gcagcatcac cgtggccgcc accgccccca ccgtgacccc caccgtgaac   1200
gccaccccca gcgccgccca attcgcacag caagcagcag ctgacacagg acacagcaat   1260
caggtcagcc aaaattaccc tatagtgcag aacatccagg ggcaaatggt acatcaggcc   1320
atatcaccta gaactttaaa tgcatgggta aaagtagtag aagagaaggc tttcagccca   1380
gaagtgatac ccatgttttc agcattatca gaaggagcca ccccacaaga tttaaacacc   1440
atgctaaaca cagtgggggg acatcaagca gccatgcaaa tgttaaaaga gaccatcaat   1500
gaggaagctg cagaatggga tagagtgcat ccagtgcatg cagggcctat tgcaccaggc   1560
cagatgagag aaccaagggg aagtgacata gcaggaacta ctagtaccct tcaggaacaa   1620
ataggatgga tgacacataa tccacctatc ccagtaggag aaatctataa aaggtggata   1680
atcctgggat taaataaaat agtaagaatg tatagcccta ccagcattct ggacataaga   1740
caaggaccaa aggaaccctt tagagactat gtagaccgat tctataaaac tctaagagcc   1800
gagcaagctt cacaagaggt aaaaaattgg atgacagaaa ccttgttggt ccaaaatgcg   1860
aacccagatt gtaagactat ttaaaagca ttgggaccag gagcgacact agaagaaatg   1920
atgacagcat gtcagggagt ggggcatcac catcaccatc actga                   1965
```

<210> SEQ ID NO 19
<211> LENGTH: 919
<212> TYPE: PRT
<213> ORGANISM: Artificial Sequence
<220> FEATURE:
<223> OTHER INFORMATION: Synthetic Oligonucleotide

<400> SEQUENCE: 19

```
Ala Thr Gly Ala Thr Gly Thr Cys Cys Thr Cys Thr Gly Cys Thr Cys
1               5                   10                  15

Ala Gly Thr Thr Cys Cys Thr Thr Gly Gly Thr Cys Thr Cys Cys Thr
            20                  25                  30

Gly Thr Thr Gly Cys Thr Cys Thr Gly Thr Thr Thr Thr Cys Ala Ala
        35                  40                  45

Gly Gly Thr Ala Cys Cys Ala Gly Ala Thr Gly Thr Gly Ala Thr Ala
    50                  55                  60

Thr Cys Cys Ala Gly Ala Thr Gly Ala Cys Ala Cys Ala Gly Ala Cys
65                  70                  75                  80

Thr Ala Cys Ala Thr Cys Cys Thr Cys Cys Cys Thr Gly Thr Cys Thr
                85                  90                  95

Gly Cys Cys Thr Cys Thr Cys Thr Ala Gly Gly Ala Gly Ala Cys Ala
            100                 105                 110

Gly Ala Gly Thr Cys Ala Cys Cys Ala Thr Cys Ala Gly Thr Thr Gly
        115                 120                 125

Cys Ala Gly Thr Gly Cys Ala Ala Gly Thr Cys Ala Gly Gly Gly Cys
```

-continued

```
    130                 135                 140

Ala Thr Thr Ala Gly Cys Ala Ala Thr Thr Ala Thr Thr Thr Ala Ala
145                 150                 155                 160

Ala Cys Thr Gly Gly Thr Ala Thr Cys Ala Gly Cys Ala Gly Ala Ala
                165                 170                 175

Ala Cys Cys Ala Gly Ala Thr Gly Gly Ala Ala Cys Thr Gly Thr Thr
            180                 185                 190

Ala Ala Ala Cys Thr Cys Cys Thr Gly Ala Thr Cys Thr Ala Thr Thr
        195                 200                 205

Ala Cys Ala Cys Ala Thr Cys Ala Ala Thr Thr Thr Thr Ala Cys Ala
    210                 215                 220

Cys Thr Cys Ala Gly Gly Ala Gly Thr Cys Cys Cys Ala Thr Cys Ala
225                 230                 235                 240

Ala Gly Gly Thr Thr Cys Ala Gly Thr Gly Gly Cys Ala Gly Thr Gly
                245                 250                 255

Gly Gly Thr Cys Thr Gly Gly Gly Ala Cys Ala Gly Ala Thr Thr Ala
            260                 265                 270

Thr Thr Cys Thr Cys Thr Cys Ala Cys Cys Ala Thr Cys Gly Gly Cys
        275                 280                 285

Ala Ala Cys Cys Thr Gly Gly Ala Ala Cys Cys Thr Gly Ala Ala Gly
    290                 295                 300

Ala Thr Ala Thr Thr Gly Cys Cys Ala Cys Thr Thr Ala Cys Thr Ala
305                 310                 315                 320

Thr Thr Gly Thr Cys Ala Gly Cys Ala Gly Thr Thr Thr Ala Ala Thr
                325                 330                 335

Ala Ala Gly Cys Thr Thr Cys Cys Thr Cys Cys Gly Ala Cys Gly Thr
            340                 345                 350

Thr Cys Gly Gly Thr Gly Gly Ala Gly Gly Cys Ala Cys Cys Ala Ala
        355                 360                 365

Ala Cys Thr Cys Gly Ala Gly Ala Thr Cys Ala Ala Ala Cys Gly Ala
    370                 375                 380

Ala Cys Thr Gly Thr Gly Gly Cys Thr Gly Cys Ala Cys Cys Ala Thr
385                 390                 395                 400

Cys Thr Gly Thr Cys Thr Thr Cys Ala Thr Cys Thr Thr Cys Cys Cys
                405                 410                 415

Gly Cys Cys Ala Thr Cys Thr Gly Ala Thr Gly Ala Gly Cys Ala Gly
            420                 425                 430

Thr Thr Gly Ala Ala Ala Thr Cys Thr Gly Gly Ala Ala Cys Thr Gly
        435                 440                 445

Cys Cys Thr Cys Thr Gly Thr Thr Gly Thr Gly Thr Gly Cys Cys Thr
    450                 455                 460

Gly Cys Thr Gly Ala Ala Thr Ala Ala Cys Thr Thr Cys Thr Ala Thr
465                 470                 475                 480

Cys Cys Cys Ala Gly Ala Gly Ala Gly Gly Cys Cys Ala Ala Ala Gly
                485                 490                 495

Thr Ala Cys Ala Gly Thr Gly Gly Ala Ala Gly Gly Thr Gly Gly Ala
            500                 505                 510

Thr Ala Ala Cys Gly Cys Cys Cys Thr Cys Cys Ala Ala Thr Cys Gly
        515                 520                 525

Gly Gly Thr Ala Ala Cys Thr Cys Cys Cys Ala Gly Gly Ala Gly Ala
    530                 535                 540

Gly Thr Gly Thr Cys Ala Cys Ala Gly Ala Gly Cys Ala Gly Gly Ala
545                 550                 555                 560
```

Cys Ala Gly Cys Ala Ala Gly Ala Cys Ala Gly Cys Cys
                565                 570                 575

Thr Ala Cys Ala Gly Cys Cys Thr Cys Ala Gly Cys Ala Gly Cys Ala
                580                 585                 590

Cys Cys Cys Thr Gly Ala Cys Gly Cys Thr Gly Ala Gly Cys Ala Ala
                595                 600                 605

Ala Gly Cys Ala Gly Ala Cys Thr Ala Cys Gly Ala Gly Ala Ala Ala
            610                 615                 620

Cys Ala Cys Ala Ala Gly Thr Cys Thr Ala Thr Gly Cys Cys Thr
625                 630                 635                 640

Gly Cys Gly Ala Ala Gly Thr Cys Ala Cys Cys Ala Thr Cys Ala
                645                 650                 655

Gly Gly Gly Cys Cys Thr Gly Ala Gly Cys Thr Cys Gly Cys Cys Cys
                660                 665                 670

Gly Thr Cys Ala Cys Ala Ala Gly Ala Gly Cys Thr Thr Cys Ala
                675                 680                 685

Ala Cys Ala Gly Gly Gly Ala Gly Ala Gly Thr Gly Thr Thr Ala
        690                 695                 700

Gly Asp Ile Gln Met Thr Gln Thr Thr Ser Ser Leu Ser Ala Ser Leu
705                 710                 715                 720

Gly Asp Arg Val Thr Ile Ser Cys Ser Ala Ser Gln Gly Ile Ser Asn
                725                 730                 735

Tyr Leu Asn Trp Tyr Gln Gln Lys Pro Asp Gly Thr Val Lys Leu Leu
                740                 745                 750

Ile Tyr Tyr Thr Ser Ile Leu His Ser Gly Val Pro Ser Arg Phe Ser
                755                 760                 765

Gly Ser Gly Ser Gly Thr Asp Tyr Ser Leu Thr Ile Gly Asn Leu Glu
        770                 775                 780

Pro Glu Asp Ile Ala Thr Tyr Tyr Cys Gln Gln Phe Asn Lys Leu Pro
785                 790                 795                 800

Pro Thr Phe Gly Gly Gly Thr Lys Leu Glu Ile Lys Arg Thr Val Ala
                805                 810                 815

Ala Pro Ser Val Phe Ile Phe Pro Pro Ser Asp Glu Gln Leu Lys Ser
                820                 825                 830

Gly Thr Ala Ser Val Val Cys Leu Leu Asn Asn Phe Tyr Pro Arg Glu
        835                 840                 845

Ala Lys Val Gln Trp Lys Val Asp Asn Ala Leu Gln Ser Gly Asn Ser
    850                 855                 860

Gln Glu Ser Val Thr Glu Gln Asp Ser Lys Asp Ser Thr Tyr Ser Leu
865                 870                 875                 880

Ser Ser Thr Leu Thr Leu Ser Lys Ala Asp Tyr Glu Lys His Lys Val
                885                 890                 895

Tyr Ala Cys Glu Val Thr His Gln Gly Leu Ser Ser Pro Val Thr Lys
                900                 905                 910

Ser Phe Asn Arg Gly Glu Cys
        915

<210> SEQ ID NO 20
<211> LENGTH: 1852
<212> TYPE: PRT
<213> ORGANISM: Artificial Sequence
<220> FEATURE:
<223> OTHER INFORMATION: Synthetic Oligonucleotide

<400> SEQUENCE: 20

```
Ala Thr Gly Ala Ala Cys Thr Thr Gly Gly Gly Gly Cys Thr Cys Ala
1               5                   10                  15

Gly Cys Thr Thr Gly Ala Thr Thr Thr Thr Cys Cys Thr Thr Gly Thr
            20                  25                  30

Cys Cys Thr Thr Gly Thr Thr Thr Thr Ala Ala Ala Ala Gly Gly Thr
        35                  40                  45

Gly Thr Cys Cys Ala Gly Thr Gly Thr Gly Ala Ala Gly Thr Gly Ala
    50                  55                  60

Ala Gly Cys Thr Gly Gly Thr Gly Gly Ala Gly Thr Cys Thr Gly Gly
65                  70                  75                  80

Gly Gly Gly Ala Gly Gly Cys Thr Thr Ala Gly Thr Gly Cys Ala Gly
                85                  90                  95

Cys Cys Thr Gly Gly Ala Gly Gly Gly Thr Cys Cys Cys Thr Gly Ala
            100                 105                 110

Ala Ala Cys Thr Cys Thr Cys Cys Thr Gly Thr Gly Cys Ala Ala Cys
        115                 120                 125

Cys Thr Cys Thr Gly Gly Ala Thr Thr Cys Ala Cys Thr Thr Thr Cys
    130                 135                 140

Ala Gly Thr Gly Ala Cys Thr Ala Thr Thr Ala Cys Ala Thr Gly Thr
145                 150                 155                 160

Ala Thr Thr Gly Gly Gly Thr Thr Cys Gly Cys Cys Ala Gly Ala Cys
                165                 170                 175

Thr Cys Cys Ala Gly Ala Gly Ala Ala Gly Ala Gly Gly Cys Thr Gly
            180                 185                 190

Gly Ala Gly Thr Gly Gly Gly Thr Cys Gly Cys Ala Thr Ala Cys Ala
        195                 200                 205

Thr Thr Ala Ala Thr Thr Cys Thr Gly Gly Thr Gly Gly Thr Gly Gly
    210                 215                 220

Thr Ala Gly Cys Ala Cys Cys Thr Ala Thr Thr Ala Thr Cys Cys Ala
225                 230                 235                 240

Gly Ala Cys Ala Cys Thr Gly Thr Ala Ala Ala Gly Gly Gly Cys Cys
                245                 250                 255

Gly Ala Thr Thr Cys Ala Cys Cys Ala Thr Cys Thr Cys Cys Ala Gly
            260                 265                 270

Ala Gly Ala Cys Ala Ala Thr Gly Cys Cys Ala Ala Gly Ala Ala Cys
        275                 280                 285

Ala Cys Cys Cys Thr Gly Thr Ala Cys Cys Thr Gly Cys Ala Ala Ala
    290                 295                 300

Thr Gly Ala Gly Cys Cys Gly Gly Cys Thr Gly Ala Ala Gly Thr Cys
305                 310                 315                 320

Thr Gly Ala Gly Gly Ala Cys Ala Cys Ala Gly Cys Cys Ala Thr Gly
                325                 330                 335

Thr Ala Thr Thr Ala Cys Thr Gly Thr Gly Cys Ala Ala Gly Ala Cys
            340                 345                 350

Gly Gly Gly Gly Gly Thr Thr Ala Cys Cys Gly Thr Thr Cys Cys Ala
        355                 360                 365

Thr Gly Cys Thr Ala Thr Gly Gly Ala Cys Thr Ala Thr Thr Gly Gly
    370                 375                 380

Gly Gly Thr Cys Ala Ala Gly Gly Ala Ala Cys Cys Thr Cys Ala Gly
385                 390                 395                 400

Thr Cys Ala Cys Cys Gly Thr Cys Thr Cys Cys Thr Cys Ala Gly Cys
                405                 410                 415
```

```
Cys Ala Ala Ala Ala Cys Gly Ala Gly Gly Gly Cys Cys Cys Ala
            420             425             430
Thr Cys Cys Gly Thr Cys Thr Thr Cys Cys Cys Cys Thr Gly Gly
        435             440             445
Cys Gly Cys Cys Thr Gly Cys Thr Cys Ala Gly Gly Ala Gly
450             455             460
Cys Ala Cys Cys Thr Cys Cys Gly Ala Gly Ala Gly Cys Ala Cys Ala
465             470             475             480
Gly Cys Cys Gly Cys Cys Thr Gly Gly Cys Thr Gly Cys Cys
            485             490             495
Thr Gly Gly Thr Cys Ala Ala Gly Gly Ala Cys Thr Ala Cys Thr Thr
        500             505             510
Cys Cys Cys Cys Gly Ala Ala Cys Cys Gly Gly Thr Gly Ala Cys Gly
            515             520             525
Gly Thr Gly Thr Cys Gly Thr Gly Gly Ala Ala Cys Thr Cys Ala Gly
        530             535             540
Gly Cys Gly Cys Cys Cys Thr Gly Ala Cys Cys Ala Gly Cys Gly Gly
545             550             555             560
Cys Gly Thr Gly Cys Ala Cys Ala Cys Cys Thr Thr Cys Cys Cys Gly
            565             570             575
Gly Cys Thr Gly Thr Cys Cys Thr Ala Cys Ala Gly Thr Cys Cys Thr
        580             585             590
Cys Ala Gly Gly Ala Cys Thr Cys Thr Ala Cys Thr Cys Cys Cys Thr
            595             600             605
Cys Ala Gly Cys Ala Gly Cys Gly Thr Gly Gly Thr Gly Ala Cys Cys
610             615             620
Gly Thr Gly Cys Cys Cys Thr Cys Cys Ala Gly Cys Ala Gly Cys Thr
625             630             635             640
Thr Gly Gly Gly Cys Ala Cys Gly Ala Ala Gly Ala Cys Cys Thr Ala
            645             650             655
Cys Ala Cys Cys Thr Gly Cys Ala Ala Cys Gly Thr Ala Gly Ala Thr
        660             665             670
Cys Ala Cys Ala Ala Gly Cys Cys Cys Ala Gly Cys Ala Ala Cys Ala
            675             680             685
Cys Cys Ala Ala Gly Gly Thr Gly Gly Ala Cys Ala Ala Gly Ala Gly
        690             695             700
Ala Gly Thr Thr Gly Ala Gly Thr Cys Cys Ala Ala Ala Thr Ala Thr
705             710             715             720
Gly Gly Thr Cys Cys Cys Cys Cys Ala Thr Gly Cys Cys Cys Ala Cys
            725             730             735
Cys Cys Thr Gly Cys Cys Cys Ala Gly Cys Ala Cys Cys Thr Gly Ala
            740             745             750
Gly Thr Thr Cys Gly Ala Ala Gly Gly Gly Gly Ala Cys Cys Ala
        755             760             765
Thr Cys Ala Gly Thr Cys Thr Thr Cys Cys Thr Gly Thr Thr Cys Cys
        770             775             780
Cys Cys Cys Cys Ala Ala Ala Ala Cys Cys Cys Ala Ala Gly Gly Ala
785             790             795             800
Cys Ala Cys Thr Cys Thr Cys Ala Thr Gly Ala Thr Cys Thr Cys Cys
            805             810             815
Cys Gly Gly Ala Cys Cys Cys Cys Thr Gly Ala Gly Gly Thr Cys Ala
            820             825             830
Cys Gly Thr Gly Cys Gly Thr Gly Gly Thr Gly Gly Thr Gly Gly Ala
```

```
                    835                 840                 845
Cys Gly Thr Gly Ala Gly Cys Cys Ala Gly Ala Ala Gly Ala Cys
            850                 855                 860
Cys Cys Cys Gly Ala Gly Gly Thr Cys Cys Ala Gly Thr Thr Cys Ala
865                 870                 875                 880
Ala Cys Thr Gly Gly Thr Ala Cys Gly Thr Gly Gly Ala Thr Gly Gly
                    885                 890                 895
Cys Gly Thr Gly Gly Ala Gly Gly Thr Gly Cys Ala Thr Ala Ala Thr
            900                 905                 910
Gly Cys Cys Ala Ala Gly Ala Cys Ala Ala Gly Cys Cys Gly Cys
            915                 920                 925
Gly Gly Gly Ala Gly Gly Ala Gly Cys Ala Gly Thr Thr Cys Ala Ala
            930                 935                 940
Cys Ala Gly Cys Ala Cys Gly Thr Ala Cys Cys Gly Thr Gly Thr Gly
945                 950                 955                 960
Gly Thr Cys Ala Gly Cys Gly Thr Cys Cys Thr Cys Ala Cys Cys Gly
            965                 970                 975
Thr Cys Cys Thr Gly Cys Ala Cys Cys Ala Gly Gly Ala Cys Thr Gly
            980                 985                 990
Gly Cys Thr Gly Ala Ala Cys Gly  Gly Cys Ala Ala Gly  Gly Ala Gly
            995                 1000                1005
Thr Ala  Cys Ala Ala Gly Thr  Gly Cys Ala Ala Gly  Gly Thr Cys
    1010                1015                1020
Thr Cys  Cys Ala Ala Cys Ala  Ala Ala Gly Gly Cys  Cys Thr Cys
    1025                1030                1035
Cys Cys  Gly Thr Cys Cys Thr  Cys Cys Ala Thr Cys  Gly Ala Gly
    1040                1045                1050
Ala Ala  Ala Ala Cys Cys Ala  Thr Cys Thr Cys Cys  Ala Ala Ala
    1055                1060                1065
Gly Cys  Cys Ala Ala Ala Gly  Gly Gly Cys Ala Gly  Cys Cys Cys
    1070                1075                1080
Cys Gly  Ala Gly Ala Gly Cys  Cys Ala Cys Ala Gly  Gly Thr Gly
    1085                1090                1095
Thr Ala  Cys Ala Cys Cys Cys  Thr Gly Cys Cys Cys  Cys Cys Ala
    1100                1105                1110
Thr Cys  Cys Cys Ala Gly Gly  Ala Gly Gly Ala Gly  Ala Thr Gly
    1115                1120                1125
Ala Cys  Cys Ala Ala Gly Ala  Ala Cys Cys Ala Gly  Gly Thr Cys
    1130                1135                1140
Ala Gly  Cys Cys Thr Gly Ala  Cys Cys Thr Gly Cys  Cys Thr Gly
    1145                1150                1155
Gly Thr  Cys Ala Ala Ala Gly  Gly Cys Thr Thr Cys  Thr Ala Cys
    1160                1165                1170
Cys Cys  Cys Ala Gly Cys Gly  Ala Cys Ala Thr Cys  Gly Cys Cys
    1175                1180                1185
Gly Thr  Gly Gly Ala Gly Thr  Gly Gly Gly Ala Gly  Ala Gly Cys
    1190                1195                1200
Ala Ala  Thr Gly Gly Gly Cys  Ala Gly Cys Cys Gly  Gly Ala Gly
    1205                1210                1215
Ala Ala  Cys Ala Ala Cys Thr  Ala Cys Ala Ala Gly  Ala Cys Cys
    1220                1225                1230
Ala Cys  Gly Cys Cys Thr Cys  Cys Cys Gly Thr Gly  Cys Thr Gly
    1235                1240                1245
```

```
Gly Ala Cys Thr Cys Cys Gly Ala Cys Gly Cys Thr Cys Cys
    1250              1255             1260

Thr Thr Cys Thr Thr Cys Cys Thr Cys Thr Ala Cys Ala Gly Cys
    1265              1270             1275

Ala Gly Gly Cys Thr Ala Ala Cys Cys Gly Thr Gly Gly Ala Cys
    1280              1285             1290

Ala Ala Gly Ala Gly Cys Ala Gly Gly Thr Gly Cys Ala Gly
    1295              1300             1305

Gly Ala Gly Gly Gly Gly Ala Ala Thr Gly Thr Cys Thr Thr Cys
    1310              1315             1320

Thr Cys Ala Thr Gly Cys Thr Cys Cys Gly Thr Gly Ala Thr Gly
    1325              1330             1335

Cys Ala Thr Gly Ala Gly Gly Cys Thr Cys Thr Gly Cys Ala Cys
    1340              1345             1350

Ala Ala Cys Cys Ala Cys Thr Ala Cys Ala Cys Ala Cys Ala Gly
    1355              1360             1365

Ala Ala Gly Ala Gly Cys Cys Thr Cys Thr Cys Cys Cys Thr Gly
    1370              1375             1380

Thr Cys Thr Cys Thr Gly Gly Gly Thr Ala Ala Ala Gly Cys Thr
    1385              1390             1395

Ala Gly Cys Thr Gly Ala Glu Val Lys Leu Val Glu Ser Gly Gly
    1400              1405             1410

Gly Leu Val Gln Pro Gly Gly Ser Leu Lys Leu Ser Cys Ala Thr
    1415              1420             1425

Ser Gly Phe Thr Phe Ser Asp Tyr Tyr Met Tyr Trp Val Arg Gln
    1430              1435             1440

Thr Pro Glu Lys Arg Leu Glu Trp Val Ala Tyr Ile Asn Ser Gly
    1445              1450             1455

Gly Gly Ser Thr Tyr Tyr Pro Asp Thr Val Lys Gly Arg Phe Thr
    1460              1465             1470

Ile Ser Arg Asp Asn Ala Lys Asn Thr Leu Tyr Leu Gln Met Ser
    1475              1480             1485

Arg Leu Lys Ser Glu Asp Thr Ala Met Tyr Tyr Cys Ala Arg Arg
    1490              1495             1500

Gly Leu Pro Phe His Ala Met Asp Tyr Trp Gly Gln Gly Thr Ser
    1505              1510             1515

Val Thr Val Ser Ser Ala Lys Thr Lys Gly Pro Ser Val Phe Pro
    1520              1525             1530

Leu Ala Pro Cys Ser Arg Ser Thr Ser Glu Ser Thr Ala Ala Leu
    1535              1540             1545

Gly Cys Leu Val Lys Asp Tyr Phe Pro Glu Pro Val Thr Val Ser
    1550              1555             1560

Trp Asn Ser Gly Ala Leu Thr Ser Gly Val His Thr Phe Pro Ala
    1565              1570             1575

Val Leu Gln Ser Ser Gly Leu Tyr Ser Leu Ser Ser Val Val Thr
    1580              1585             1590

Val Pro Ser Ser Ser Leu Gly Thr Lys Thr Tyr Thr Cys Asn Val
    1595              1600             1605

Asp His Lys Pro Ser Asn Thr Lys Val Asp Lys Arg Val Glu Ser
    1610              1615             1620

Lys Tyr Gly Pro Pro Cys Pro Pro Cys Pro Ala Pro Glu Phe Glu
    1625              1630             1635
```

Gly Gly Pro Ser Val Phe Leu Phe Pro Pro Lys Pro Lys Asp Thr
1640                1645                1650

Leu Met Ile Ser Arg Thr Pro Glu Val Thr Cys Val Val Val Asp
1655                1660                1665

Val Ser Gln Glu Asp Pro Glu Val Gln Phe Asn Trp Tyr Val Asp
1670                1675                1680

Gly Val Glu Val His Asn Ala Lys Thr Lys Pro Arg Glu Glu Gln
1685                1690                1695

Phe Asn Ser Thr Tyr Arg Val Val Ser Val Leu Thr Val Leu His
1700                1705                1710

Gln Asp Trp Leu Asn Gly Lys Glu Tyr Lys Cys Lys Val Ser Asn
1715                1720                1725

Lys Gly Leu Pro Ser Ser Ile Glu Lys Thr Ile Ser Lys Ala Lys
1730                1735                1740

Gly Gln Pro Arg Glu Pro Gln Val Tyr Thr Leu Pro Pro Ser Gln
1745                1750                1755

Glu Glu Met Thr Lys Asn Gln Val Ser Leu Thr Cys Leu Val Lys
1760                1765                1770

Gly Phe Tyr Pro Ser Asp Ile Ala Val Glu Trp Glu Ser Asn Gly
1775                1780                1785

Gln Pro Glu Asn Asn Tyr Lys Thr Thr Pro Pro Val Leu Asp Ser
1790                1795                1800

Asp Gly Ser Phe Phe Leu Tyr Ser Arg Leu Thr Val Asp Lys Ser
1805                1810                1815

Arg Trp Gln Glu Gly Asn Val Phe Ser Cys Ser Val Met His Glu
1820                1825                1830

Ala Leu His Asn His Tyr Thr Gln Lys Ser Leu Ser Leu Ser Leu
1835                1840                1845

Gly Lys Ala Ser
1850

<210> SEQ ID NO 21
<211> LENGTH: 782
<212> TYPE: PRT
<213> ORGANISM: Artificial Sequence
<220> FEATURE:
<223> OTHER INFORMATION: Synthesized Sequence

<400> SEQUENCE: 21

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

```
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
210                 215                 220
Cys Pro Pro Cys Pro Ala Pro Glu Phe Glu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys Ala Ser
        435                 440                 445
Asp Thr Thr Glu Pro Ala Thr Pro Thr Thr Pro Val Thr Thr Asp Thr
    450                 455                 460
Ile Cys Ile Gly Tyr His Ala Asn Asn Ser Thr Asp Thr Val Asp Thr
465                 470                 475                 480
Val Leu Glu Lys Asn Val Thr Val Thr His Ser Val Asn Leu Leu Glu
                485                 490                 495
Asp Ser His Asn Gly Lys Leu Cys Arg Leu Lys Gly Ile Ala Pro Leu
            500                 505                 510
Gln Leu Gly Lys Cys Asn Ile Ala Gly Trp Leu Leu Gly Asn Pro Glu
        515                 520                 525
Cys Asp Pro Leu Leu Pro Val Arg Ser Trp Ser Tyr Ile Val Glu Thr
    530                 535                 540
Pro Asn Ser Glu Asn Gly Ile Cys Tyr Pro Gly Asp Phe Ile Asp Tyr
```

```
545                 550                 555                 560
Glu Glu Leu Arg Glu Gln Leu Ser Ser Val Ser Ser Phe Glu Arg Phe
                565                 570                 575
Glu Ile Phe Pro Lys Glu Ser Ser Trp Pro Asn His Asn Thr Asn Gly
                580                 585                 590
Val Thr Ala Ala Cys Ser His Glu Gly Lys Ser Ser Phe Tyr Arg Asn
                595                 600                 605
Leu Leu Trp Leu Thr Glu Lys Glu Gly Ser Tyr Pro Lys Leu Lys Asn
                610                 615                 620
Ser Tyr Val Asn Lys Lys Gly Lys Glu Val Leu Val Leu Trp Gly Ile
625                 630                 635                 640
His His Pro Pro Asn Ser Lys Glu Gln Gln Asn Leu Tyr Gln Asn Glu
                645                 650                 655
Asn Ala Tyr Val Ser Val Val Thr Ser Asn Tyr Asn Arg Arg Phe Thr
                660                 665                 670
Pro Glu Ile Ala Glu Arg Pro Lys Val Arg Asp Gln Ala Gly Arg Met
                675                 680                 685
Asn Tyr Tyr Trp Thr Leu Leu Lys Pro Gly Asp Thr Ile Ile Phe Glu
                690                 695                 700
Ala Asn Gly Asn Leu Ile Ala Pro Met Tyr Ala Phe Ala Leu Ser Arg
705                 710                 715                 720
Gly Phe Gly Ser Gly Ile Ile Thr Ser Asn Ala Ser Met His Glu Cys
                725                 730                 735
Asn Thr Lys Cys Gln Thr Pro Leu Gly Ala Ile Asn Ser Ser Leu Pro
                740                 745                 750
Tyr Gln Asn Ile His Pro Val Thr Ile Gly Glu Cys Leu Lys Tyr Val
                755                 760                 765
Arg Ser Ala Lys Leu Arg Met Val His His His His His
                770                 775                 780

<210> SEQ ID NO 22
<211> LENGTH: 523
<212> TYPE: PRT
<213> ORGANISM: Artificial Sequence
<220> FEATURE:
<223> OTHER INFORMATION: Synthesized Sequence

<400> SEQUENCE: 22

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
                20                  25                  30

Tyr Met Tyr Trp Val Arg Gln Thr Pro Glu Lys Arg Leu Glu Trp Val
            35                  40                  45

Ala Tyr Ile Asn Ser Gly Gly Gly Ser Thr Tyr Tyr Pro Asp Thr Val
        50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
                100                 105                 110

Thr Ser Val Thr Val Ser Ser Ala Lys Thr Lys Gly Pro Ser Val Phe
            115                 120                 125

Pro Leu Ala Pro Cys Ser Arg Ser Thr Ser Glu Ser Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

Asn Ser Pro Gln Asn Glu Val Leu Tyr Gly Asp Val Asn Asp Asp Gly
450                 455                 460

Lys Val Asn Ser Thr Asp Leu Thr Leu Leu Lys Arg Tyr Val Leu Lys
465                 470                 475                 480

Ala Val Ser Thr Leu Pro Ser Ser Lys Ala Glu Lys Asn Ala Asp Val
                485                 490                 495

Asn Arg Asp Gly Arg Val Asp Ser Ser Asp Val Thr Ile Leu Ser Arg
            500                 505                 510

Tyr Leu Ile Arg Val Ile Glu Lys Leu Pro Ile
        515                 520

<210> SEQ ID NO 23
<211> LENGTH: 430
<212> TYPE: PRT
<213> ORGANISM: Artificial Sequence
```

<220> FEATURE:
<223> OTHER INFORMATION: Synthesized Sequence

<400> SEQUENCE: 23

```
Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
        35                  40                  45

Leu Glu Ile Ile Glu Ile Lys Pro Gly Glu Leu Ile Val Asp Pro Asn
    50                  55                  60

Pro Thr Lys Ser Phe Asp Thr Ala Val Tyr Pro Asp Arg Lys Met Ile
65                  70                  75                  80

Val Phe Leu Phe Ala Glu Asp Ser Gly Thr Gly Ala Tyr Ala Ile Thr
                85                  90                  95

Lys Asp Gly Val Phe Ala Thr Ile Val Ala Lys Val Lys Glu Gly Ala
            100                 105                 110

Pro Asn Gly Leu Ser Val Ile Lys Phe Val Glu Val Gly Gly Phe Ala
        115                 120                 125

Asn Asn Asp Leu Val Glu Gln Lys Thr Gln Phe Phe Asp Gly Gly Val
    130                 135                 140

Asn Val Gly Asp Thr Thr Glu Pro Ala Thr Pro Thr Pro Val Thr
145                 150                 155                 160

Thr Pro Thr Thr Thr Asp Asp Leu Asp Ala Ala Ser Leu Leu Thr Glu
                165                 170                 175

Val Glu Thr Tyr Val Leu Ser Ile Ile Pro Ser Gly Pro Leu Lys Ala
            180                 185                 190

Glu Ile Ala Gln Arg Leu Glu Asp Val Phe Ala Gly Lys Asn Thr Asp
        195                 200                 205

Leu Glu Val Leu Met Glu Trp Leu Lys Thr Arg Pro Ile Leu Ser Pro
    210                 215                 220

Leu Thr Lys Gly Ile Leu Gly Phe Val Phe Thr Leu Thr Val Pro Ser
225                 230                 235                 240

Glu Arg Gly Leu Gln Arg Arg Phe Val Gln Asn Ala Leu Asn Gly
                245                 250                 255

Asn Gly Asp Pro Asn Asn Met Asp Lys Ala Val Lys Leu Tyr Arg Lys
            260                 265                 270

Leu Lys Arg Glu Ile Thr Phe His Gly Ala Lys Glu Ile Ala Leu Ser
        275                 280                 285

Tyr Ser Ala Gly Ala Leu Ala Ser Cys Met Gly Leu Ile Tyr Asn Arg
    290                 295                 300

Met Gly Ala Val Thr Thr Glu Val Ala Phe Gly Leu Val Cys Ala Thr
305                 310                 315                 320

Cys Glu Gln Ile Ala Asp Ser Gln His Arg Ser His Arg Gln Met Val
                325                 330                 335

Thr Thr Thr Asn Pro Leu Ile Arg His Glu Asn Arg Met Val Leu Ala
            340                 345                 350

Ser Thr Thr Ala Lys Ala Met Glu Gln Met Ala Gly Ser Ser Glu Gln
        355                 360                 365

Ala Ala Glu Ala Met Asp Ile Ala Ser Gln Ala Arg Gln Met Val Gln
    370                 375                 380

Ala Met Arg Thr Ile Gly Thr His Pro Ser Ser Ser Ala Gly Leu Lys
385                 390                 395                 400
```

```
Asp Asp Leu Leu Glu Asn Leu Gln Ala Tyr Gln Lys Arg Met Gly Val
                405                 410                 415

Gln Met Gln Arg Phe Lys Leu Glu His His His His His His
            420                 425                 430

<210> SEQ ID NO 24
<211> LENGTH: 214
<212> TYPE: PRT
<213> ORGANISM: Artificial Sequence
<220> FEATURE:
<223> OTHER INFORMATION: Synthesized Sequence

<400> SEQUENCE: 24

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Asp Tyr Ser Leu Thr Ile Gly Asn Leu Glu Pro
65                  70                  75                  80

Glu Asp Ile Ala Thr Tyr Tyr Cys Gln Gln Phe Asn Lys Leu Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 25
<211> LENGTH: 214
<212> TYPE: PRT
<213> ORGANISM: Artificial Sequence
<220> FEATURE:
<223> OTHER INFORMATION: Synthesized Sequence

<400> SEQUENCE: 25

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

His Tyr Thr Ser Ile Leu His Ser Gly Val Pro Ser Arg Phe Ser Gly
```

```
                 50                  55                  60
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Phe Asn Lys Leu Pro Pro
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 213
<212> TYPE: PRT
<213> ORGANISM: Artificial Sequence
<220> FEATURE:
<223> OTHER INFORMATION: Synthesized Sequence

<400> SEQUENCE: 26

Asp Ile Gln Met Thr Gln Thr Thr Ser Ser Leu Ser Ala Ser Leu Gly
 1               5                  10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

His Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
 65                  70                  75                  80

Asp Ile Ala Thr Tyr Phe Cys Gln Gln Phe Asn Lys Leu Pro Pro Thr
                 85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
```

Asn Arg Gly Glu Cys
    210

<210> SEQ ID NO 27
<211> LENGTH: 214
<212> TYPE: PRT
<213> ORGANISM: Artificial Sequence
<220> FEATURE:
<223> OTHER INFORMATION: Synthesized Sequence

<400> SEQUENCE: 27

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

His Tyr Thr Ser Ile Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Phe Asn Lys Pro Pro Pro
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 214
<212> TYPE: PRT
<213> ORGANISM: Artificial Sequence
<220> FEATURE:
<223> OTHER INFORMATION: Synthesized Sequence

<400> SEQUENCE: 28

Asp Ile Gln Met Thr Gln Thr Thr Ser Ser Leu Ser Thr Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

His Tyr Thr Ser Ile Leu His Ser Gly Val Pro Ser Arg Phe Ser Gly
    50                  55                  60

```
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Phe Asn Lys Leu Pro Pro
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 29
<211> LENGTH: 448
<212> TYPE: PRT
<213> ORGANISM: Artificial Sequence
<220> FEATURE:
<223> OTHER INFORMATION: Synthesized Sequence

<400> SEQUENCE: 29

Glu Val Lys Leu Val Glu Ser Gly Gly Gly Leu Val Gln Pro Gly Gly
  1               5                  10                  15

Ser Leu Lys Leu Ser Cys Ala Thr Ser Gly Phe Thr Phe Ser Asp Tyr
             20                  25                  30

Tyr Met Tyr Trp Val Arg Gln Thr Pro Glu Lys Arg Leu Glu Trp Val
         35                  40                  45

Ala Tyr Ile Asn Ser Gly Gly Gly Ser Thr Tyr Tyr Pro Asp Thr Val
     50                  55                  60

Lys Gly Arg Phe Thr Ile Ser Arg Asp Asn Ala Lys Asn Thr Leu Tyr
 65                  70                  75                  80

Leu Gln Met Ser Arg Leu Lys Ser Glu Asp Thr Ala Met Tyr Tyr Cys
                 85                  90                  95

Ala Arg Arg Gly Leu Pro Phe His Ala Met Asp Tyr Trp Gly Gln Gly
            100                 105                 110

Thr Ser Val Thr Val Ser Ser Ala Lys Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205
```

Ser Asn Thr Lys Val Asp Lys Arg Val Glu Ser Lys Tyr Gly Pro Pro
210                 215                 220

Cys Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
            435                 440                 445

<210> SEQ ID NO 30
<211> LENGTH: 448
<212> TYPE: PRT
<213> ORGANISM: Artificial Sequence
<220> FEATURE:
<223> OTHER INFORMATION: Synthesized Sequence

<400> SEQUENCE: 30

Glu Val Asn Leu Val Glu Ser Gly Gly Gly Leu Val Gln Pro Gly Gly
1               5                   10                  15

Ser Leu Lys Val Ser Cys Val Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Ser Arg Leu Lys Ser Glu Asp Thr Ala Met Tyr Tyr Cys
                85                  90                  95

Ala Arg Arg Gly Leu Pro Phe His Ala Met Asp Tyr Trp Gly Gln Gly
            100                 105                 110

Thr Leu Val Thr Val Ser Val Ala Ser Thr Lys Gly Pro Ser Val Phe
        115                 120                 125

```
Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Glu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys Ala Ser
        435                 440                 445

<210> SEQ ID NO 31
<211> LENGTH: 1100
<212> TYPE: PRT
<213> ORGANISM: Artificial Sequence
<220> FEATURE:
<223> OTHER INFORMATION: Synthesized Sequence

<400> SEQUENCE: 31

Glu Val Lys Leu Val Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45
```

```
Ala Tyr Ile Asn Ser Gly Gly Gly Ser Thr Tyr Tyr Pro Asp Thr Val
 50                  55                  60
Lys Gly Arg Phe Thr Ile Ser Arg Asp Asn Ala Lys Asn Thr Leu Tyr
 65                  70                  75                  80
Leu Gln Met Ser Arg Leu Lys Ser Glu Asp Thr Ala Met Tyr Tyr Cys
                 85                  90                  95
Ala Arg Arg Gly Leu Pro Phe His Ala Met Asp Tyr Trp Gly Gln Gly
                100                 105                 110
Thr Ser Val Thr Val Ser Ser Ala Lys Thr Lys Gly Pro Ser Val Phe
            115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
210                 215                 220
Cys Pro Pro Cys Pro Ala Pro Glu Phe Glu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Phe Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu Gly Lys Ala Ser
        435                 440                 445
Gln Thr Pro Thr Asn Thr Ile Ser Val Thr Pro Thr Asn Asn Ser Thr
450                 455                 460
Pro Thr Asn Asn Ser Asn Pro Lys Pro Asn Pro Ala Ser Leu Glu Met
```

```
                465                 470                 475                 480
         Gly Ala Arg Ala Ser Ile Leu Ser Gly Gly Glu Leu Asp Arg Trp Glu
                             485                 490                 495
         Lys Ile Arg Leu Arg Pro Gly Gly Lys Lys Tyr Lys Leu Lys His
                         500                 505                 510
         Ile Val Trp Ala Ser Arg Glu Leu Glu Arg Phe Ala Val Asn Pro Gly
                     515                 520                 525
         Leu Leu Glu Thr Ser Glu Gly Cys Arg Gln Ile Leu Gly Gln Leu Gln
                 530                 535                 540
         Pro Ser Leu Gln Thr Gly Ser Glu Glu Leu Arg Ser Leu Tyr Asn Thr
         545                 550                 555                 560
         Val Ala Thr Leu Tyr Cys Val His Gln Arg Ile Glu Ile Lys Asp Thr
                             565                 570                 575
         Lys Glu Ala Leu Asp Lys Ile Glu Glu Gln Asn Lys Ser Val Asp
                         580                 585                 590
         Thr Val Thr Pro Thr Ala Thr Pro Ser Ala Ile Val Thr Thr
                     595                 600                 605
         Ile Thr Pro Thr Ala Thr Thr Lys Pro Val Asp Met Gly Gly Lys Trp
                 610                 615                 620
         Ser Lys Arg Ser Val Val Gly Trp Pro Thr Val Arg Glu Arg Met Arg
         625                 630                 635                 640
         Arg Ala Glu Pro Ala Ala Asp Gly Val Gly Ala Val Ser Arg Asp Leu
                             645                 650                 655
         Glu Lys His Gly Ala Ile Thr Ser Ser Asn Thr Ala Ala Asn Asn Ala
                         660                 665                 670
         Asp Cys Ala Trp Leu Glu Ala Gln Glu Glu Glu Val Gly Phe Pro
                     675                 680                 685
         Val Arg Pro Gln Val Pro Leu Arg Pro Met Thr Tyr Lys Gly Ala Leu
                 690                 695                 700
         Asp Leu Ser His Phe Leu Lys Glu Lys Gly Gly Leu Glu Gly Leu Ile
         705                 710                 715                 720
         Tyr Ser Gln Lys Arg Gln Asp Ile Leu Asp Leu Trp Val Tyr His Thr
                             725                 730                 735
         Gln Gly Tyr Phe Pro Asp Trp Gln Asn Tyr Thr Pro Gly Pro Gly Ile
                         740                 745                 750
         Arg Tyr Pro Leu Thr Phe Gly Trp Cys Phe Lys Leu Val Pro Val Glu
                     755                 760                 765
         Pro Glu Lys Val Glu Glu Ala Asn Glu Gly Glu Asn Asn Ser Leu Leu
                 770                 775                 780
         His Pro Met Ser Leu His Gly Met Asp Asp Pro Glu Arg Glu Val Leu
         785                 790                 795                 800
         Val Trp Lys Phe Asp Ser Arg Leu Ala Phe His His Met Ala Arg Glu
                             805                 810                 815
         Leu His Pro Glu Tyr Tyr Lys Asp Cys Glu Phe Thr Asn Gly Ser Ile
                         820                 825                 830
         Thr Val Ala Ala Thr Ala Pro Thr Val Thr Pro Thr Val Asn Ala Thr
                     835                 840                 845
         Pro Ser Ala Ala Gln Phe Ala Gln Gln Ala Ala Asp Thr Gly His
                 850                 855                 860
         Ser Asn Gln Val Ser Gln Asn Tyr Pro Ile Val Gln Asn Ile Gln Gly
         865                 870                 875                 880
         Gln Met Val His Gln Ala Ile Ser Pro Arg Thr Leu Asn Ala Trp Val
                             885                 890                 895
```

-continued

```
Lys Val Val Glu Glu Lys Ala Phe Ser Pro Glu Val Ile Pro Met Phe
            900                 905                 910

Ser Ala Leu Ser Glu Gly Ala Thr Pro Gln Asp Leu Asn Thr Met Leu
            915                 920                 925

Asn Thr Val Gly Gly His Gln Ala Ala Met Gln Met Leu Lys Glu Thr
        930                 935                 940

Ile Asn Glu Glu Ala Ala Glu Trp Asp Arg Val His Pro Val His Ala
945                 950                 955                 960

Gly Pro Ile Ala Pro Gly Gln Met Arg Glu Pro Arg Gly Ser Asp Ile
                965                 970                 975

Ala Gly Thr Thr Ser Thr Leu Gln Glu Gln Ile Gly Trp Met Thr His
            980                 985                 990

Asn Pro Pro Ile Pro Val Gly Glu Ile Tyr Lys Arg Trp Ile Ile Leu
        995                 1000                1005

Gly Leu Asn Lys Ile Val Arg Met Tyr Ser Pro Thr Ser Ile Leu
        1010                1015                1020

Asp Ile Arg Gln Gly Pro Lys Glu Pro Phe Arg Asp Tyr Val Asp
        1025                1030                1035

Arg Phe Tyr Lys Thr Leu Arg Ala Glu Gln Ala Ser Gln Glu Val
        1040                1045                1050

Lys Asn Trp Met Thr Glu Thr Leu Leu Val Gln Asn Ala Asn Pro
        1055                1060                1065

Asp Cys Lys Thr Ile Leu Lys Ala Leu Gly Pro Gly Ala Thr Leu
        1070                1075                1080

Glu Glu Met Met Thr Ala Cys Gln Gly Val Gly His His His His
        1085                1090                1095

His His
        1100

<210> SEQ ID NO 32
<211> LENGTH: 475
<212> TYPE: PRT
<213> ORGANISM: Artificial Sequence
<220> FEATURE:
<223> OTHER INFORMATION: Synthesized Sequence

<400> SEQUENCE: 32

Met Asp Leu Asp Ala Val Arg Ile Lys Val Asp Thr Val Asn Ala Lys
1               5                   10                  15

Pro Gly Asp Thr Val Asn Ile Pro Val Arg Phe Ser Gly Ile Pro Ser
            20                  25                  30

Lys Gly Ile Ala Asn Cys Asp Phe Val Tyr Ser Tyr Asp Pro Asn Val
        35                  40                  45

Leu Glu Ile Ile Glu Ile Lys Pro Gly Glu Leu Ile Val Asp Pro Asn
    50                  55                  60

Pro Thr Lys Ser Phe Asp Thr Ala Val Tyr Pro Asp Arg Lys Met Ile
65                  70                  75                  80

Val Phe Leu Phe Ala Glu Asp Ser Gly Thr Gly Ala Tyr Ala Ile Thr
                85                  90                  95
```

-continued

```
Lys Asp Gly Val Phe Ala Thr Ile Val Ala Lys Val Lys Glu Gly Ala
                100                 105                 110
Pro Asn Gly Leu Ser Val Ile Lys Phe Val Glu Val Gly Gly Phe Ala
            115                 120                 125
Asn Asn Asp Leu Val Glu Gln Lys Thr Gln Phe Phe Asp Gly Gly Val
        130                 135                 140
Asn Val Gly Asp Thr Thr Glu Pro Ala Thr Pro Thr Thr Pro Val Thr
145                 150                 155                 160
Thr Pro Thr Thr Thr Asp Asp Leu Asp Ala Ala Ser Leu Glu Met Glu
                165                 170                 175
His Gln Leu Leu Cys Cys Glu Val Glu Thr Ile Arg Arg Ala Tyr Pro
            180                 185                 190
Asp Ala Asn Leu Leu Asn Asp Arg Val Leu Arg Ala Met Leu Lys Ala
        195                 200                 205
Glu Glu Thr Cys Ala Pro Ser Val Ser Tyr Phe Lys Cys Val Gln Lys
    210                 215                 220
Glu Val Leu Pro Ser Met Arg Lys Ile Val Ala Thr Trp Met Leu Glu
225                 230                 235                 240
Val Cys Glu Glu Gln Lys Cys Glu Glu Val Phe Pro Leu Ala Met
                245                 250                 255
Asn Tyr Leu Asp Arg Phe Leu Ser Leu Glu Pro Val Lys Lys Ser Arg
            260                 265                 270
Leu Gln Leu Leu Gly Ala Thr Cys Met Phe Val Ala Ser Lys Met Lys
        275                 280                 285
Glu Thr Ile Pro Leu Thr Ala Glu Lys Leu Cys Ile Tyr Thr Asp Asn
    290                 295                 300
Ser Ile Arg Pro Glu Glu Leu Leu Gln Met Glu Leu Leu Leu Val Asn
305                 310                 315                 320
Lys Leu Lys Trp Asn Leu Ala Ala Met Thr Pro His Asp Phe Ile Glu
                325                 330                 335
His Phe Leu Ser Lys Met Pro Glu Ala Glu Asn Lys Gln Ile Ile
            340                 345                 350
Arg Lys His Ala Gln Thr Phe Val Ala Leu Cys Ala Thr Asp Val Lys
        355                 360                 365
Phe Ile Ser Asn Pro Pro Ser Met Val Ala Ala Gly Ser Val Val Ala
    370                 375                 380
Ala Val Gln Gly Leu Asn Leu Arg Ser Pro Asn Asn Phe Leu Ser Tyr
385                 390                 395                 400
Tyr Arg Leu Thr Arg Phe Leu Ser Arg Val Ile Lys Cys Asp Pro Asp
                405                 410                 415
Cys Leu Arg Ala Cys Gln Glu Gln Ile Glu Ala Leu Leu Glu Ser Ser
            420                 425                 430
Leu Arg Gln Ala Gln Gln Asn Met Asp Pro Lys Ala Ala Glu Glu Glu
        435                 440                 445
Glu Glu Glu Glu Glu Glu Val Asp Leu Ala Cys Thr Pro Thr Asp Val
    450                 455                 460
Arg Asp Val Asp Ile His His His His His
465                 470                 475
```

DENDRITIC CELL-SPECIFIC ANTIBODY CONJUGATE COMPRISING ANTI-CD40 MONOCLONAL ANTIBODIES CONJUGATED TO HIV-1 GAG/NEF

CROSS-REFERENCE TO RELATED APPLICATIONS

This application claims priority to U.S. Provisional Application Ser. No. 61/081,234, filed Jul. 16, 2008, the entire contents of which are incorporated herein by reference.

STATEMENT OF FEDERALLY FUNDED RESEARCH

This invention was made with U.S. Government support under Contract No. 1U19AI057234-0100003 awarded by the NIH. The government has certain rights in this invention.

TECHNICAL FIELD OF THE INVENTION

The present invention relates in general to the field of agents that target viral proteins to dendritic cells.

BACKGROUND OF THE INVENTION

Without limiting the scope of the invention, its background is described in connection with antigen presentation.

Dendritic Cells play a pivotal role in controlling the interface of innate and acquired immunity by providing soluble and intercellular signals, followed by recognition of pathogens. These functions of DCs are largely dependent on the expression of specialized surface receptors, 'pattern recognition receptors' (PRRs), represented, most notably, by toll-like receptors (TLRs) and C-type lectins or lectin-like receptors (LLRs).

In the current paradigm, a major role of TLRs is to alert DCs to produce interleukin 12 (IL-12) and other inflammatory cytokines for initiating immune responses. C-type LLRs operate as constituents of the powerful antigen capture and uptake mechanism of macrophages and DCs. Compared to TLRs, however, LLRs might have broader ranges of biological functions that include cell migrations, intercellular interactions. These multiple functions of LLRs might be due to the facts that LLRs, unlike TLRs, can recognize both self and nonself. However, the complexity of LLRs, including the redundancy of a number of LLRs expressed in immune cells, has been one of the major obstacles to understand the detailed functions of individual LLRs. In addition, natural ligands for most of these receptors remain unidentified. Nonetheless, evidence from recent studies suggests that LLRs, in collaboration with TLRs, may contribute to the activation of immune cells during microbial infections.

SUMMARY OF THE INVENTION

In one embodiment, the present invention includes compositions and methods for increasing the effectiveness of antigen presentation by an antigen presenting cell by isolating and purifying a DC-specific antibody or fragment thereof to which an engineered Gag antigen is attached to form an antibody-antigen complex, wherein the Gag antigen is less susceptible to proteolytic degradation by eliminating one or more proteolytic sites; and contacting the antigen presenting cell under conditions wherein the antibody-antigen complex is processed and presented for T cell recognition. In one aspect, the antigen presenting cell comprises a dendritic cell.

In another aspect the DC-specific antibody or fragment thereof is bound to one half of a Coherin/Dockerin pair or the DC-specific antibody or fragment thereof is bound to one half of a Coherin/Dockerin pair and the engineered Gag antigen is bound to the complementary half of the Coherin/Dockerin pair to form a complex. In another aspect, the antibody-antigen complex further comprises a flexible linker between the DC-specific antibody or fragment thereof and the Gag antigen. In one aspect, the antibody-antigen complex further comprises one or more new glycosylation sites, or the antibody-antigen complex further comprises a flexible linker between the DC-specific antibody or fragment thereof and the Gag antigen that comprises one or more glycosylation sites that provide increased flexibility between the antibody and the antigen, decreased proteolysis at the linker and increased secretion. In yet another aspect, the antibody-antigen complex further comprises a flexible linker between the DC-specific antibody or fragment thereof and the Gag antigen that comprises one or more linkers selected from SEQ ID NOS. 4 and 6.

In another aspect of the present invention, the antibody-antigen complex further comprises a flexible linker between the DC-specific antibody or fragment thereof and the Gag antigen that comprises one or more glycosylation sites selected from a linker sequence derived from a cellulose degrading organism. In one aspect, the DC-specific antibody or fragment thereof is humanized. In one specific aspect, the antibody-antigen complex is selected from SEQ ID NOS: 1, 2, 3, 4, 5, 7, 8, 9, 10, 11, 12, 13, 14, 15, 16, 17, 18, 19, 20, 21, 22, 23, 31 or 32. In another aspect, the antibody-antigen complex further comprises a sequence tag used for purification or identification of the complex. In yet another aspect, the DC-specific antibody or fragment binds is selected from an antibody that specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, LOX-1, and ASPGR.

Another embodiment of the present invention includes compositions and methods for increasing the effectiveness of antigen presentation by an antigen presenting cell by: isolating and purifying a DC-specific antibody or fragment thereof to which an engineered Nef antigen is attached to form an antibody-antigen complex, wherein the Nef antigen comprises one or more codon usage optimization that increase antibody-antigen complex secretion; and contacting the antigen presenting cell under conditions wherein the antibody-antigen complex is processed and presented for T cell recognition. In one aspect, the antigen presenting cell comprises a dendritic cell. In another aspect the DC-specific antibody or fragment thereof is bound to one half of a Coherin/Dockerin pair or the DC-specific antibody or fragment thereof is bound to one half of a Coherin/Dockerin pair and the engineered Nef antigen is bound to the complementary half of the Coherin/Dockerin pair to form a complex. In another aspect, the antibody-antigen complex further comprises a flexible linker between the DC-specific antibody or fragment thereof and the Nef antigen. In one aspect, the antibody-antigen complex further comprises one or more new glycosylation sites, or the antibody-antigen complex further comprises a flexible linker between the DC-specific antibody or fragment thereof and the Nef antigen that comprises one or more glycosylation sites that provide increased flexibility between the antibody and the antigen, decreased proteolysis at the linker and increased secretion. In one aspect, the antibody-antigen complex further comprises a flexible linker between the DC-specific antibody or fragment thereof and the Nef antigen that comprises one or more linkers selected from SEQ ID NOS. 4 and 6. In one aspect, the antibody-antigen complex further comprises a flexible linker between the DC-specific antibody or fragment thereof and the Nef antigen that comprises one or more glycosylation sites selected from a linker sequence derived from a cellulose degrading organism. In one aspect, the DC-specific antibody or fragment thereof is humanized. In yet another aspect, the antibody-antigen complex comprises SEQ ID NOS: 11, 12, 13, 14, 15, 16, and 17. In another aspect, the antibody-antigen complex further comprises a sequence tag used for purification or identification of the complex. In one aspect, the DC-specific antibody or fragment binds is selected from an antibody that specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, LOX-1, and ASPGR.

Yet another embodiment of the present invention is a vaccine comprising a DC-specific antibody or fragment thereof to which an engineered Gag antigen is attached to form an antibody-antigen complex, wherein the Gag antigen is less susceptible to proteolytic degradation by eliminating one or more proteolytic sites. In one aspect, the antibody-antigen complex further comprises a flexible linker between the DC-specific antibody or fragment thereof and the Gag antigen. In yet another aspect, the antibody-antigen complex further comprises one or more new glycosylation sites. In yet another aspect, the antibody-antigen complex further comprises a flexible linker between the DC-specific antibody or fragment thereof and the Gag antigen that comprises one or more glycosylation sites that provide increased flexibility between the antibody and the antigen, decreased proteolysis at the linker and increased secretion. In another aspect, the antibody-antigen complex further comprises a flexible linker between the DC-specific antibody or fragment thereof and the Gag antigen that comprises one or more linkers selected from SEQ ID NOS. 4 and 6. In another aspect, the antibody-antigen complex further comprises a flexible linker between the DC-specific antibody or fragment thereof and the Gag antigen that comprises one or more glycosylation sites selected from a linker sequence derived from a cellulose degrading organism. In one aspect, the DC-specific antibody or fragment thereof is humanized. In one specific aspect, the antibody-antigen complex is selected from SEQ ID NOS: 1, 2, 3, 4, 5, 7, 8, 9, 10, 11, 12, 13, 14, 15, 16, 17, 18, 19, 20, 21, 22, 23, 31 or 32. In another aspect, antibody-antigen complex further comprises a sequence tag used for purification of the complex. The skilled artisan will recognize that the antibody-antigen complex may be formed by covalent or non-covalent association between the DC-specific antibody or fragment and the antigen or in the form of a fusion protein, with either of the portions at the amino or carboxy-terminus or even as contactamers or one or more of either portion. In one aspect, the DC-specific antibody or fragment binds is selected from an antibody that specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, LOX-1, and ASPGR.

Yet another embodiment of the present invention is a vaccine comprising a DC-specific antibody or fragment thereof to which an engineered Nef antigen is attached to form an antibody-antigen complex, wherein the Nef antigen comprises one or more codon usage optimization that increase antibody-antigen complex secretion. In one aspect, the antibody-antigen complex further comprises a flexible linker between the DC-specific antibody or fragment thereof and the Nef antigen. In another aspect, the antibody-antigen complex further comprises one or more new glycosylation sites. In yet another aspect, the antibody-antigen complex further comprises a flexible linker between the DC-specific antibody or fragment thereof and the Nef antigen that comprises one or more glycosylation sites that provide increased flexibility between the antibody and the antigen, decreased proteolysis at the linker and increased secretion. In another aspect, the antibody-antigen complex further comprises a flexible linker between the DC-specific antibody or fragment thereof and the Nef antigen that comprises one or more linkers selected from SEQ ID NOS. 4 and 6. In yet another aspect, the antibody-antigen complex further comprises a flexible linker between the DC-specific antibody or fragment thereof and the Nef antigen that comprises one or more glycosylation sites selected from a linker sequence derived from a cellulose degrading organism. In one specific aspect, the DC-specific antibody or fragment thereof is humanized. In another specific aspect, the antibody-antigen complex comprises SEQ ID NOS: 1, 2, 3, 4, 5, 7, 8, 9, 10, 11, 12, 13, 14, 15, 16, 17, 18, 19, 20, 21, 22, 23, 31 or 32. In yet another aspect, the antibody-antigen complex further comprises a sequence tag used for purification of the complex. The skilled artisan will recognize that the antibody-antigen complex may be formed by covalent or non-covalent association between the DC-specific antibody or fragment and the antigen or in the form of a fusion protein, with either of the portions at the amino or carboxy-terminus or even as contactamers or one or more of either portion. In another aspect, the DC-specific antibody or fragment binds is selected from an antibody that specifically binds to MHC class I, MHC class II, CD1, CD2, CD3, CD4, CD8, CD11b, CD14, CD15, CD16, CD19, CD20, CD29, CD31, CD40, CD43, CD44, CD45, CD54, CD56, CD57, CD58, CD83, CD86, CMRF-44, CMRF-56, DCIR, DC-ASPGR, CLEC-6, CD40, BDCA-2, MARCO, DEC-205, mannose receptor, Langerin, DECTIN-1, B7-1, B7-2, IFN-γ receptor and IL-2 receptor, ICAM-1, Fcγ receptor, LOX-1, and ASPGR.

Yet another embodiment of the present invention is a vaccine comprising: a DC-specific antibody or fragment thereof to which an engineered Gag antigen is attached to form an antibody-antigen complex, wherein the Gag antigen is less susceptible to proteolytic degradation by eliminating one or more proteolytic sites; and a DC-specific antibody or fragment thereof to which an engineered Nef antigen is attached to form an antibody-antigen complex, wherein the Nef antigen comprises one or more codon usage optimization that increase antibody-antigen complex secretion, wherein the vaccine is able to elicit an HIV-specific T cell immune response to Gag p17, Gag p24 and Nef. In one aspect, the Gag and Nef antigens comprise a fusion protein. In another aspect, the Gag and Nef antigens comprise a fusion protein separated by one or more flexible linkers. In one aspect, the antibody-antigen complex further comprises a flexible linker between the DC-specific antibody or fragment thereof and the Gag or Nef antigen that comprises one or more linkers selected from SEQ ID NOS. 4 and 6. In one aspect, the antibody-antigen complex further comprises a flexible linker between the DC-specific antibody or fragment thereof and the Gag antigen that comprises one or more glycosylation sites selected from a linker sequence derived from a cellulose degrading organism. In one aspect, the DC-specific antibody or fragment thereof is humanized. In one specific aspect, the vaccine is selected from SEQ ID NOS: 1, 2, 3, 4, 5, 7, 8, 9, 10, 11, 12, 13, 14, 15, 16, 17, 18, 19, 20, 21, 22, 23, 31 or 32. In another aspect, the antibody-antigen complex further comprises a sequence tag used for purification of the complex.

In yet another embodiment, the present invention is a vaccine comprising a DC-specific antibody or fragment thereof to which an engineered Gag antigen is attached to form an antibody-antigen complex, wherein the Gag antigen is less susceptible to proteolytic degradation by eliminating one or more proteolytic sites; and an engineered Nef antigen that is attached to the DC-specific antibody or fragment thereof or to the engineered Gag antigen form an antibody-antigen complex, wherein the Nef antigen comprises one or more codon usage optimization that increase antibody-antigen complex secretion, wherein the vaccine is able to elicit an HIV-specific T cell immune response to Gag p17, Gag p24 and Nef. In one aspect, DC-specific antibody or fragment thereof the Gag and Nef antigens comprise a fusion protein. In one aspect, the Gag and Nef antigens comprise a fusion protein separated by one or more flexible linkers.

Yet another embodiment of the present invention includes a method for increasing the effectiveness of dendritic cells by isolating patient dendritic cells; exposing the dendritic cells to activating amounts of a vaccine comprising: a DC-specific antibody or fragment thereof to which an engineered Gag antigen is attached to form an antibody-antigen complex, wherein the Gag antigen is less susceptible to proteolytic degradation by eliminating one or more proteolytic sites; and an engineered Nef antigen that is attached to the DC-specific antibody or fragment thereof or to the engineered Gag antigen form an antibody-antigen complex, wherein the Nef antigen comprises one or more codon usage optimization that increase antibody-antigen complex secretion, wherein the vaccine is able to elicit an HIV-specific T cell immune response to Gag p17, Gag p24 and Nef; and reintroducing the antigen-loaded, activated dendritic cells into the patient.

Yet another embodiment of the present invention includes a vaccine comprising a DC-specific antibody or fragment thereof to which an engineered antigen comprising Cyclin D1 or fragments attached to form an antibody-antigen complex, wherein the Cyclin D1 antigen is less susceptible to proteolytic degradation by eliminating one or more proteolytic sites. In one aspect, the antibody-antigen complex further comprises a flexible linker between the DC-specific antibody or fragment thereof and the Cyclin D1 antigen. In another aspect, the antibody-antigen complex further comprises one or more new glycosylation sites. In yet another aspect, the antibody-antigen complex further comprises a flexible linker between the DC-specific antibody or fragment thereof and the Cyclin D1 antigen that comprises one or more glycosylation sites that provide increased flexibility between the antibody and the antigen, decreased proteolysis at the linker and increased secretion. For example, the antibody-antigen complex may further comprise a flexible linker between the DC-specific antibody or fragment thereof and the Cyclin D1 antigen that comprises one or more glycosylation sites selected from a linker sequence derived from a cellulose degrading organism. In one aspect, the DC-specific antibody or fragment thereof is humanized. In another aspect, the DC-specific antibody or fragment thereof is bound to one half of a Coherin/Dockerin pair and the engineered Cyclin D1 antigen is bound to the complementary half of the Coherin/Dockerin pair to form a complex. The present invention also includes a method for increasing the effectiveness of dendritic cells comprising: isolating patient dendritic cells; exposing the dendritic cells to activating amounts of a vaccine comprising: a DC-specific antibody or fragment thereof to which an engineered antigen comprising Cyclin D1 or fragment(s) thereof attached to form an antibody-antigen complex, wherein the Cyclin D1 antigen is less susceptible to proteolytic degradation by eliminating one or more proteolytic sites or introducing glycosylation sites or improving the expression by selecting one or more codons that improve expression; and reintroducing the antigen-loaded, activated dendritic cells into the patient.

Yet another embodiment of the present invention includes an isolated and purified nucleic acid that encodes a polypeptide selected from SEQ ID NO.: 1, 2, 3, 4, 5, 7, 8, 9, 10, 11, 12, 13, 14, 15, 16, 17, 18, 19, 20, 21, 22, 23, 31 or 32. Yet another embodiment of the present invention includes an isolated and purified polypeptide selected from SEQ ID NO.: 1, 2, 3, 4, 5, 7, 8, 9, 10, 11, 12, 13, 14, 15, 16, 17, 18, 19, 20, 21, 22, 23, 31 or 32.

BRIEF DESCRIPTION OF THE DRAWINGS

For a more complete understanding of the features and advantages of the present invention, reference is now made to the detailed description of the invention along with the accompanying figures and in which:

FIG. 1 shows a Coomassie Blue stained reduced SDS PAGE analysis of protein A affinity chromatography purified gag p24-antibody fusion proteins obtained from CHO-S or 293F cells transiently transfected with expression vectors encoding the H chain-gag p24 fusion, with diagrams of the constructs and expected molecular weights.

FIG. 2 shows a Coomassie Blue stained reduced SDS PAGE analysis of protein A affinity chromatography purified gag p24 antibody fusion protein obtained from CHO-S or 293F cells transiently transfected with expression vectors encoding a H chain-gag p24 fusion with a H chain-gag p24 linker derived from cellulosomal anchoring scaffoldin B precursor [*Bacteroides cellulosolvens*] and a corresponding light [L] chain expression plasmid, with diagrams of the constructs and expected glycosylation sites and molecular weights.

FIGS. 3A to 3C show the structural domain schema for cipA.

FIGS. 4A to 4C show the structural domain scheme for cellulosomal anchoring scaffoldin B precursor [*Bacteroides cellulosolvens]*.

FIG. 5 shows a gel with the approximate position expected for the C535-encoded H chain, with diagrams of the constructs and expected molecular weights.

FIG. 6 shows a gel of the partially purified product of expression of [mAnti-DCIR_9E8_H-LV-hIgG4H-C-Flex-var1-Viralgag-p40-var1-6×His] C601 co-transfected with the appropriate L chain expression plasmid, with diagrams of the constructs and expected glycosylation sites and molecular weights.

FIG. 7 shows various H chain-antigen constructs transiently co-transfected into 293F cells with identical appropriate L chain expression constructs, with diagrams of the constructs and expected glycosylation sites and molecular weights.

FIG. 8 is a graph from a screen to detect the subset of anti-CD40 antibodies that can bind and activate CD40.

FIG. 9 shows FACS analysis of CD8+ staining [horizontal axis] versus Flu M1-tetramer staining [vertical axis] as elicited by a dose range from 10 ug/ml to no anti-CD4012E12-hIgG4 Dockerin-Cohesin Flu M1 conjugate.

Figure 20:
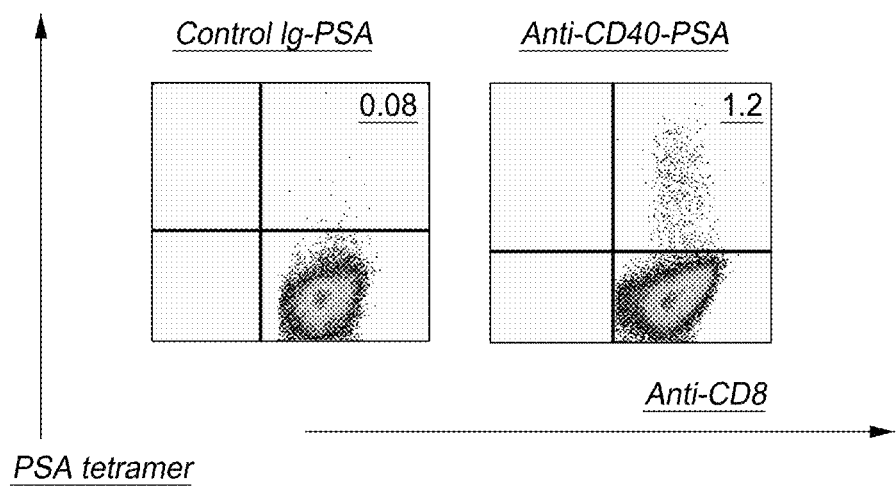

FIG. 20 shows that DCs targeted with anti-CD40-PSA targeted to DCs induce PSA-specific CD8+ T cell responses. IFNDCs were targeted with 1 µg mAb fusion protein with PSA. Purified autologous CD8+ T cells were co-cultured for 10 days. Cells were stained with anti-CD8 and PSA (KLQCVDLHV)-tetramer. Cells are from a HLA-A*0201 positive healthy donor. The results demonstrate that anti-CD40 effectively delivers PSA to the DC, which in turn elicit the expansion of PSA-specific CD8+ T cells.

Figure 21:
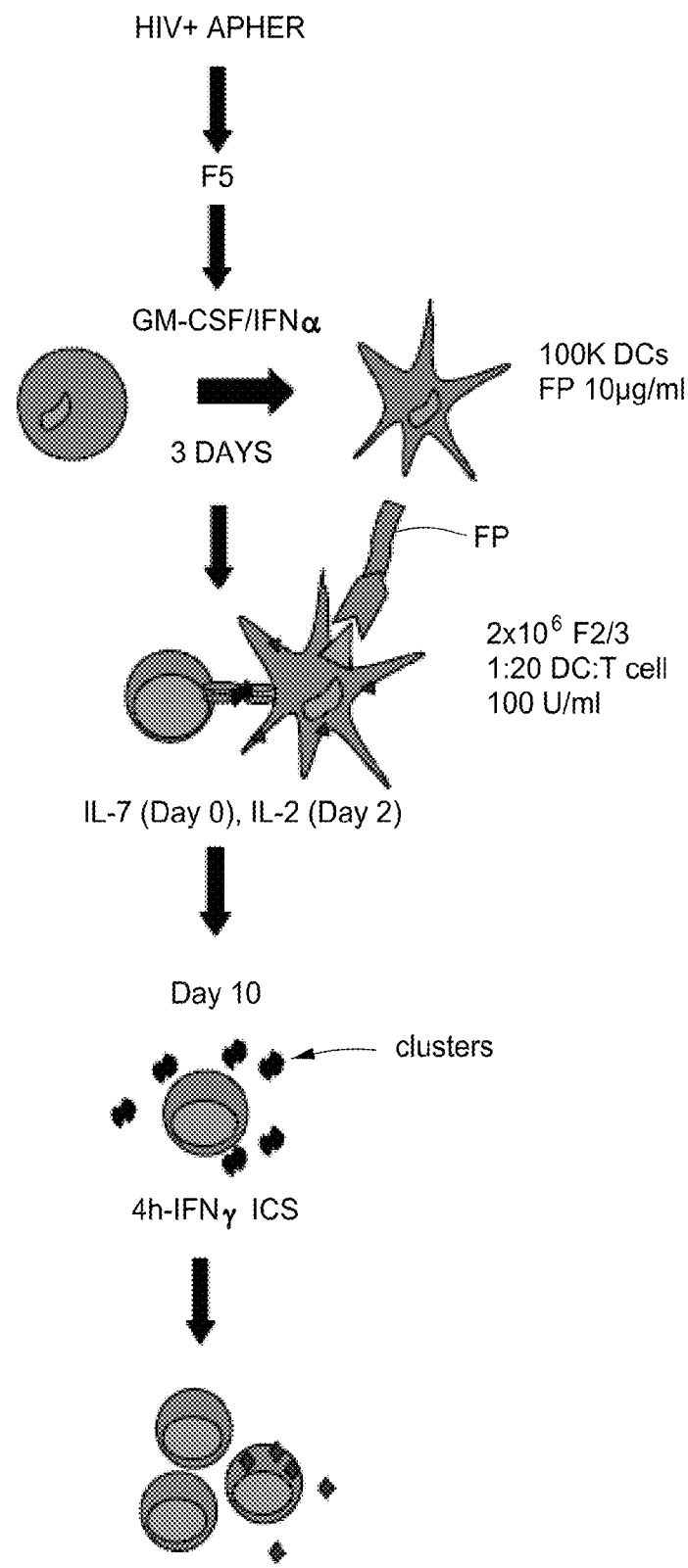

FIG. 21 outlines the DC targeting protocol for testing anti-DC receptor targeting vaccines for their ability to direct the expansion of antigen-specific T cells resulting from targeted uptake by the DC and presentation of antigen epitopes on their cell surface.

Figure 22:
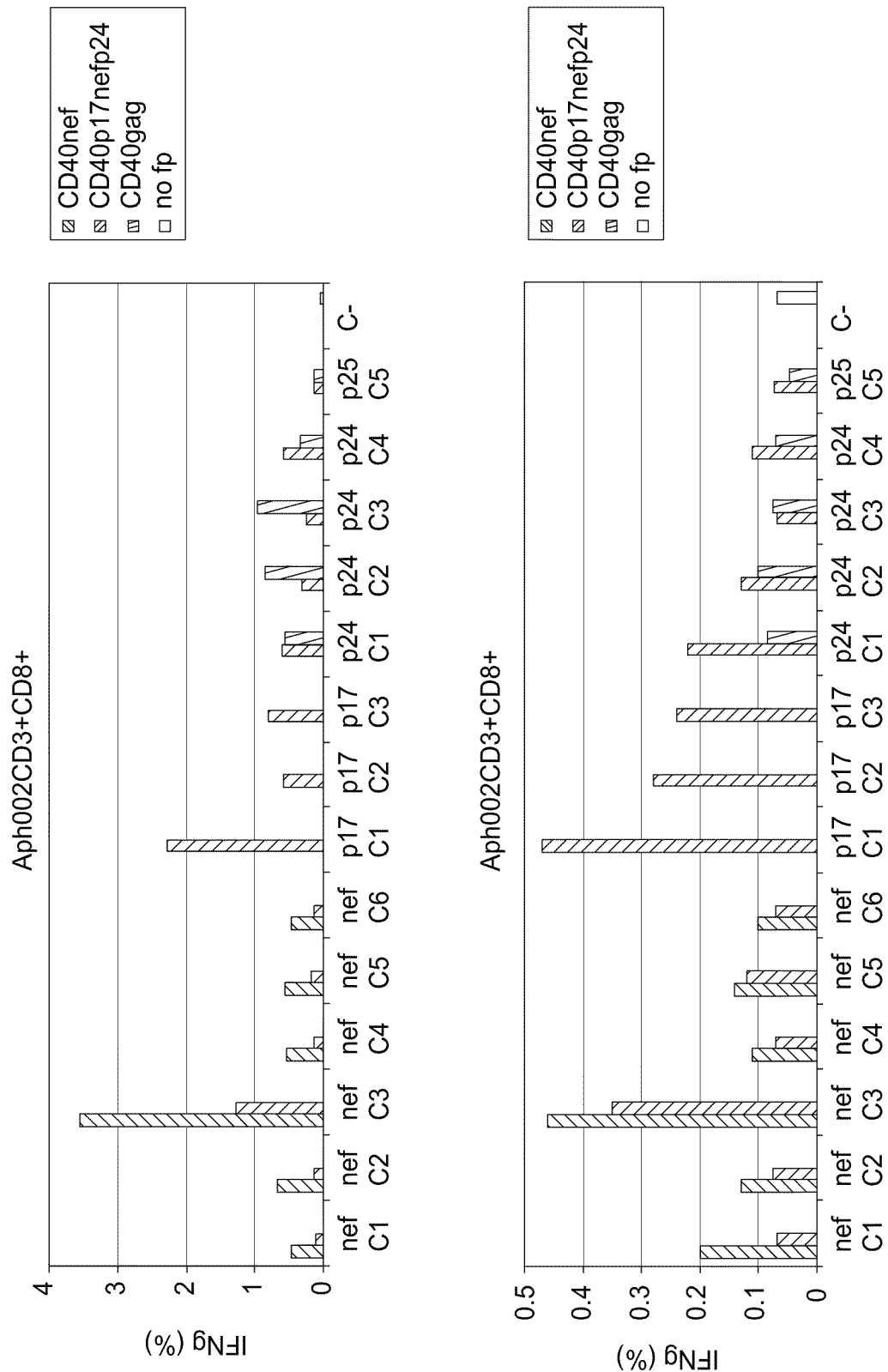

FIG. 22 [upper panel] shows comparison of the efficacy of anti-CD4012E12 nef, anti-CD4012E12 gag p24, and anti-CD4012E12 gag p17 nef gag p24 vaccines [patient Aph002].

FIG. 22 [lower panel] shows comparison of the efficacy of anti-CD4012E12 nef, anti-CD4012E12 gag p24, and anti-CD4012E12 gag p17 nef gag p24 vaccines [patient Aph002].

Figure 23:
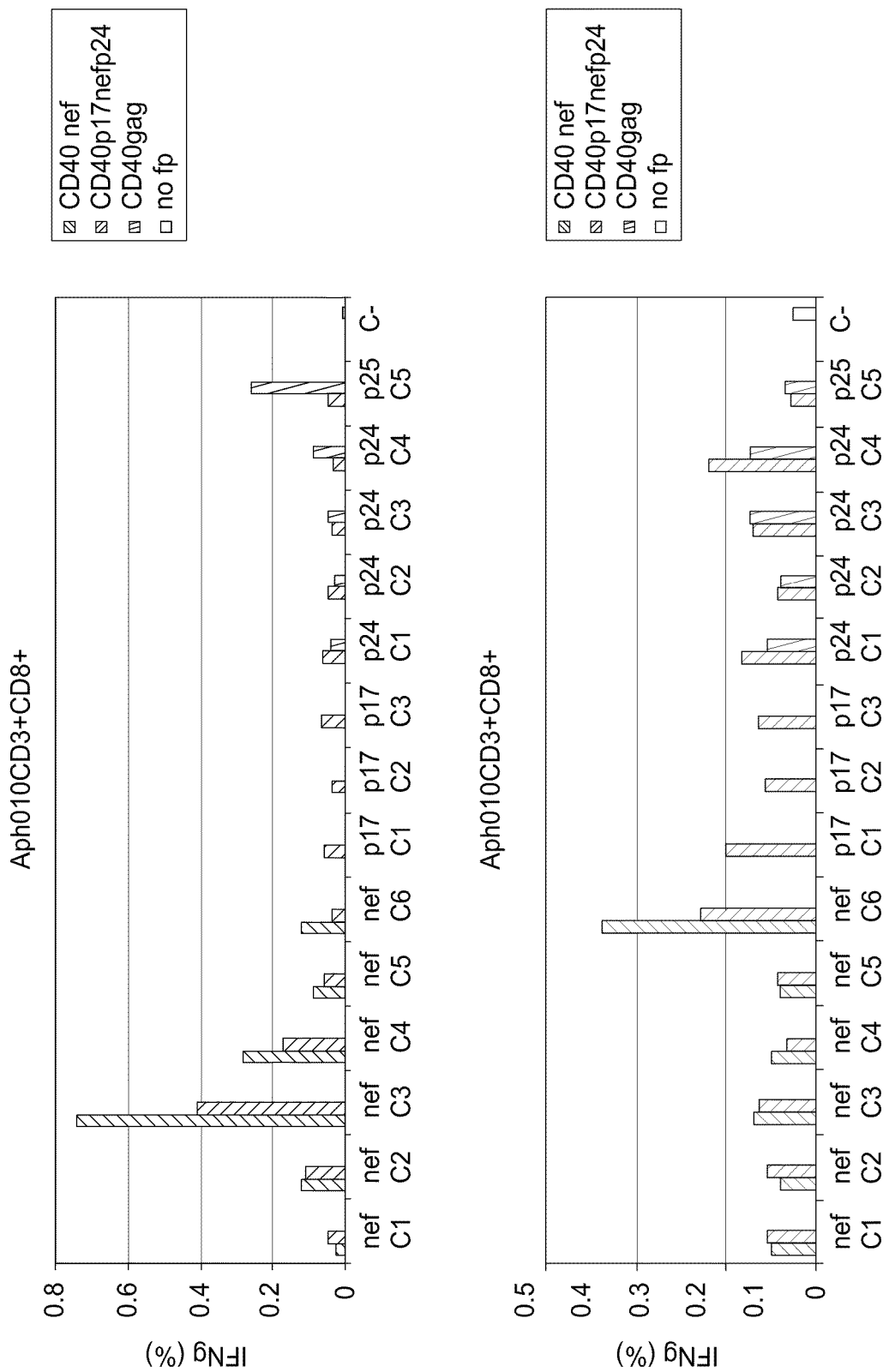

FIG. 23 [upper panel] shows comparison of the efficacy of anti-CD4012E12 nef, anti-CD4012E12 gag p24, and anti-CD4012E12 gag p17 nef gag p24 vaccines [patient Aph010].

FIG. 23 [lower panel] shows comparison of the efficacy of anti-CD4012E12 nef, anti-CD4012E12 gag p24, and anti-CD4012E12 gag p17 nef gag p24 vaccines [patient Aph002].

Figure 24:
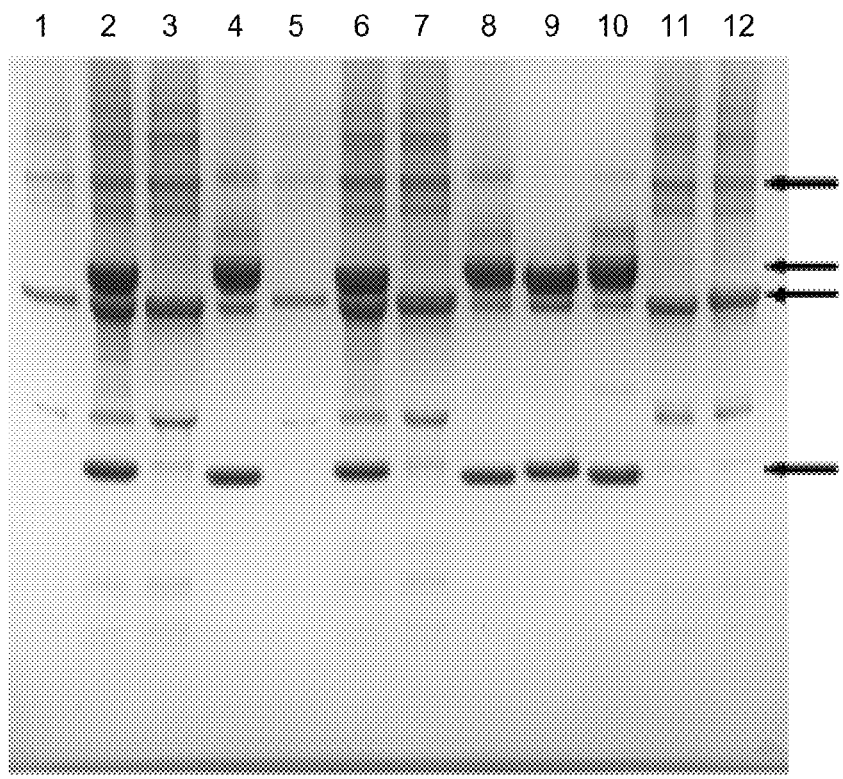

FIG. 24 is a gel that shows an analysis of the interaction of Cohesin-Cyclin D1 fusion protein with anti-DC receptor-Dockerin recombinant antibody.

Figure 25:
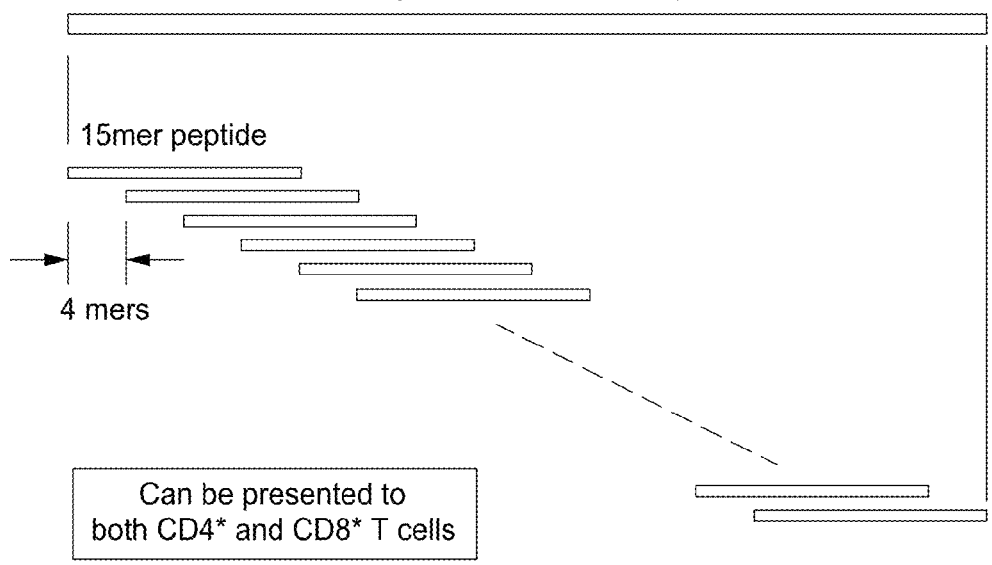

FIG. 25 shows schema of overlapping peptides from Cyclin D1.

Figure 26:
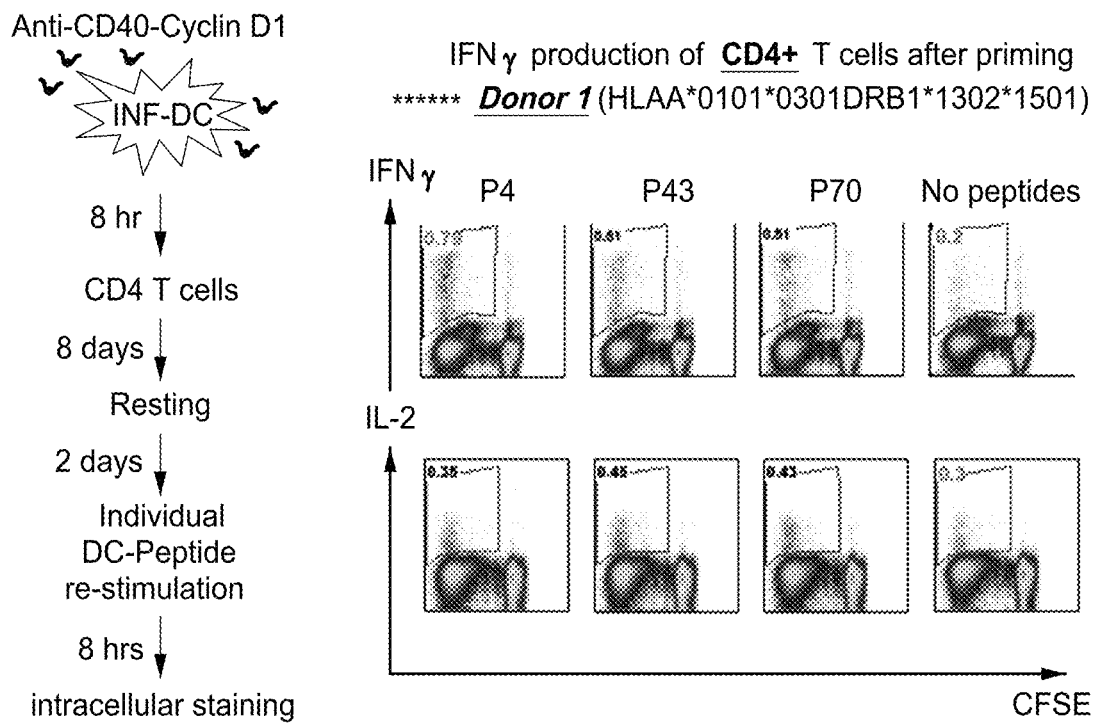

FIG. 26 shows a schema (left) of the study design for testing the ability of anti-CD40-Cyclin D1 complexes to elicit expansion in vitro of Cyclin D1-specific CD4+ T cells, and the FACS results obtained thereby (right).

Figure 27:
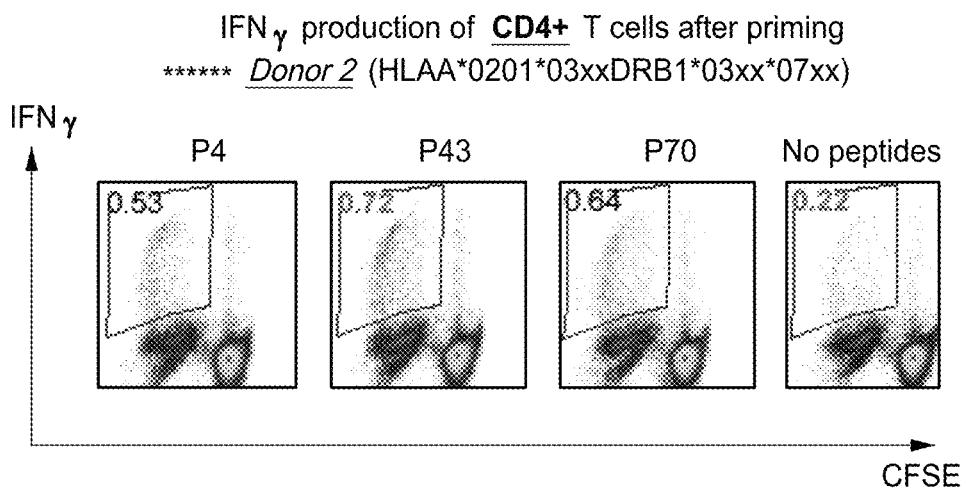

FIG. 27 is a FACS analysis similar to that detailed in FIG. 26, with a different normal donor—in this case the anti-CD40-Cyclin D1 complex elicited the expansion of IFNg positive proliferating CD4+ T cells specific for Cyclin D1 peptides P4, P43, and P70.

Figure 28:
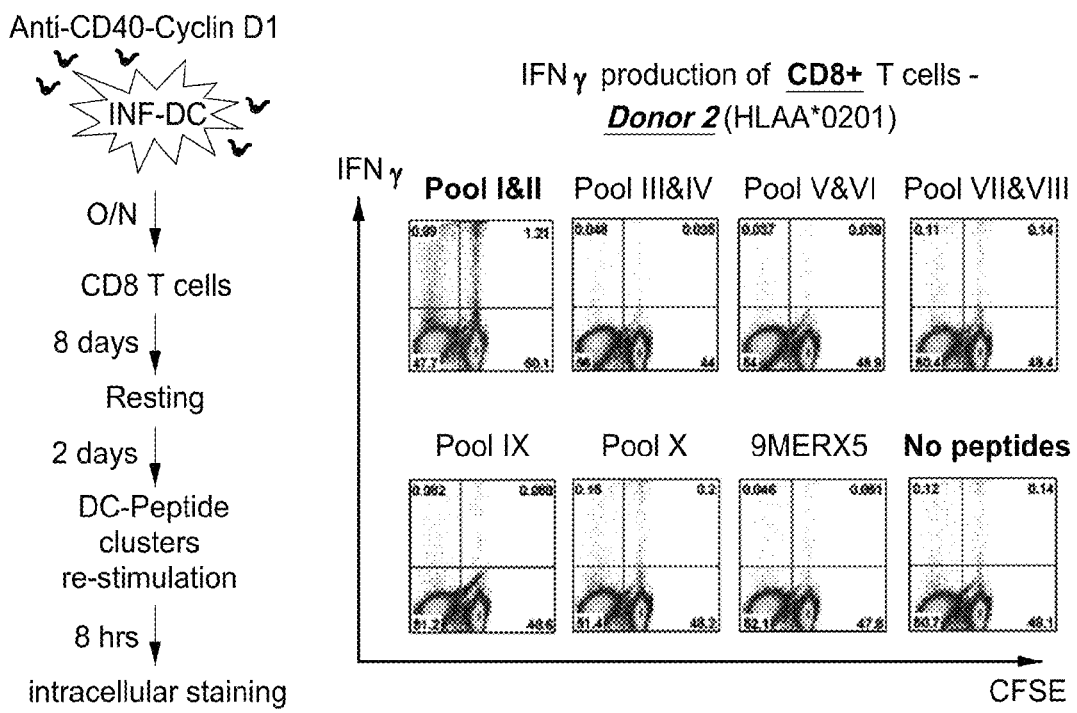

FIG. 28 shows a schema (left) and analysis (right) similar to that shown in FIG. 26, except that CD8+ T cells were used.

Figure 29:
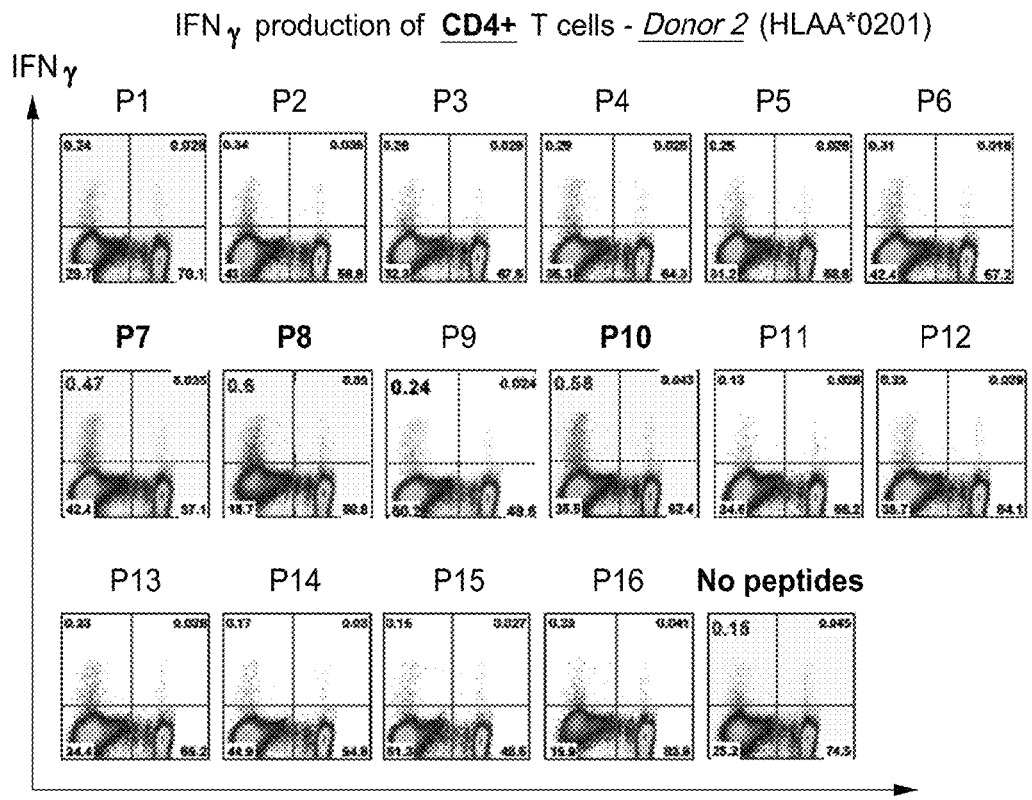

FIG. 29 shows similar data from the same donor as FIG. 28, but analyzed with individual peptides from pools of peptides.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Dendritic cells (DCs) are antigen-presenting cells that play a key role in regulating antigen-specific immunity (Mellman and Steinman 2001), (Banchereau, Briere et al. 2000), (Cella, Sallusto et al. 1997). DCs capture antigens, process them into peptides, and present these to T cells. Therefore delivering antigens directly to DC is a focus area for improving vaccines. One such example is the development of DC-based vaccines using ex-vivo antigen-loading of autologous DCs that are then re-administrated to patients (Banchereau, Schuler-Thurner et al. 2001), (Steinman and Dhodapkar 2001). Another strategy to improve vaccine efficacy is specific targeting to DC of antigen conjugated to antibodies against internalizing DC-specific receptors. The potential of targeting DC for vaccination is highlighted by key mouse studies. In vivo, targeting with an anti-LOX-1 mAb coupled to ovalbumin (OVA) induced a protective CD8+ T cell response, via exogenous antigen cross-presentation toward the MHC class I pathway (Delneste, Magistrelli et al. 2002). Also, OVA conjugated to anti-DEC205 mAb in combination with a CD40L maturation stimulus enhanced the MHC class I-restricted presentation by DCs in vivo and led to the durable formation of effector memory CD8+ T cells (Bonifaz, Bonnyay et al. 2004). Both these studies showed dramatic dose-sparing (i.e., strong immune-responses at very low antigen doses) and suggested broader responses than normally seen with other types of OVA immunization. Recent work with targeting of HIV gag antigen to DC via DEC205 has extended these concepts to a clinically relevant antigen and confirmed the tenents of targeting antigen to DC—dramatic dose-sparing, protective responses from a single vaccination, and expansion of antigen-specific T cells in both the CD8 and CD4 compartments (Trumpfheller, Finke et al. 2006).

The present invention provides for the complexing of multiple antigens or proteins (engineered, expressed, and purified independently from the primary mAb) in a controlled, multivariable fashion, to one single primary recombinant mAb. Presently, there are methods for engineering site-specific biotinylation sites that provide for the addition of different proteins (each engineered separately linked to streptavidin) to the one primary mAb. However, the present invention provides for addition to the primary mAb of multiple combinations, in fixed equimolar ratios and locations, of separately engineered proteins.

As used herein, the term "antibody or fragment thereof" is used to describe a recombinant antibody system that has been engineered to provide a target specific antibody. The monoclonal antibody made using standard hybridoma techniques, recombinant antibody display, humanized monoclonal antibodies and the like. The antibody can be used to, e.g., target (via one primary recombinant antibody against an internalizing receptor, e.g., a human dendritic cell receptor) multiple antigens and/or antigens and an activating cytokine to dendritic cells (DC).

The antigen binding portion of the antibody includes on or more fragments (i.e., the fragments thereof) that may include one or more variable domains, one or more variable and the first constant domain, an Fab fragment, a Fab' fragment, an F(ab)$_2$ fragment, and Fv fragment, and Fabc fragment and/or a Fab fragment with portions of the Fc domain to which the cognate modular binding portions are added to the amino acid sequence and/or bound. The antibody for use can be of any isotype or class, subclass or from any source (animal and/or recombinant). In certain aspects, the antigen binding sites are derived from non-human monoclonal antibodies that are grafted, using techniques well known in the art, onto a human antibody backbone thereby "humanizing" the antibody.

The term "antigen" as used herein refers to a molecule that can initiate a humoral and/or cellular immune response in a recipient of the antigen. Antigen may be used in two different contexts with the present invention: as a target for the antibody or other antigen recognition domain of the engineered or recombinant antibody (rAb) or as the molecule that is carried to and/or into a cell or target by the rAb as a conjugate (bound covalent or non-covalently) or a fusion protein. The antigen is usually an agent that causes a disease for which a vaccination would be advantageous treatment. When the antigen is presented on MHC, the peptide is often about 8 to about 25 amino acids. Antigens include any type of biologic molecule, including, for example, simple intermediary metabolites, sugars, lipids and hormones as well as macromolecules such as complex carbohydrates, phospholipids, nucleic acids and proteins. Common categories of antigens include, but are not limited to, viral antigens, bacterial antigens, fungal antigens, protozoal and other parasitic antigens, tumor antigens, antigens involved in autoimmune disease, allergy and graft rejection, and other miscellaneous antigens. The present invention uses antigens from viruses that have improved characteristics (e.g., decreased proteolysis, enhanced secretion, enhanced expression or stability) and that are targeted to antigen presenting cells using the antibody or fragments thereof.

Examples of viral antigens include, but are not limited to, e.g., retroviral antigens such as retroviral antigens from the human immunodeficiency virus (HIV) antigens such as gene products of the gag, pol, and env genes, the Nef protein, reverse transcriptase, and other HIV components; hepatitis viral antigens such as the S, M, and L proteins of hepatitis B virus, the pre-S antigen of hepatitis B virus, and other hepatitis, e.g., hepatitis A, B, and C, viral components such as hepatitis C viral RNA; influenza viral antigens such as hemagglutinin and neuraminidase and other influenza viral components; measles viral antigens such as the measles virus fusion protein and other measles virus components; rubella viral antigens such as proteins E1 and E2 and other rubella virus components; rotaviral antigens such as VP7sc and other rotaviral components; cytomegaloviral antigens such as envelope glycoprotein B and other cytomegaloviral antigen components; respiratory syncytial viral antigens such as the RSV fusion protein, the M2 protein and other respiratory syncytial viral antigen components; herpes simplex viral antigens such as immediate early proteins, glycoprotein D, and other herpes simplex viral antigen components; varicella zoster viral antigens such as gpI, gpII, and other varicella zoster viral antigen components; Japanese encephalitis viral antigens such as proteins E, M-E, M-E-NS1, NS1, NS1-NS2A, 80% E, and other Japanese encephalitis viral antigen components; rabies viral antigens such as rabies glycoprotein, rabies nucleoprotein and other rabies viral antigen components. See Fundamental Virology, Second Edition, eds. Fields, B. N. and Knipe, D. M. (Raven Press, New York, 1991) for additional examples of viral antigens.

Antigenic targets that may be delivered using the rAb-DC/DC-antigen vaccines of the present invention include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenavirus, reovirus, retrovirus, papilomavirus, parvovirus, herpesvirus, poxvirus, hepadnavirus, and spongiform virus. Other viral targets include influenza, herpes simplex virus 1 and 2, measles, dengue, smallpox, polio or HIV. Pathogens include trypanosomes, tapeworms, roundworms, helminthes, malaria. Tumor markers, such as fetal antigen or prostate specific antigen, may be targeted in this manner. Other examples include: HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. In some cases, vaccination of an individual may only be required infrequently, such as yearly or biennially, and provide long term immunologic protection against the infectious agent. Specific examples of organisms, allergens and nucleic and amino sequences for use in vectors and ultimately as antigens with the present invention may be found in U.S. Pat. No. 6,541,011, relevant portions incorporated herein by reference, in particular, the tables that match organisms and specific sequences that may be used with the present invention.

Antigens on the surface of immune cells, e.g., antigen presenting cells or dendritic cells, which can be targeted using the rAb of the present invention will generally be selected based on a number of factors, including: likelihood of internalization, level of immune cell specificity, type of immune cell targeted, level of immune cell maturity and/or activation and the like. Examples of cell surface markers for dendritic cells include, but are not limited to, MHC class I, MHC Class II, B7-2, CD18, CD29, CD31, CD43, CD44, CD45, CD54, CD58, CD83, CD86, CMRF-44, CMRF-56, DCIR and/or ASPGR and the like; while in some cases also having the absence of CD2, CD3, CD4, CD8, CD14, CD15, CD16, CD 19, CD20, CD56, and/or CD57. Examples of cell surface markers for antigen presenting cells include, but are not limited to, MHC class I, MHC Class II, CD40, CD45, B7-1, B7-2, IFN-γ receptor and IL-2 receptor, ICAM-1, Fcγ receptor. LOX-1 or ASPGR. Examples of cell surface markers for T cells include, but are not limited to, CD3, CD4, CD8, CD 14, CD20, CD11b, CD16, CD45 and HLA-DR.

As used herein, the term "epitope(s)" refer to a peptide or protein antigen that includes a primary, secondary or tertiary structure similar to an epitope located within any of a number of pathogen polypeptides encoded by the pathogen DNA or RNA. The level of similarity will generally be to such a degree that monoclonal or polyclonal antibodies directed against such polypeptides will also bind to, react with, or otherwise recognize, the peptide or protein antigen. Various immunoassay methods may be employed in conjunction with such antibodies, such as, for example, Western blotting, ELISA, RIA, and the like, all of which are known to those of skill in the art. The identification of pathogen epitopes, and/or their functional equivalents, suitable for use in vaccines is part of the present invention. Once isolated and identified, one may readily obtain functional equivalents. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')$_2$, Fv, and other fragments that exhibit immunological binding properties of the parent monoclonal antibody molecule.

As used herein, the term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" (FRs). As used herein, the term "FR" refers to amino acid sequences which are found naturally between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "humanized" antibody refers to those molecules comprising an antigen-binding site derived from a non-human immunoglobulin have been described, including chimeric antibodies having rodent V regions and their associated CDRs fused to human constant domains, rodent CDRs grafted into a human supporting FR prior to fusion with an appropriate human antibody constant domain, and rodent CDRs supported by recombinantly veneered rodent FRs. These "humanized" molecules are designed to minimize unwanted immunological response toward rodent antihuman antibody molecules, which limits the duration and effectiveness of therapeutic applications of those moieties in human recipients.

The preparation of vaccine compositions that includes the nucleic acids that encode antigens of the invention as the active ingredient, may be prepared as injectables, either as liquid solutions or suspensions; solid forms suitable for solution in, or suspension in, liquid prior to infection can also be prepared. The preparation may be emulsified, encapsulated in liposomes. The active immunogenic ingredients are often mixed with carriers which are pharmaceutically acceptable and compatible with the active ingredient.

The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants that may be effective include but are not limited to: aluminum hydroxide, N-acetyl-muramyl-L-threonyl-D-isoglutamine (thr-MDP), N-acetyl-nor-muramyl-L-alanyl-D-isoglutamine, MTP-PE and RIBI, which contains three components extracted from bacteria, monophosphoryl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-γ, IL-2 and IL-12) or synthetic IFN-γ inducers such as poly I:C can be used in combination with adjuvants described herein.

Pharmaceutical products that may include a naked polynucleotide with a single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form. Another pharmaceutical product that may spring from the current invention may include a highly purified plasma lipoprotein fraction, isolated according to the methodology, described herein from either the patients blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may include a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition that includes the naked polynucleotide prebound to a highly purified lipoprotein fraction may be administered in amounts ranging from 1 µg to 1 mg polynucleotide and 1 µg to 100 mg protein.

Administration of vaccine to a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention may include an effective amount of the compound, dissolved or dispersed in a pharmaceutically acceptable carrier or aqueous medium. Such compositions can also be referred to as inocula. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions. The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

Disease States. Depending on the particular disease to be treated, administration of therapeutic compositions according to the present invention will be via any common route so long as the target tissue is available via that route in order to maximize the delivery of antigen to a site for maximum (or in some cases minimum) immune response. Administration will generally be by orthotopic, intradermal, subcutaneous, intramuscular, intraperitoneal or intravenous injection. Other areas for delivery include: oral, nasal, buccal, rectal, vaginal or topical. Topical administration would be particularly advantageous for treatment of skin cancers. Such compositions would normally be administered as pharmaceutically acceptable compositions that include physiologically acceptable carriers, buffers or other excipients.

Vaccine or treatment compositions of the invention may be administered parenterally, by injection, for example, either subcutaneously or intramuscularly. Additional formulations which are suitable for other modes of administration include suppositories, and in some cases, oral formulations or formulations suitable for distribution as aerosols. In the case of the oral formulations, the manipulation of T-cell subsets employing adjuvants, antigen packaging, or the addition of individual cytokines to various formulation that result in improved oral vaccines with optimized immune responses. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%-95% of active ingredient, preferably 25-70%.

The antigen encoding nucleic acids of the invention may be formulated into the vaccine or treatment compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine or treatment compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms active ingredient per vaccination with a range from about 0.1 mg to 1000 mg, such as in the range from about 1 mg to 300 mg, and preferably in the range from about 10 mg to 50 mg. Suitable regiments for initial administration and booster shots are also variable but are typified by an initial administration followed by subsequent inoculations or other administrations. Precise amounts of active ingredient required to be administered depend on the judgment of the practitioner and may be peculiar to each subject. It will be apparent to those of skill in the art that the therapeutically effective amount of nucleic acid molecule or fusion polypeptides of this invention will depend, inter alia, upon the administration schedule, the unit dose of antigen administered, whether the nucleic acid molecule or fusion polypeptide is administered in combination with other therapeutic agents, the immune status and health of the recipient, and the therapeutic activity of the particular nucleic acid molecule or fusion polypeptide.

The compositions can be given in a single dose schedule or in a multiple dose schedule. A multiple dose schedule is one in which a primary course of vaccination may include, e.g., 1-10 separate doses, followed by other doses given at subsequent time intervals required to maintain and or reinforce the immune response, for example, at 1-4 months for a second dose, and if needed, a subsequent dose(s) after several months. Periodic boosters at intervals of 1-5 years, usually 3 years, are desirable to maintain the desired levels of protective immunity. The course of the immunization can be followed by in vitro proliferation assays of peripheral blood lymphocytes (PBLs) co-cultured with ESAT6 or ST-CF, and by measuring the levels of IFN-γ released from the primed lymphocytes. The assays may be performed using conventional labels, such as radionucleotides, enzymes, fluorescent labels and the like. These techniques are known to one skilled in the art and can be found in U.S. Pat. Nos. 3,791,932, 4,174,384 and 3,949,064, relevant portions incorporated by reference.

The vaccine of the present invention may be provided in one or more "unit doses" depending on whether the nucleic acid vectors are used, the final purified proteins, or the final vaccine form is used. Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. The subject to be treated may also be evaluated, in particular, the state of the subject's immune system and the protection desired. A unit dose need not be administered as a single injection but may include continuous infusion over a set period of time. Unit dose of the present invention may conveniently may be described in terms of DNA/kg (or protein/Kg) body weight, with ranges between about 0.05, 0.10, 0.15, 0.20, 0.25, 0.5, 1, 10, 50, 100, 1,000 or more mg/DNA or protein/kg body weight are administered. Likewise the amount of rAb-DC/DC-antigen vaccine delivered can vary from about 0.2 to about 8.0 mg/kg body weight. Thus, in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of the vaccine may be delivered to an individual in vivo. The dosage of vaccine to be administered depends to a great extent on the weight and physical condition of the subject being treated as well as the route of administration and the frequency of treatment. A pharmaceutical composition that includes a naked polynucleotide prebound to a liposomal or viral delivery vector may be administered in amounts ranging from 1 µg to 1 mg polynucleotide to 1 µg to 100 mg protein. Thus, particular compositions may include between about 1 µg, 5 µg, 10 µg, 20 µg, 30 µg, 40 µg, 50 µg, 60 µg, 70 µg, 80 µg, 100 µg, 150 µg, 200 µg, 250 µg, 500 µg, 600 µg, 700 µg, 800 µg, 900 µg or 1,000 µg polynucleotide or protein that is bound independently to 1 µg, 5 µg, 10 µg, 20 µg, 3.0 µg, 40 µg 50 µg, 60 µg, 70 µg, 80 µg, 100 µg, 150 µg, 200 µg, 250 µg, 500 µg, 600 µg, 700 µg, 800 µg, 900 µg, 1 mg, 1.5 mg, 5 mg, 10 mg, 20 mg, 30 mg, 40 mg, 50 mg, 60 mg, 70 mg, 80 mg, 90 mg or 100 mg vector.

The present invention may also be used to make a modular rAb carrier that is, e.g., a recombinant humanized mAb (directed to a specific human dendritic cell receptor) complexed with protective antigens from Ricin, Anthrax toxin, and *Staphylococcus* B enterotoxin. The potential market for this entity is vaccination of all military personnel and stored vaccine held in reserve to administer to large population centers in response to any biothreat related to these agents. The invention has broad application to the design of vaccines in general, both for human and animal use. Industries of interest include the pharmaceutical and biotechnology industries.

The present invention includes compositions and methods, including vaccines, that specifically target (deliver) antigens to antigen-presenting cells (APCs) for the purpose of eliciting potent and broad immune responses directed against the antigen. These compositions evoke protective or therapeutic immune responses against the agent (pathogen or cancer) from which the antigen was derived. In addition the invention creates agents that are directly, or in concert with other agents, therapeutic through their specific engagement with antigen-presenting cells.

Gag-Nef vaccine. The sequence shown below is a heavy chain (H)-HIV gag p24 fusion protein where the p24 region [italicized] is linked to the C-terminus of hIgG4H via a short spacer [bold] derived from a flexible loop of human major histocompatibility complex, class II, DR alpha precursor. Underlined AS residues are encoded by restriction sites used for construction purposes [in this case Nhe I]. This type of antibody-p24 fusion protein has been described in the scientific literature [e.g., Antigen targeting to dendritic cells elicits long-lived T cell help for antibody responses (2006) Boscardin et al., JEM, Volume 203, Number 3, 599-606].

Improved antibody-antigen linker sequences. [mAnti-DCIR_9E8_H-LV-hIgG4H-Viralgag] C241 is:

(SEQ ID NO.: 1)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKA<u>S</u>DMAKKETVWRLEEFGR<i>PIVQNIQGQMVHQAISPRTLNAWVKVVEEK

AFSPEVIPMFSALSEGATPQDLNTMLNTVGGHQAAMQMLKETINEEAAEW

DRVHPVHAGPIAPGQMREPRGSDIAGTTSTLQEQIGWMTNNPPIPVGEIY

KRWIILGLNKIVRMYSPTSILDIRQGPKEPFRDYVDRFYKTLRAEQASQE

VKNWMTETLLVQNANPDCKTILKALGPAATLEEMMTACQGVGGPGHKARV</i>

L

Figure 1:
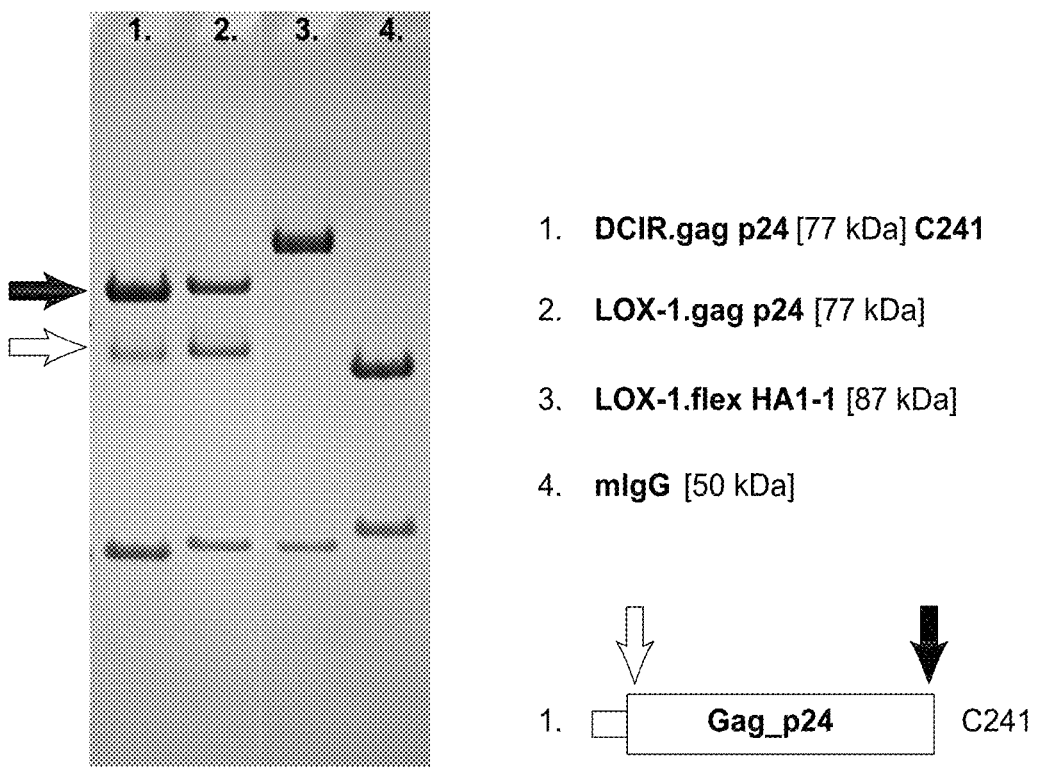
Figure 2:
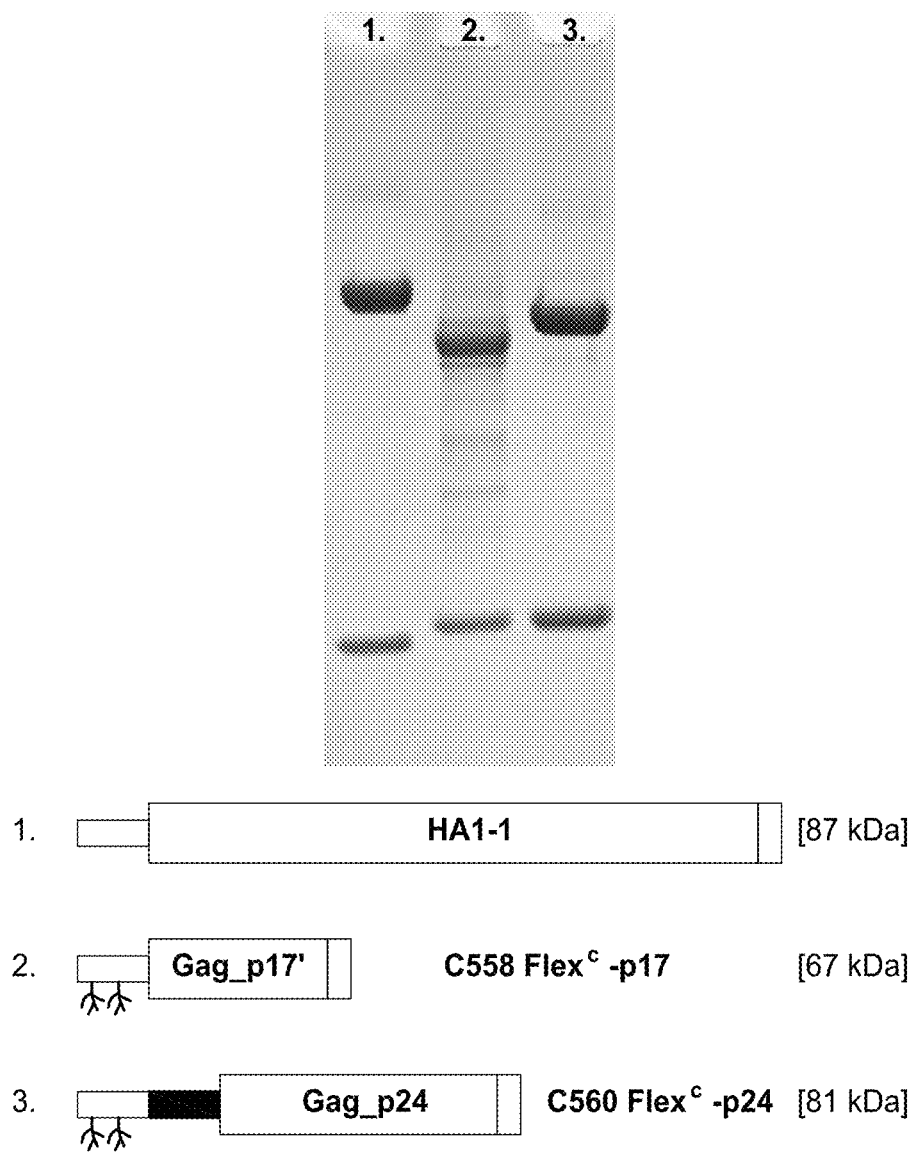

FIG. 1, lanes 1 and 2 show Coomassie Blue stained reduced SDS PAGE analysis of protein A affinity chromatography purified gag p24-antibody fusion proteins obtained from CHO-S or 293F cells transiently transfected with expression vectors encoding the H chain-gag p24 fusion [encoding e.g., C241 above preceded by a native signal sequence] and a corresponding light chain [L] expression plasmid. Typically for secreted protein production, the co-transfection culture proceeds for up to several days before harvesting culture supernatant for subsequent purification. The full length [~77 kDa] H chain-gag p24 fusion chain is indicated by the upper arrow. Also shown is a cleaved H chain product [lower arrow] that migrates slightly more slowly than a H chain not fused to another protein [shown in lane 4 as a ~50 kDa band]. This result suggests that the H chain-p24 linker sequence is susceptible to proteolytic cleavage, thus compromising the integrity of the produced secreted antibody-antigen fusion protein.

In contrast, an antibody-Influenza HA1-1 fusion protein can be secreted and recovered without significant observed cleavage between the H chain C-terminus and the HA1-1 domain. [mAnti-LOX-115C4H-LV-hIgG4H-C-Flex-FluHA1-1-6×His] C114 is:

(SEQ ID NO.: 2)
EIQLQQTGPELVKPGASVKISCKASGYPFTDYIMVWVKQSHGKSLEWIGN

ISPYYGTTNYNLKFKGKATLTVDKSSSTAYMQLNSLTSEDSAVYYCARSP

NWDGAWFAHWGQGALVTVSAAKTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFEGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK<u>ASD</u>
TTEPATPTTPVTT*DTICIGYHANNSTDTVDTVLEKNVTVTHSVNLLEDSH*

*NGKLCRLKGIAPLQLGKCNIAGWLLGNPECDPLLPVRSWSYIVETPNSEN*

*GICYPGDFIDYEELREQLSSVSSFERFEIFPKESSWPNHNTNGVTAACSN*

*EGKSSFYRNLLWLTEKEGSYPKLKNSYVNKKGKEVLVLWGIHHPPNSKEQ*

*QNLYQNENAYVSVVTSNYNRRFTPEIAERPKVRDQAGRMNYYWTLLKPGD*

*TIIFEANGNLIAPMYAFALSRGFGSGIITSNASMHECNTKCQTPLGAINS*

*SLPYQNIHPVTIGECLKYVRSAKLRMVHHHHHH*

In this case, a short linker [bold] derived from cellulosomal anchoring scaffoldin B precursor [CipA from *Clostridium thermocellum* ATCC 27405]] was inserted between the H chain C-terminus [via a joining sequence shown underlined] and the influenza HA1-1 domain [italicized]. There is no obvious proteolytic cleavage between the H chain C-terminus and the HA1-1 domain [FIG. 1 lane 3].

FIG. 2 lane 3 shows Coomassie Blue stained reduced SDS PAGE analysis of protein A affinity chromatography purified gag p24 antibody fusion protein obtained from CHO-S or 293F cells transiently transfected with expression vectors encoding a H chain-gag p24 fusion with a H chain-gag p24 linker derived from cellulosomal anchoring scaffoldin B precursor [*Bacteroides cellulosolvens*] and a corresponding light [L] chain expression plasmid.

[mAnti-DCIR_9E8_H-LV-hIgG4H-C-Flex-var1-Viral-gag-var1-6×His] C560 is shown below [underlined residues are from restriction site joining sequences and in bold are the flexible linker residues]:

(SEQ ID NO.: 3)

QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASQTPTNTISVTPTNNSTPTNNSNPKPNPASVDSEF*AQQAAADTGHSN*

*QVSQNYPIVQNIQGQMVHQAISPRTLNAWVKVVEEKAESREVIPMFSALS*

-continued

*EGATPQDLNTMLNTVGGHQAAMQMLKETINEEAAEWDRVHPVHAGPIAPG*

*QMREPRGSDIAGTTSTLQEQIGWMTHNPPIPVGEIYKRWIILGLNKIVRM*

*YSPTSILDIRQGPKEPERDYVDREYKTLRAEQASQEVKNWMTETLLVQNA*

*NPDCKTILKALGPGATLEEMMTACQGVG*HHHHHH

The above antibody-gag p24 fusion protein is produced intact with no detectable cleavage between the H chain C-terminus and the gag p24 domain. Thus, the QTPTNTISVTPTNNSTPTNNSNPKPNP (SEQ ID NO.: 4) linker sequence is superior for gag p24 vaccine production purposes.

Preferred linker sequences derived from Scaffoldins and related proteins. The sequence below is CipA—a scaffoldin from a cellulose-degrading bacterium. This protein contains multiple Cohesin domains interspersed with linker sequences [italicized] apparently evolved to be flexible—reflecting the role of this protein to: (i) anchor to cellulose matrix via the carbohydrate-binding domain [CBM-3, FIG. 3]; and (ii) bind cellulose-degrading enzymes such as Endoglucanase D via enzyme-linked dockerin domains.

>gi|2506991|sp|Q06851|CIPA_CLOTM Cellulosomal scaffolding protein A precursor (Cellulosomal glycoprotein S1/SL) (Cellulose integrating protein A) (Cohesin) [*Clostridium thermocellum* ATCC 27405]. Bold residues are the linker sequence used in the above C114 construct.

(SEQ ID NO.: 5)

MRKVISMLLVVAMLTTIFAAMIPQTVSAATMTVEIGKVTAAVGSKVEIPI

TLKGVPSKGMANCDFVLGYDPNVLEVTEVKPGSIIKDPDPSKSFDSAIYP

DRKMIVFLFAEDSGRGTYAITQDGVFATIVATVKSAAAAPITLLEVGAFA

DNDLVEISTTFVAGGVNL*GSSVPTTQPNVPSDG*VVVEIGKVTGSVGTTVE

IPVYFRGVPSKGIANCDFVFRYDPNVLEIIGIDPGDIIVDPNPTKSFDTA

IYPDRKIIVFLFAEDSGTGAYAITKDGVFAKIRATVKSSAPGYITFDEVG

GFADNDLVEQKVSFIDGGVNV*GNATPTKGATPTNTATPTKSATATPTRPS*

*VPTNTPTNTPANTPVSGNLK*VEFYNSNPSDTTNSINPQFKVTNTGSSAID

LSKLTLRYYYTVDGQKDQTFWCDHAAIIGSNGSYNGITSNVKGTFVKMSS

STNNADTYLEI*SFTGGTLEPGAHVQIQGRFAKNDWSNYTQSNDYSFKSAS*

*QFVEWDQVTAYLNGVLVWGKEPGGSVVPSTQPVTTPPATTKPPATTKPPA*

TTIPPSDDPNAIKIKVDTVNAKPGDTVNIPVRFSGIPSKGIANCDFVYSY

DPNVLEIIEIKPGELIVDPNPDKSFDTAVYPDRKIIVFLFAEDSGTGAYA

ITKDGVFATIVAKVKSGAPNGLSVIKFVEVGGFANNDLVEQRTQFF*DGGV*

*NVGDTTVPTTPTTPVTTPTDDSNA*VRIKVDTVNAKPGDTVRIPVRFSGIP

SKGIANCDFVYSYDPNVLEIIEIEPGDIIVDPNPDKSFDTAVYPDRKIIV

FLFAEDSGTGAYAITKDGVFATIVAKVKSGAPNGLSVIKFVEVGGFANND

LVEQKTQFFDGGVNVG *DTTEPATPTTPVTT* *PTTTDDLDA*VRIKVDTVNAK

PGDTVRIPVRFSGIPSKGIANCDFVYSYDPNVLEIIEIEPGDIIVDPNPD

KSFDTAVYPDRKIIVFLFAEDSGTGAYAITKDGVFATIVAKVKSGAPNGL

SVIKFVEVGGFANNDLVEQKTQFFDGGVNV*GDTTEPATPTTPVTTPTTTD*

*DLDA*VRIKVDTVNAKPGDTVRIPVRFSGIPSKGIANCDFVYSYDPNVLEI

IEIEPGDIIVDPNPDKSFDTAVYPDRKIIVFLFAEDSGTGAYAITKDGVF

-continued

```
ATIVAKVKEGAPNGLSVIKFVEVGGFANNDLVEQKTQFFDGGVNVGDTTE

PATPTTPVTTPTTTDDLDAVRIKVDTVNAKPGDTVRIPVRFSGIPSKGIA

NCDFVYSYDPNVLEIIEIEPGELIVDPNPTKSFDTAVYPDRKMIVFLFAE

DSGTGAYAITEDGVFATIVAKVKSGAPNGLSVIKFVEVGGFANNDLVEQK

TQFFDGGVNVGDTTEPATPTTPVTTPTTTDDLDAVRIKVDTVNAKPGDTV

RIPVRFSGIPSKGIANCDFVYSYDPNVLEIIEIEPGDIIVDPNPDKSFDT

AVYPDRKIIVFLFAEDSGTGAYAITKDGVFATIVAKVKEGAPNGLSVIKF

VEVGGFANNDLVEQKTQFFDGGVNVGDTTVPTTSPTTTPPEPTITPNKLT

LKIGRAEGRPGDTVEIPVNLYGVPQKGIASGDFVVSYDPNVLEIIEIEPG

ELIVDPNPTKSFDTAVYPDRKMIVFLFAEDSGTGAYAITEDGVFATIVAK

VKEGAPEGFSAIEISEFGAFADNDLVEVETDLINGGVLVTNKPVIEGYKV

SGYILPDFSFDATVAPLVKAGFKVEIVGTELYAVTDANGYFEITGVPANA

SGYTLKISRATYLDRVIANVVVTGDTSVSTSQAPIMMWVGDIVKDNSINL

LDVAEVIRCFNATKGSANYVEELDINRNGAINMQDIMIVHKHFGATSSDY

DAQ
```

Figure 3A:
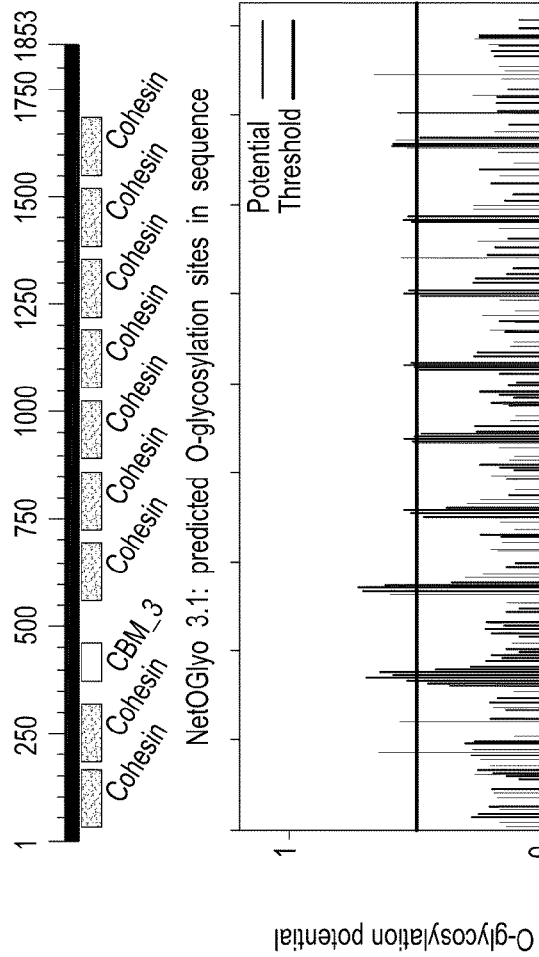
Figure 3B:
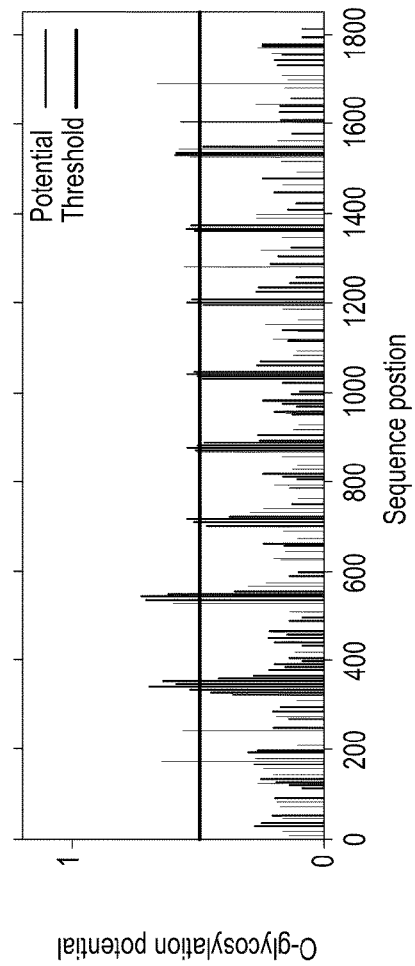
Figure 3C:
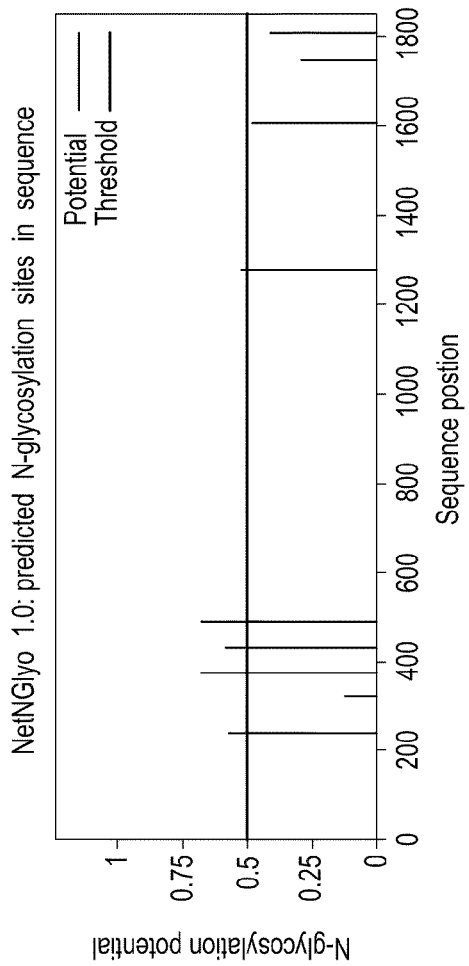

FIGS. 3A to 3C show the structural domain schema for cipA. FIG. 3A shows the structural domain schema are NetOGlyc 1.0 Server and NetNGlyc 1.0 Server analyses for cipA showing highly predicted O-linked (FIG. 3C) and N-linked glycosylation sites FIG. 3C. In particular, the O-linked sites are largely within the linker sequences.

Another example similar to cipA A is shown below. The linker sequence shown above in C560 [QTPTNTISVTPT-NNSTPTNTSTPKPNP] (SEQ ID NO.: 6) is derived from this sequence [shown below in bold italicized, except for an N to T substitution] and contains two potential N-linked glycosylation sites [underlined]. Other linker sequences used in constructs described below and/or in the HIV peptide disclosure are shown in bold.

>gi|50656899|gb|AAT79550.1| cellulosomal anchoring scaffoldin B precursor [*Bacteroides cellulosolvens*]

(SEQ ID NO.: 7)
```
MQSPRLKRKILSVILAVCYIISSFSIQFAATPQVNIIIGSAQGIPGSTVK

VPINLQNVPEIGINNCDFTIKFDSDILDFNSVEAGDIVPLPVASFSSNNS

KDIIKFLFSDATQGNMPINENGLFAVISFKIKDNAQKGISNIKVSSYGSF

SGMSGKEMQSLSPTFFSGSIDVSDVSTSKLDVKVGNVEGIAGTEVNVPIT

FENVPDNGINNCNFTLSYDSNALEFLITEAGNIIPLAIADYSSYRSMEGK

IKFLFSDSSQGTRSIKNDGVFANIKFKIKGNAIRDTYRIDLSELGSFSSK

QNNNLKSIATQFLSGSVNVKDIE SSVPTTSVHPTPTSVPPTPTKSSPGN

KMKIQIGDVKANQGDTVIVPITFNEVPVMGVNNCNFTLAYDKNIMEFISA

DAGDIVTLPMANYSYNMPSDGLVKFLYNDQAQGAMSIKEDGTFANVKFKI

KQSAAFGKYSVGIKAIGSISALSNSKLIPIESIFKDGSITVTNKPIVNIE

IGKVKVKAGDKIKVPVEIKDIPSIGINNCNFTLKYNSNVLKYVSNEAGTI

VPAPLANLSINKPDEGIIKLLFSDASQGGMPIKDNGIFVNLEFQAVNDAN

IGVYGLELDTIGAFSGISSAKMTSIEPQFNNGSIEIFNSAQTPVPSNTEV

QTPTNTISVTPTNNSPTNN STPKPNPLYNLNVNIGEISGEAGGVIEVPI

EFKNVPDFGINNCDFSVKYDKSIFEYVTYEAGSIVKDSIVNLACMENSGI

INLLFNDATQSSSPIKNNGVFAKLKFKINSNAASGTYQINAEGYGKFSGN

LNGKLTSINPIFENGIINIGNVTVK PTSTPADSSTITPTAITPTATPTIKG

TRTVTRIYWMNVLIGNMNAAIGEEVVVPIEFKNVPPFGINNCDFKLVYDS

NALELKKVEAGDIVPEPLANLSSNKSEGKIQFLFNDASQGSMQIENGGVF

AKITFKVKSTAASGIYNIRKDSVGSFSGLIDNKMTSIGPKFTDGSIVVGT

TPSAIVTTITPTATT IATPTIKGTPTATPMYWMNVVIGKM

NAEVGGEVVVPIEFNNVPSFGINNCDFKLVYDATALELKNVEAGDIIKTP

LANFSNNKSEEGKISFLFNDASQGSMQIENGGVFAKITFKVKSTTATGVY

DLRKDLVGSFSGLKDNKMTSIGAEFT

TPTVTPTATATPSVTIPTVTPTATATPSVTIPTVTPTATATPSAATPTVT

PTATATPSVTIPTVTPTVTATPSDTIPTVTPTATATPSAIVTTITPTATA

KPIATPTIKGTPTATPMYWMNVVIGKMNAEVGGEVVVPIEFKNVPSFGIN

NCDFKLVYDATALELKNVEAGDIIKTPLANFSNNKSEEGKISFLFNDASQ

GSMQIENGGVSAKITFKVKSTTAIGVYDIRKDLIGSFSGLKDSKMTSIGA

EFTNGSITVATTAPTVTPTATATESVTIPTVTPTATATECTATEGTATET

ATATPGAATPTETATESVMIPTVTRTATATETATATPTVKGTPTIKPVYK

MNVVIGRVNVVAGEEVVVPVEFKNIPAIGVNNCNFVLEYDANVLEVKKVD

ZGEIVPDALINFGSNNSDEGKVYFLFNDALQGRMQIANDGIFANITFKVK

SSAAAGIYNIRKDSVGAFSGLVDKLVPISAEFTDGSISVESAKSTPTATA

TGTNVTPTVAATVTPTATPASTTPTATPTATSTVKGTPTATPLYSMNVII

GKVNAEASGEVVVPVEFKDVPSIGINNCNFILEYDASALELDSAEAGEIV

PVPLGNFSSNNKDEGKIYFLFSDGTQGRMQIVNDGIFAKIKFKVKSTASD

GTYYIRKDSVGAFSGLIEKKIIKIGAEFTDGSITVRSLTPTPTVTPNVAS

PTPTKVVAEPTSNQPAGPGPITGTIPTATTTATATPTKASVATATPTATP

IVVVEPTIVRPGYNKDADLAVFISSDKSRYEESSIITYSIEYKNIGKVNA

TNVKIAAQIPKFTKVYDAAKGAVKGSEIVWMIGNLAVGESYTKEYKVKVD

SLTKSEEYTDNTVTISSDQTVDIPENITTGNDDKSTIRVMLYSNRFTPGS

HSSYILGYKDKTFKPKQNVTRAEVAAMFARIMGLTVKDGAKSSYKDVSNK

HWALKYIEAVTKSGIFKGYKDSTFHPNAPITRAELSTVIFNYLHLNNIAP

SKVHFTDINKHWAKNYIEEIYRFKLIQGYSDGSFKPNNNITRAEVVTMIN

RMLYRGPLKVKVGSFPDVSPKYWAYGDIEEASRNHKYTRDEKDGSEILIE
```

FIGS. 4A to 4C show the structural domain scheme for cellulosomal anchoring scaffoldin B precursor [*Bacteroides cellulosolvens*]. FIG. 4A shows the structural domain schema are NetOGlyc 1.0 Server and NetNGlyc 1.0 Server analyses for cipA showing highly predicted O-linked (FIG. 4B) and N-linked glycosylation sites (FIG. 4C). In particular, the O-linked sites are largely within the linker sequences.

The present invention includes compositions and methods for the use of inter-structural domain linker sequences derived from cellulose-degrading organisms for as preferred inter-domain linker sequences in protein engineering—particularly those with highly predicted glycosylation sites for use in engineering proteins produced in eukaryotic expression hosts. It has been found that among the improved properties obtained using these sequences are: i) inherent flexibility, thereby facilitating separation of linked domains which should greatly help correct folding of linked domains during synthesis and maintaining unobscured access by matching B cell receptors of antigen conformational epitopes; ii) glycosylation, thereby helping secretion and solubility of the product fusion protein, and shielding of the linker sequences from proteases.

Figure 5:
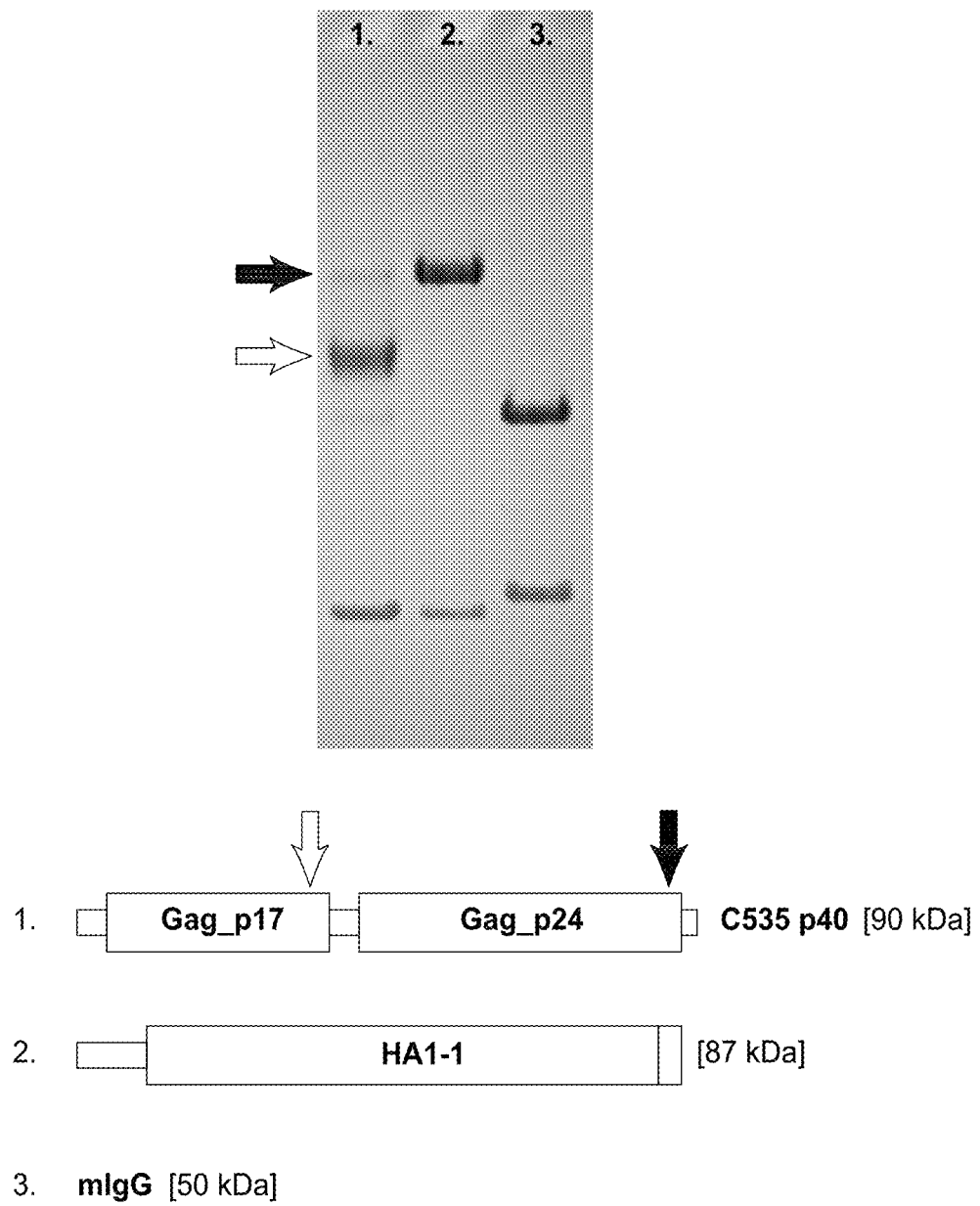

Removing proteolytic cleavage sites with the gag sequence. FIG. 5 lane 1 [below] shows the purified product of expression of [mAnti-DCIR_9E8_H-LV-hIgG4H-C-Viralgag-p40] C535 co-transfected with the appropriate L chain expression plasmid. The mature H chain sequence of C535 [gag residues are italicized and linking restriction site-encoded residues underlined] is:

(SEQ ID NO.: 8)
QVTLKESGPGILQPSQTLSLTCSFSGFSLSTSGMGLSWIRQPSGKGLEWL
AHIYWDDDKRYNPSLKSRLTISKDTSSNQVFLKITIVDTADAATYYCARS
SHYYGYGYGGYFDVWGAGTTVTVSSAKTKGPSVFPLAPCSRSTSESTAAL
GCLVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSL
GK<u>ASLE</u>*MGARASILSGGELDRWEKIRLRFGGKKKYKLKHIVWASRELERF*
*AVNFGLLETSEGCRQILGQLQFSLQTGSEELRSLYNTVATLYCVHQRIEI*
*KDTKEALDKIEEEQNKSKKKAQQAAADTGHSNQVSQNYFIVQNIQGQMVH*
*QAISFRTLNAWVKVVEEKAFSFEVIFMFSALSEGATFQDLNTMLNTVGGH*
*QAAMQMLKETINEEAAEWDRVHFVHAGFIAFGQMREFRGSDIAGTTSTLQ*
*EQIGWMTHNFFIFVGEIYKRWIILGLNKIVRMYSFTSILDIRQGFKEFFR*
*DYVDRFYKTLRAEQASQEVKNWMTETLLVQNANFDCKTILKALGFGATLE*
*EMMTACQGVG*

The upper arrow in FIG. 5 shows the approximate position expected for the C535-encoded H chain—only a small portion of the product has a band at this position. The bulk of the product, indicated by the lower arrow, is a shorter H chain of a size suggesting the existence of a protease-sensitive site roughly at the gag p17-p24 boundary.

Figure 6:
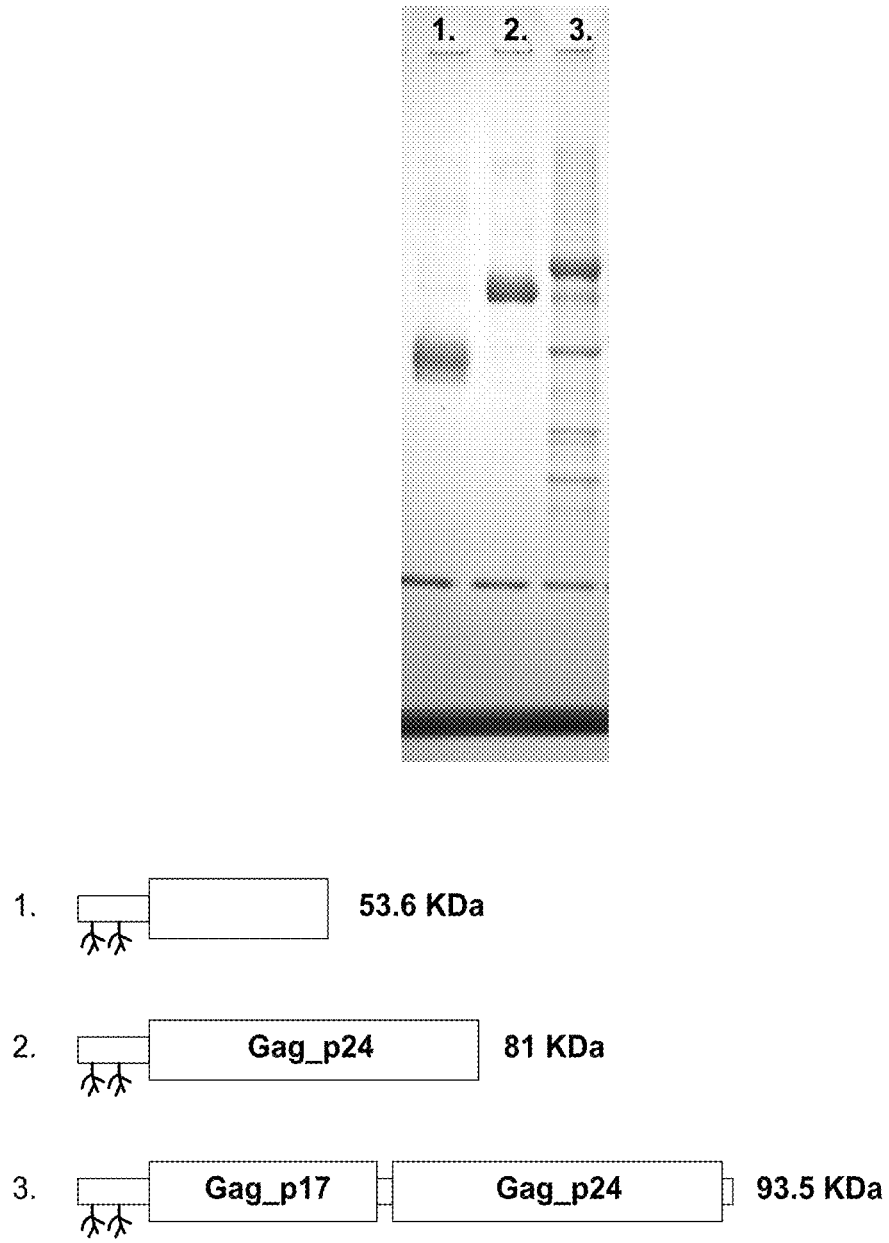

FIG. 6 lane 3 [below] shows the partially purified product of expression of [mAnti-DCIR_9E8_H-LV-hIgG4H-C-Flex-var1-Viralgag-p40-var1-6×His] C601 co-transfected with the appropriate L chain expression plasmid. The mature H chain sequence of C535 [gag residues are italicized, linking restriction site-encoded residues are underlined, and flexible linker residues are in bold] is:

(SEQ ID NO.: 9)
QVTLKESGPGILQPSQTLSLTCSFSGFSLSTSGMGLSWIRQPSGKGLEWL
AHIYWDDDKRYNPSLKSRLTISKDTSSNQVFLKITIVDTADAATYYCARS
SHYYGYGYGGYFDVWGAGTTVTVSSAKTKGPSVFPLAPCSRSTSESTAAL
GCLVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSL
GK<u>AS</u>QTPTNTISVTPTNNSTPTNNSNPKPNP<u>ASLE</u>*MGARASILSGGELDR*
*WEKIRLRRGGKKKYKLKHIVWASRELERFAVNRGLLETSEGCRQILGQLQ*
*PSLQTGSEELRSLYNTVATLYCVHQRIEIKDTKEALDKIEEEQNKS*<u>VDSE</u>
<u>FA</u>*QQAAADTGHSNQVSQNYPIVQNIQGQMVHQAISPRTLNAWVKVVEEKA*
*FSPEVIPMFSALSEGATPQDLNTMLNTVGGHQAAMQMLKETINEEAAEWD*
*RVHPVHAGPIAPGQMREPRGSDIAGTTSTLQEQIGWMTHNPPIPVGEIYK*
*RWIILGLNKIVRMYSPTSILDIRQGPKEPFRDYVDRFYKTLRAEQASQEV*
*KNWMTETLLVQNANPDCKTILKALGPGATLEEMMTACQGVG*HHHHHH

Figure 7:
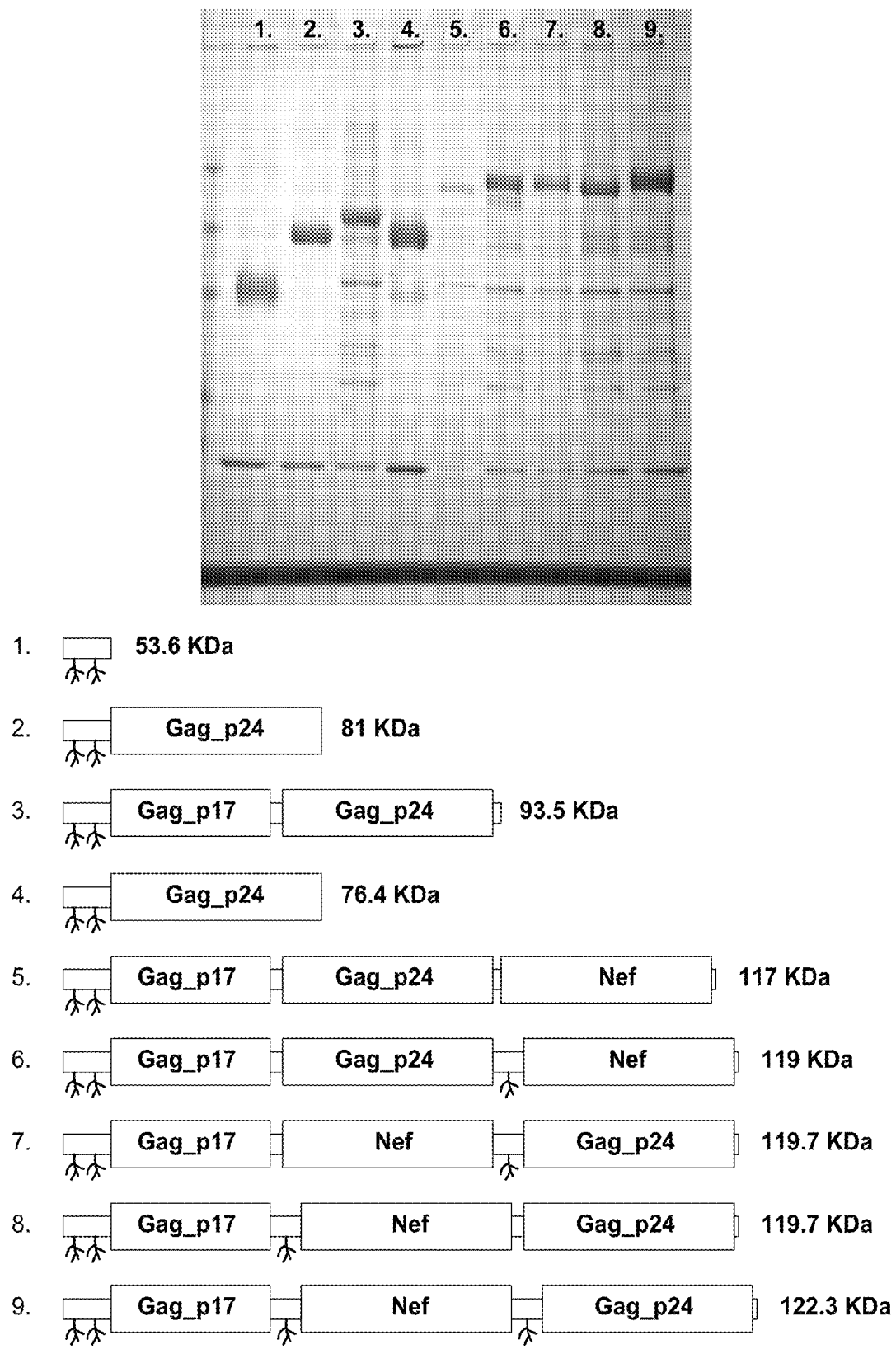

The above gag sequence has a KKK to VDESF sequence change [shown above underlined] removing a potential protease-sensitive site towards the C-terminus of gag p17 and FIG. 6 shows that this variant form is produced with a H chain that is largely undegraded [the lower molecular weight bands in lane 3 are 'background contaminants'—see FIG. 7].

In one specific embodiment, the present invention includes variants of gag p40 [p17+p24] with changes about the KKK sequence defined above that prevent proteolytic cleavage of secreted linked gag p17+p24 proteins.

Antibodies linked to preferred HIV nef antigen. The present invention includes, but is not limited to, one preferred vaccine targeting HIV antigens to dendritic cells would have a maximal amount of gag antigen linked with a maximal amount of nef antigen. FIG. 7 lane 4 [below] shows the partially purified product of expression of [mAnti-DCIR_9E8_H-LV-hIgG4H-C-Flex-v1-ViralNef] C757 cotransfected with the appropriate L chain expression plasmid. The mature H chain sequence of C757 [nef Consensus Clade B residues are italicized, linking restriction site-encoded residues are underlined, and flexible linker are in bold] is:

(SEQ ID NO.: 10)
QVTLKESGPGILQPSQTLSLTCSFSGFSLSTSGMGLSWIRQPSGKGLEWL
AHIYWDDDKRYNPSLKSRLTISKDTSSNQVFLKITIVDTADAATYYCARS
SHYYGYGYGGYFDVWGAGTTVTVSSAKTKGPSVFPLAPCSRSTSESTAAL
GCLVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSL
GK<u>AS</u>QTPTNTISVTPTNNSTPTNNSNPKPNP<u>AS</u>*MGGKWSKRSVVGWPTVR*
*ERMRRAEPAADGVGAVSRDLEKHGAITSSNTAANNADCAWLEAQEEEEVG*

```
FPVRPQVPLRPMTYKGALDLSHFLKEKGGLEGLIYSQKRQDILDLWVYHT

QGYFPDWQNYTPGPGIRYPLTFGWCFKLVPVEPEKVEEANEGENNSLLHP

MSLHGMDDPEREVLVWKFDSRLAFHHMARELHPEYYKDC
```

The antibody-antigen product analysis shown in FIG. 7 shows various H chain-antigen constructs transiently co-transfected into 293F cells with identical appropriate L chain expression constructs. Each lane represents product from a 5 ml transfection cell supernatant [3 days production] bound to excess Protein A beads, washed 2× with PBS+1M NaCl, the eluted with 20 mM HCl, dried, dissolved in reducing SDS PAGE sample buffer, and analyzed by reduced SDS PAGE with Coomassie Blue staining. This technique permits appraisal not only of the integrity of the expected H chain product, but allows estimation of relative production levels of the antibody-antigen products. The issue of relative production level is very important since vaccine production costs will depend heavily on the yield of intact secreted vaccine in large-scale mammalian cell fermentation systems. While expression levels can be greatly increased via alternate vectors systems—particularly carrying DNA elements favoring enhanced transcription when integrated into a mammalian cell genome and selection of high production transfected cell clones, these approaches are greatly aided by starting constructs that express intact secreted product in good yield without applying these additional approaches. The huge variation in production of secreted antibody-antigen fusions from transfected mammalian cells has been well documented in previous patent applications [cohesin-dockerin and DCIR] and these data show that the production level is largely independent of the antibody vehicle [variable and constant regions], but is rather an intrinsic property of the antigen itself. Thus FIG. 7 lane 4 shows very efficient production of [mAnti-DCIR_9E8_H-LV-hIgG4H-C-Flex-v1-ViralNef], showing that this configuration of antibody fused to nef Consensus Clade B antigen linked via QTPTNTISVTPTNNSTPTNNSNPKPNP is very favorable.

Antibodies linked to certain preferred HIV gag and nef antigens. [mAnti-DCIR_9E8_H-LV-hIgG4H-C-Flex-v1-Viralgag-p40-ViralNef] C758 has nef Consensus Clade B antigen appended directly proximal to the variant gag p40 antigen described above [joining residues are underlined and flexible linker sequence is in bold]:

(SEQ ID NO.: 11)

QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASQTPTNTISVTPTNNSTPTNNSNPKPNPASLEMGARASILSGGELDR

WEKIRLRPGGKKKYKLKHIVWASRELERFAVNPGLLETSEGCRQILGQLQ

PSLQTGSEELRSLYNTVATLYCVHQRIEIKDTKEALDKIEEEQNKSVDSE

-continued

FAQQAAADTGHSNQVSQNYPIVQNIQGQMVHQAISPRTLNAWVKVVEEKA

ESREVIPMFSALSEGATPQDLNTMLNTVGGHQAAMQMLKETINEEAAEWD

RVHPVHAGPIAPGQMREPRGSDIAGTTSTLQEQIGWMTHNPPIPVGEIYK

RWIILGLNKIVRMYSPTSILDIRQGPKEPFRDYVDRFYKTLRAEQASQEV

KNWMTETLLVQNANPDCKTILKALGPGATLEEMMTACQGVGGPASMGGKW

SKRSVVGWPTVRERMRRAEPAADGVGAVSRDLEKHGAITSSNTAANNADC

AWLEAQEEEEVGEPVRPQVPLRPMTYKGALDLSHFLKEKGGLEGLIYSQK

RQDILDLWVYHTQGYFPDWQNYTPGPGIRYPLTFGWCFKLVPVEPEKVEE

ANEGENNSLLHPMSLHGMDDPEREVLVWKFDSRLAFHHMARELHPEYYKD

C

FIG. 7 lane 5 shows that this expression plasmid directs the synthesis of this H chain-antigen fusion when cotransfected with the appropriate L chain is expressed very poorly as a secreted product. Lanes 6-9 show the secreted products from 293F cells co-transfected with L chain expression plasmid and H chain-gag expression constructs having nef Consensus Clade B antigen coding sequence insertions associated with proximal and/or distal flexible linker sequences. Addition of the flexible linker sequences facilitates secretion of intact antibody-gag/nef fusion vaccine. One preferred construct for production of the highest levels of vaccine is [mAnti-DCIR_9E8_H-LV-hIgG4H-C-Flex-v1-p17-f3-nef-f4-p24-6×His] C791 [see lane 9]. Since the relative levels of antibody-antigen fusions in such mammalian expression systems is largely independent of the antibody V-region, antibody-gag/nef antigen vaccines targeting different DC receptors should have similar advantage in production if [-Flex-v1-p17-f3-nef-f4-p24-6×His] is appended to their H chain C-terminus.

Lane 6H chain is [mAnti-DCIR_9E8_H-LV-hIgG4H-C-Flex-v1-Viralgag-p40-f4-nef] C767 [joining residues are underlined, flexible linker residues are in bold, and antigen residues are italicized]:

(SEQ ID NO.: 12)

QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GKASQTPTNTISVTPTNNSTPTNNSNPKPNPASLEMGARASILSGGELDR

WEKIRLRPGGKKKYKLKHIVWASRELERFAVNPGLLETSEGCRQILGQLQ

PSLQTGSEELRSLYNTVATLYCVHQRIEIKDTKEALDKIEEEQNKSVDSE

FAQQAAADTGHSNQVSQNYPIVQNIQGQMVHQAISPRTLNAWVKVVEEKA

ESREVIPMFSALSEGATPQDLNTMLNTVGGHQAAMQMLKETINEEAAEWD

RVHPVHAGPIAPGQMREPRGSDIAGTTSTLQEQIGWMTHNPPIPVGEIYK

RWIILGLNKIVRMYSPTSILDIRQGPKEPFRDYVDRFYKTLRAEQASQEV

KNWMTETLLVQNANPDCKTILKALGPGATLEEMMTACQGVGGPTNGSITV

AATAPTVTPTVNATPSAAGP<u>AS</u>MGGKWSKRSVVGWPTVRERMRRAEPAAD

GVGAVSRDLEKHGAITSSNTAANNADCAWLEAQEEEEVGEPVRPQVPLRP

MTYKGALDLSHFLKEKGGLEGLIYSQKRQDILDLWVYHTQGYFPDWQNYT

PGPGIRYPLTFGWCFKLVPVEPEKVEEANEGENNSLLHPMSLHGMDDPER

EVLVWKFDSRLAFHHMARELHPEYYKDC

Lane 7H chain is [mAnti-DCIR_9E8_H-LV-hIgG4H-C-Flex-v1-p17-nef-f4-p24-6×His] C790 C767 [joining residues are underlined, flexible linker residues are in bold, and antigen residues are italicized]:

(SEQ ID NO.: 13)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>QTPTNTISVTPTNNSTPTNNSNPKPNP<u>AS</u>LEMGARASILSGGELDR

WEKIRLRPGGKKKYKLKHIVWASRELERFAVNPGLLETSEGCRQILGQLQ

PSLQTGSEELRSLYNTVATLYCVHQRIEIKDTKEALDKIEEEQNKS<u>VD</u>MG

GKWSKRSVVGWPTVRERMRRAEPAADGVGAVSRDLEKHGAITSSNTAANN

ADCAWLEAQEEEEVGFPVRPQVPLRPMTYKGALDLSHFLKEKGGLEGLIY

SQKRQDILDLWVYHTQGYFPDWQNYTPGPGIRYPLTFGWCFKLVPVEPEK

VEEANEGENNSLLHPMSLHGMDDPEREVLVWKFDSRLAFHHMARELHPEY

YKDC<u>EF</u>TNGSITVAATAPTVTPTVNATPSAA<u>QF</u>AQQAAADTGHSNQVSQN

YPIVQNIQGQMVHQAISPRTLNAWVKVVEEKAFSPEVIPMFSALSEGATP

QDLNTMLNTVGGHQAAMQMLKETINEEAAEWDRVHPVHAGPIAPGQMREP

RGSDIAGTTSTLQEQIGWMTHNPPIPVGEIYKRWIILGLNKIVRMYSPTS

ILDIRQGPKEPFRDYVDRFYKTLRAEQASQEVKNWMTETLLVQNANPDCK

TILKALGPGATLEEMMTACQGVGHHHHHH

Lane 8H chain is [mAnti-DCIR_9E8_H-LV-hIgG4H-C-Flex-v1-p17-f3-nef-p24-6×His]C797 C767 [joining residues are underlined, flexible linker residues are in bold, and antigen residues are italicized]:

(SEQ ID NO.: 14)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>QTPTNTISVTPTNNSTPTNNSNPKPNP<u>AS</u>LEMGARASILSGGELDR

WEKIRLRPGGKKKYKLKHIVWASRELERFAVNPGLLETSEGCRQILGQLQ

PSLQTGSEELRSLYNTVATLYCVHQRIEIKDTKEALDKIEEEQNKS<u>VD</u>TV

TPTATATPSAIVTTITPTATTKP<u>VD</u>MGGKWSKRSVVGWPTVRERMRRAEP

AADGVGAVSRDLEKHGAITSSNTAANNADCAWLEAQEEEEVGFPVRPQVP

LRPMTYKGALDLSHFLKEKGGLEGLIYSQKRQDILDLWVYHTQGYFPDWQ

NYTPGPGIRYPLTFGWCFKLVPVEPEKVEEANEGENNSLLHPMSLHGMDD

PEREVLVWKFDSRLAFHHMARELHPEYYKDC<u>EF</u>AQQAAADTGHSNQVSQN

YPIVQNIQGQMVHQAISPRTLNAWVKVVEEKAESREVIPMFSALSEGATP

QDLNTMLNTVGGHQAAMQMLKETINEEAAEWDRVHPVHAGPIAPGQMREP

RGSDIAGTTSTLQEQIGWMTHNPPIPVGEIYKRWIILGLNKIVRMYSPTS

ILDIRQGPKEPFRDYVDRFYKTLRAEQASQEVKNWMTETLLVQNANPDCK

TILKALGPGATLEEMMTACQGVGHHHHHH

Lane 9H chain is [mAnti-DCIR_9E8_H-LV-hIgG4H-C-Flex-v1-p17-f3-nef-f4-p24-6×His] C791 C767 [joining residues are underlined, flexible linker residues are in bold, and antigen residues are italicized]:

(SEQ ID NO.: 15)
QVTLKESGPGILQPSQTLSLTCSFSGFSLSTSGMGLSWIRQPSGKGLEWL

AHIYWDDDKRYNPSLKSRLTISKDTSSNQVFLKITIVDTADAATYYCARS

SHYYGYGYGGYFDVWGAGTTVTVSSAKTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFEGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

GK<u>AS</u>QTPTNTISVTPTNNSTPTNNSNPKPNP<u>AS</u>LEMGARASILSGGELDR

WEKIRLRPGGKKKYKLKHIVWASRELERFAVNPGLLETSEGCRQILGQLQ

PSLQTGSEELRSLYNTVATLYCVHQRIEIKDTKEALDKIEEEQNKS<u>VD</u>TV

TPTATATPSAIVTTITPTATTKP<u>VD</u>MGGKWSKRSVVGWPTVRERMRRAEP

AADGVGAVSRDLEKHGAITSSNTAANNADCAWLEAQEEEEVGFPVRPQVP

LRPMTYKGALDLSHFLKEKGGLEGLIYSQKRQDILDLWVYHTQGYFPDWQ

NYTPGPGIRYPLTFGWCFKLVPVEPEKVEEANEGENNSLLHPMSLHGMDD

PEREVLVWKFDSRLAFHHMARELHPEYYKDC<u>EF</u>TNGSITVAATAPTVTPT

-continued

VNATPSAAQFAQQAAADTGHSNQVSQNYPIVQNIQGQMVHQAISPRTLNA
*WVKVVEEKAFSPEVIPMFSALSEGATPQDLNTMLNTVGGHQAAMQMLKET*
*INEEAAEWDRVHPVHAGPIAPGQMREPRGSDIAGTTSTLQEQIGWMTHNP*
*PIPVGEIYKRWIILGLNKIVRMYSPTSILDIRQGPKEPERDYVDREYKTL*
*RAEQASQEVKNWMTETLLVQNANPDCKTILKALGPGATLEEMMTACQGVG*
HHHHHH

A further modification being tested to remove residual degradation detected under severe fermentation conditions in CHO-S cell production of the above protein is shown below with a KKK to NKQ change shown highlighted in underlined, bold, italics:

(SEQ ID NO.: 16)
QVTLKESGPGILQPSQTLSLTCSFSGFSLSTSGMGLSWIRQPSGKGLEWL
AHIYWDDDKRYNPSLKSRLTISKDTSSNQVFLKITIVDTADAATYYCARS
SHYYGYGYGGYFDVWGAGTTVTVSSAKTKGPSVFPLAPCSRSTSESTAAL
GCLVKDYFPEPVTVSWNSGALTSGVHTFPAVLQSSGLYSLSSVVTVPSSS
LGTKTYTCNVDHKPSNTKVDKRVESKYGPPCPPCPAPEFEGGPSVFLFPP
KPKDTLMISRTPEVTCVVVDVSQEDPEVQFNWYVDGVEVHNAKTKPREEQ
FNSTYRVVSVLTVLHQDWLNGKEYKCKVSNKGLPSSIEKTISKAKGQPRE
PQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSL
GKASQTPTNTISVTPTNNSTPTNNSNPKPNPASLEMGARASILSGGELDR
*WEKIRLRPGG* *NK* QYKLKHIVWASRELERFAVNPGLLETSEG-CRQILGQLQ
*PSLQTGSEELRSLYNTVATLYCVHQRIEIKDTKEALDKIEEEQNKS*VDTV
TPTATATPSAIVTTITPTATTKPVD*MGGKWSKRSVVGWPTVRERMRRAEP*
*AADGVGAVSRDLEKHGAITSSNTAANNADCAWLEAQEEEVGFPVRPQVP*
*LRPMTYKGALDLSHFLKEKGGLEGLIYSQKRQDILDLWVYHTQGYFPDWQ*
*NYTPGPGIRYPLTFGWCFKLVPVEPEKVEEANEGENNSLLHPMSLHGMDD*
*PEREVLVWKFDSRLAFHHMARELHPEYYKDC*EFTNGSITVAATAPTVTPT
VNATPSAAQFAQQAAADTGHSNQVSQNYPIVQNIQGQMVHQAISPRTLNA
*WVKVVEEKAFSPEVIPMFSALSEGATPQDLNTMLNTVGGHQAAMQMLKET*
*INEEAAEWDRVHPVHAGPIAPGQMREPRGSDIAGTTSTLQEQIGWMTHNP*
*PIPVGEIYKRWIILGLNKIVRMYSPTSILDIRQGPKEPERDYVDREYKTL*
*RAEQASQEVKNWMTETLLVQNANPDCKTILKALGPGATLEEMMTACQGVG*
HHHHHH

Certain gag-nef antigen fusions with maximal antigen epitopes were found to have efficient secretion/production properties. Variants of gag p40 with inserts or appendages of nef antigen flanked by preferred flexible linker sequences were found to be particularly well produced and secreted. It was found that the flexible linker sequences disclosed herein and obtainable from cellulose degrading organisms were able to facilitate the secretion of intact antigens and/or linked antigens as antibody-antigen fusion proteins.

DNA sequences of antigen coding sequence:C757 antigen region is [bold sequences are joining sites or a stop codon]:

(SEQ ID NO.: 17)

GCTAGCATGGGAGGCAAATGGAGTAAAAGAAGTGTTGTGGGTTGGCCAAC

TGTGAGAGAAAGAATGAGAAGGGCTGAACCAGCCGCTGATGGTGTAGGTG

CTGTGTCACGAGATCTGGAAAAACACGGAGCAATAACATCCTCTAATACC

GCCGCAAATAACGCAGACTGTGCCTGGCTCGAAGCTCAAGAAGAAGAAGA

AGTCGGATTCCCCGTGCGACCCCAAGTTCCCCTCAGACCAATGACTTATA

AAGGCGCTCTGGATCTTAGCCACTTTCTTAAAGAAAAAGGAGGACTGGAA

GGACTTATTTATTCACAAAAAAGACAAGACATCCTCGATTTGTGGGTATA

TCATACTCAAGGTTATTTCCCAGACTGGCAAAATTATACTCCTGGACCCG

GCATTCGATATCCCCTTACCTTTGGATGGTGCTTTAAACTTGTCCCCGTC

GAACCTGAAAAAGTAGAAGAAGCAAATGAAGGCGAAAATAATTCACTGCT

CCACCCTATGTCACTGCACGGAATGGATGACCCCGAACGCGAAGTTCTGG

TATGGAAATTTGATTCAAGACTTGCTTTTCACCACATGGCTAGAGAACTT

CACCCCGAATATTATAAAGACTGTTGA

C791 linker and antigen coding sequence is [bold sequences are joining sites or a stop codon]:

(SEQ ID NO.: 18)

GCTAGTCAGACCCCCACCAACACCATCAGCGTGACCCCCACCAACAACAG

CACCCCCACCAACAACAGCAACCCCAAGCCCAACCCCGCTAGCCTCGAGA

TGGGTGCGAGAGCGTCAATATTAAGCGGTGGCGAATTAGATAGATGGGAA

AAAATTCGGTTAAGGCCAGGGGGAAAGAAAAAATATAAATTAAAACATAT

AGTATGGGCAAGCAGGGAGCTAGAACGATTCGCAGTTAATCCTGGCCTGT

TAGAAACATCAGAAGGCTGTAGACAAATACTGGGACAGCTACAACCATCC

CTTCAGACAGGATCAGAAGAACTTAGATCATTATATAATACAGTAGCAAC

CCTCTATTGTGTGCATCAAAGGATAGAGATAAAAGACACCAAGGAAGCTT

TAGACAAGATAGAGGAAGAGCAAAACAAAAGTGTCGATACCGTGACCCCC

ACCGCCACCGCCACCCCCAGCGCCATCGTGACCACCATCACCCCCACCGC

CACCACCAAGCCCGTCGACATGGGAGGCAAATGGAGTAAAAGAAGTGTTG

TGGGTTGGCCAACTGTGAGAGAAAGAATGAGAAGGGCTGAACCAGCCGCT

GATGGTGTAGGTGCTGTGTCACGAGATCTGGAAAAACACGGAGCAATAAC

ATCCTCTAATACCGCCGCAAATAACGCAGACTGTGCCTGGCTCGAAGCTC

AAGAAGAAGAAGAAGTCGGATTCCCCGTGCGACCCCAAGTTCCCCTCAGA

CCAATGACTTATAAAGGCGCTCTGGATCTTAGCCACTTTCTTAAAGAAAA

AGGAGGACTGGAAGGACTTATTTATTCACAAAAAAGACAAGACATCCTCG

ATTTGTGGGTATATCATACTCAAGGTTATTTCCCAGACTGGCAAAATTAT

ACTCCTGGACCCGGCATTCGATATCCCCTTACCTTTGGATGGTGCTTTAA

ACTTGTCCCCGTCGAACCTGAAAAAGTAGAAGAAGCAAATGAAGGCGAAA

ATAATTCACTGCTCCACCCTATGTCACTGCACGGAATGGATGACCCCGAA

CGCGAAGTTCTGGTATGGAAATTTGATTCAAGACTTGCTTTTCACCACAT

```
GGCTAGAGAACTTCACCCCGAATATTATAAAGACTGTGAATTCACCAACG

GCAGCATCACCGTGGCCGCCACCGCCCCCACCGTGACCCCCACCGTGAAC

GCCACCCCCAGCGCCGCCCAATTCGCACAGCAAGCAGCAGCTGACACAGG

ACACAGCAATCAGGTCAGCCAAAATTACCCTATAGTGCAGAACATCCAGG

GGCAAATGGTACATCAGGCCATATCACCTAGAACTTTAAATGCATGGGTA

AAAGTAGTAGAAGAGAAGGCTTTCAGCCCAGAAGTGATACCCATGTTTTC

AGCATTATCAGAAGGAGCCACCCCACAAGATTTAAACACCATGCTAAACA

CAGTGGGGGACATCAAGCAGCCATGCAAATGTTAAAAGAGACCATCAAT

GAGGAAGCTGCAGAATGGGATAGAGTGCATCCAGTGCATGCAGGGCCTAT

TGCACCAGGCCAGATGAGAGAACCAAGGGGAAGTGACATAGCAGGAACTA

CTAGTACCCTTCAGGAACAAATAGGATGGATGACACATAATCCACCTATC

CCAGTAGGAGAAATCTATAAAAGGTGGATAATCCTGGGATTAAATAAAAT

AGTAAGAATGTATAGCCCTACCAGCATTCTGGACATAAGACAAGGACCAA

AGGAACCCTTTAGAGACTATGTAGACCGATTCTATAAAACTCTAAGAGCC

GAGCAAGCTTCACAAGAGGTAAAAAATTGGATGACAGAAACCTTGTTGGT

CCAAAATGCGAACCCAGATTGTAAGACTATTTTAAAAGCATTGGGACCAG

GAGCGACACTAGAAGAAATGATGACAGCATGTCAGGGAGTGGGGCATCAC

CATCACCATCACTGA
```

Figure 8:
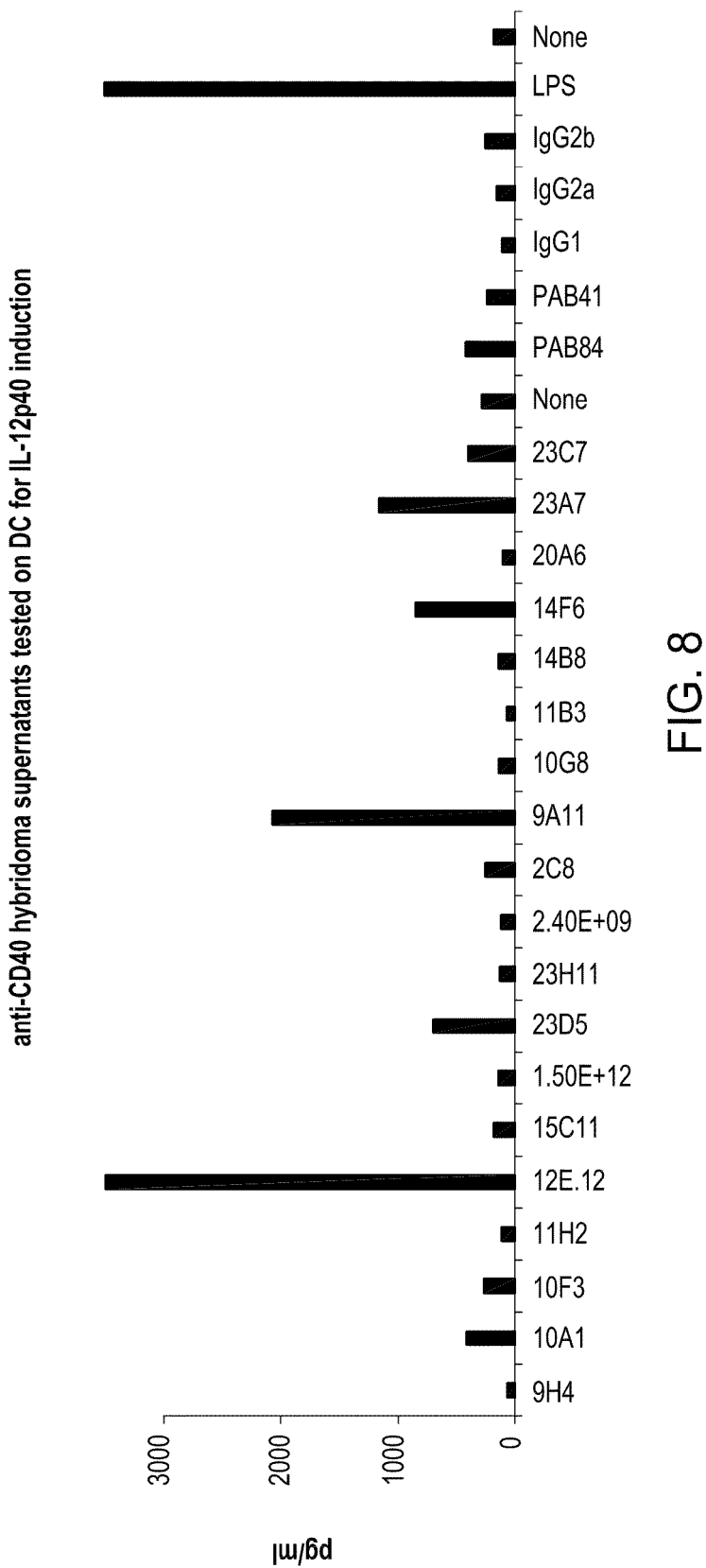

The following examples show that the present invention was able to target the HIV and other antigens to human DC via CD40. Generation of potent activating anti-CD40 monoclonal antibodies. Mice were immunized with a mouse IgG2b-human CD40 fusion protein and B cells from lymph nodes draining the injection site were subsequently immortalized as hybridomas. Supernatants from 35 hybridomas secreting anti-CD40 reactive antibodies as detected by FACS versus 293F cells transfected with CD40 cDNA were tested in overnight cultures of human dendritic cells for induction of cytokine secretion. FIG. 8 shows an example of this type of screen designed to detect the subset of anti-CD40 antibodies that can bind and activate CD40. This data set shows that two hybridomas 12E12 and 9A11 were especially potent in directing DC to secreted IL-12p40. cDNAs encoding the 12E12 heavy and light chains were derived using standard cloning and sequencing technologies and the variable regions were engineered into vectors expressing mouse 12E12 variable regions grafted onto human IgG4 constant regions.

C269   rAB-pIRES2[manti-CD40__12E12.3F3_K-V-hIgGK-C] The DNA sequence below shows the chimeric light chain coding region and the amino acid sequence the expected secreted mature light chain with the mouse variable region italicized.

```
                                        (SEQ ID NO.: 19)
ATGATGTCCTCTGCTCAGTTCCTTGGTCTCCTGTTGCTCTGTTTTCAAGG

TACCAGATGTGATATCCAGATGACACAGACTACATCCTCCCTGTCTGCCT

CTCTAGGAGACAGAGTCACCATCAGTTGCAGTGCAAGTCAGGGCATTAGC

AATTATTTAAACTGGTATCAGCAGAAACCAGATGGAACTGTTAAACTCCT

GATCTATTACACATCAATTTTACACTCAGGAGTCCCATCAAGGTTCAGTG

GCAGTGGGTCTGGGACAGATTATTCTCTCACCATCGGCAACCTGGAACCT

GAAGATATTGCCACTTACTATTGTCAGCAGTTTAATAAGCTTCCTCCGAC

GTTCGGTGGAGGCACCAAACTCGAGATCAAACGAACTGTGGCTGCACCAT

CTGTCTTCATCTTCCCGCCATCTGATGAGCAGTTGAAATCTGGAACTGCC

TCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCA

CAGAGCAGGACAGCAAGGACAGCACCTACAGCCTCAGCAGCACCCTGACG

CTGAGCAAAGCAGACTACGAGAAACACAAAGTCTATGCCTGCGAAGTCAC

CCATCAGGGCCTGAGCTCGCCCGTCACAAAGAGCTTCAACAGGGGAGAGT

GTTAG*DIQMTQTTSSLSASLGDRVTISCSASQGISNYLNWYQQKPDGTVK

LLIYYTSILHSGVPSRFSGSGSGTDYSLTIGNLEPEDIATYYCQQFNKLP

PTFGGGTKLEIK*RTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
```

C230   rAB-pIRES2[manti-CD40__12E12.3F3_H-V-hIgG4H-C] The DNA sequence below shows the chimeric heavy chain coding region and the amino acid sequence the expected secreted mature light chain with the mouse variable region italicized.

```
                                        (SEQ ID NO.: 20)
ATGAACTTGGGGCTCAGCTTGATTTTCCTTGTCCTTGTTTTAAAAGGTGT

CCAGTGTGAAGTGAAGCTGGTGGAGTCTGGGGGAGGCTTAGTGCAGCCTG

GAGGGTCCCTGAAACTCTCCTGTGCAACCTCTGGATTCACTTTCAGTGAC

TATTACATGTATTGGGTTCGCCAGACTCCAGAGAAGAGGCTGGAGTGGGT

CGCATACATTAATTCTGGTGGTGGTAGCACCTATTATCCAGACACTGTAA

AGGGCCGATTCACCATCTCCAGAGACAATGCCAAGAACACCCTGTACCTG

CAAATGAGCCGGCTGAAGTCTGAGGACACAGCCATGTATTACTGTGCAAG

ACGGGGGTTACCGTTCCATGCTATGGACTATTGGGGTCAAGGAACCCTCAG

TCACCGTCTCCTCAGCCAAAACGAAGGGCCCATCCGTCTTCCCCCTGGCG

CCCTGCTCCAGGAGCACCTCCGAGAGCACAGCCGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACGAA

GACCTACACCTGCAACGTAGATCACAAGCCCAGCAACACCAAGGTGGACA

AGAGAGTTGAGTCCAAATATGGTCCCCCATGCCCACCCTGCCCAGCACCT

GAGTTCGAAGGGGGACCATCAGTCTTCCTGTTCCCCCCAAAACCCAAGGA

CACTCTCATGATCTCCCGGACCCCTGAGGTCACGTGCGTGGTGGTGGACG

TGAGCCAGGAAGACCCCGAGGTCCAGTTCAACTGGTACGTGGATGGCGTG

GAGGTGCATAATGCCAAGACAAAGCCGCGGGAGGAGCAGTTCAACAGCAC

GTACCGTGTGGTCAGCGTCCTCACCGTCCTGCACCAGGACTGGCTGAACG

GCAAGGAGTACAAGTGCAAGGTCTCCAACAAAGGCCTCCCGTCCTCCATC

GAGAAAACCATCTCCAAAGCCAAAGGGCAGCCCCGAGAGCCACAGGTGTA
```

-continued
```
CACCCTGCCCCCATCCCAGGAGGAGATGACCAAGAACCAGGTCAGCCTGA

CCTGCCTGGTCAAAGGCTTCTACCCCAGCGACATCGCCGTGGAGTGGGAG

AGCAATGGGCAGCCGGAGAACAACTACAAGACCACGCCTCCCGTGCTGGA

CTCCGACGGCTCCTTCTTCCTCTACAGCAGGCTAACCGTGGACAAGAGCA

GGTGGCAGGAGGGGAATGTCTTCTCATGCTCCGTGATGCATGAGGCTCTG

CACAACCACTACACACAGAAGAGCCTCTCCCTGTCTCTGGGTAAAGCTAG

CTGAEVKLVESGGGLVQPGGSLKLSCATSGFTFSDYYMYWVRQTPEKRLE

WVAYINSGGGSTYYPDTVKGRFTISRDNAKNTLYLQMSRLKSEDTAMYYC

ARRGLPFHAMDYWGQGTSVTVSSAKTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPPCPAPEFEGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

AS
```

Variants of C230 were engineered to encode CD4012E12H chains with antigens fused to the human IgG4 C-terminus e.g., C291 rAB-pIRES2[manti-CD40_12E12.3F3_H-V-hIgG4H-C-Flex-FluHA1-1-6×His] encodes an H chain with the sequence shown below with the Influenza HA1-1 antigen region shown italicized and a flexible linker sequence and C-terminal poly-histidine tag shown in bold:

(SEQ ID NO.: 21)

EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKASDT

TEPATPTTPVTT*DTICIGYHANNSTDTVDTVLEKNVTVTHSVNLLEDSHN*

*GKLCRLKGIAPLQLGKCNIAGWLLGNPECDPLLPVRSWSYIVETPNSENG*

*ICYPGDFIDYEELREQLSSVSSFERFEIFPKESSWPNHNTNGVTAACSHE*

*GKSSFYRNLLWLTEKEGSYPKLKNSYVNKKGKEVLVLWGIHHPPNSKEQQ*

*NLYQNENAYVSVVTSNYNRRFTPEIAERPKVRDQAGRMNYYWTLLKPGDT*

*IIFEANGNLIAPMYAFALSRGEGSGIITSNASMHECNTKCQTPLGAINSS*

*LPYQNIHPVTIGECLKYVRSAKLRMV*HHHHHH

Another type of variant H chain construct is C450 rAB-pIRES2[manti-CD40_12E12.3F3_H-LV-hIgG4H-C-Dockerin-var1] encodes an H chain with the sequence shown below with a C-terminal Dockerin domain antigen region shown italicized:

(SEQ ID NO.: 22)

EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGKAS*NS*

*PQNEVLYGDVNDDGKVNSTDLTLLKRYVLKAVSTLPSSKAEKNADVNRDG*

*RVDSSDVTILSRYLIRVIEKLPI*

Thus, expression vectors encoding the above and similar variant H chains can be co-transfected into 293F or CHO-S cells resulting in the secretion of anti-CD4012E12-hIgG4 antibody fusion proteins, which can be readily purified by protein A affinity chromatography.

Such antibody-antigen proteins can be used as vaccines to deliver antigen with high efficiency to human dendritic cells in vitro or in vivo. The anti-CD4012E12-hIgG4 Dockerin protein can be used likewise to deliver cohesin-antigen fusion proteins. For example: C32 *Ecoli*-pET28[Cohesin-FluM1-6×His] encodes the sequence shown below where the Influenza M1 protein is shown italicized:

(SEQ ID NO.: 23)

MDLDAVRIKVDTVNAKPGDTVNIPVRFSGIPSKGIANCDFVYSYDPNVLE

IIEIKPGELIVDPNPTKSFDTAVYPDRKMIVFLFAEDSGTGAYAITKDGV

FATIVAKVKEGAPNGLSVIKFVEVGGFANNDLVEQKTQFFDGGVNVGDTT

EPATPTTPVTTPTTTDDLDAA*SLLTEVETYVLSIIPSGPLKAEIAQRLED*

*VFAGKNTDLEVLMEWLKTRPILSPLTKGILGFVFTLTVPSERGLQRRRFV*

*QNALNGNGDPNNMDKAVKLYRKLKREITFHGAKEIALSYSAGALASCMGL*

*IYNRMGAVTTEVAFGLVCATCEQIADSQHRSHRQMVTTTNPLIRHENRMV*

*LASTTAKAMEQMAGSSEQAAEAMDIASQARQMVQAMRTIGTHPSSSAGLK*

*DDLLENLQAYQKRMGVQMQREKLE*HHHHHH

The above protein can be expressed as a soluble protein in *E. coli* and prepared as a pure product by ion exchange and metal affinity chromatographies. Highly stable complexes or conjugates between anti-CD4012E12-hIgG4 Dockerin fusion protein and Cohesin Flu M1 fusion protein can be assembled via the high affinity Dockerin-Cohesin interaction.

A dose range of such anti-CD4012E12-hIgG4 Dockerin-Cohesin Flu M1 conjugates were incubated with human dendritic cells for one day, then syngeneic CD8+ T cells were added and incubation was continued for several more days. Cells were then stained with anti-CD8 antibody and a HLA-A2 tetramer reagent specific for T cells bearing TCR corresponding to the immunodominant Flu M1 epitope 58-66. Tetramer positive cells are shown in the boxed gate. This data shows that concentrations of anti-CD4012E12-hIgG4 Dockerin Cohesin Flu M1 conjugates as low as 0.001 ug/ml elicit the proliferation of Flu M1-specific CD8+ T cells at levels significantly higher than either no conjugate added or [next figure panel] than a parallel dose range series of control IgG4 Dockerin Cohesin Flu M1 conjugates. These data demonstrate that anti-CD4012E12 antibody is remarkably proficient at delivering antigen to DC resulting in processing and presentation of the antigen as seen by the proliferation of antigen specific T cells.

Figure 9:
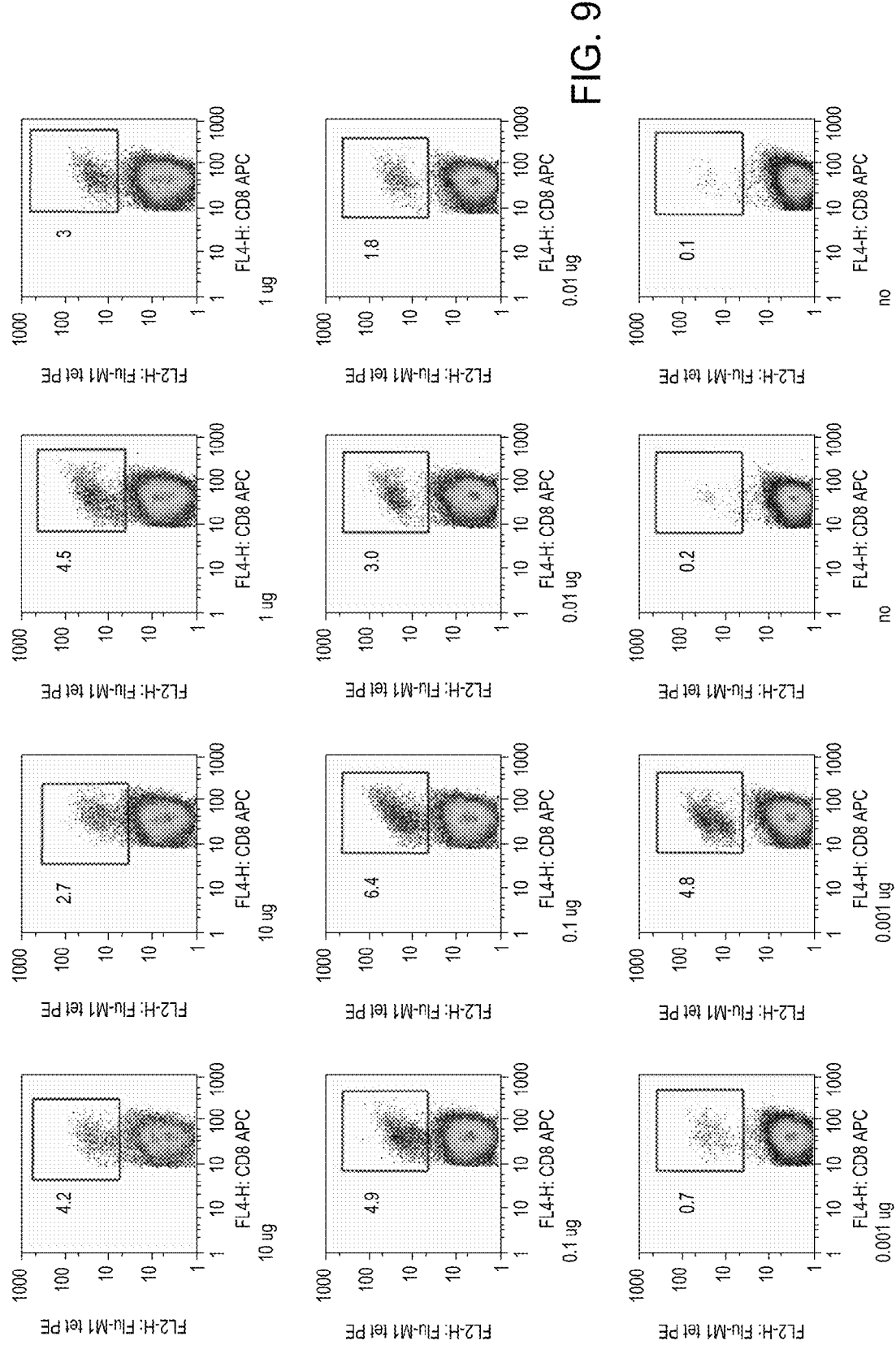

FIG. 9 shows FACS analysis of CD8+ staining [horizontal axis] versus Flu M1-tetramer staining [vertical axis] as elicited by a dose range from 10 ug/ml to no anti-CD4012E12-hIgG4 Dockerin-Cohesin Flu M1 conjugate.

Figure 10:
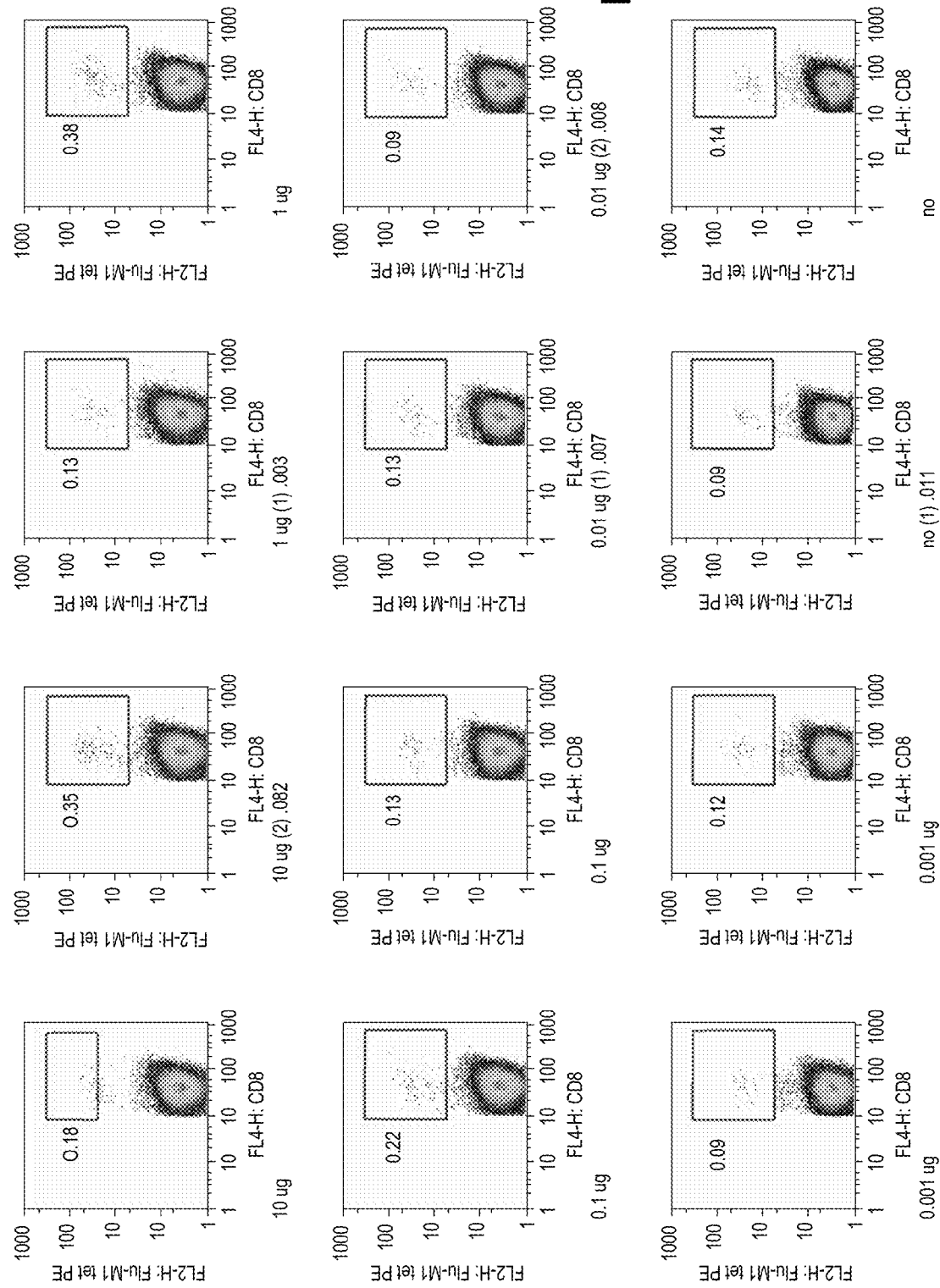
FIG. 10 shows FACS analysis of CD8+ staining [horizontal axis] versus Flu M1-tetramer staining [vertical axis] as elicited by a dose range from 10 ug/ml to no control hIgG4 Dockerin-Cohesin Flu M1 conjugate.

FIG. 10 shows FACS analysis of CD8+ staining [horizontal axis] versus Flu M1-tetramer staining [vertical axis] as elicited by a dose range from 10 ug/ml to no control hIgG4 Dockerin-Cohesin Flu M1 conjugate.

Alignment of C269 (seqA) anti-CD4012E12 light chain sequence with variants engineered to retain CD40 binding and to enhance similarity with human light chain variable sequences—and by including preferred codons to enhance expression of secreted product.

```
seqA  DIQMTQTTSSLSASLGDRVTISCSASQGISNYLNWYQQKPDGTVKLLIYYTSILHSGVPS
seqB  DIQMTQTTSSLSASLGDRVTISCSASQGISNYLNWYQQKPDGTVKLLIHYTSILHSGVPS
seqC  DIQMTQTTSSLSASLGDRVTISCSASQGISNYLNWYQQKPDGTVKLLIHYTSILHSGVPS
seqD  DIQMTQTTSSLSASLGDRVTISCSASQGISNYLNWYQQKPDGTVKLLIHYTSILHSGVPS
seqE  DIQMTQTTSSLSTSLGDRVTISCSASQGISNYLNWYQQKPDGTVKLLIHYTSILHSGVPS
      ********.:********************************.******** seqA  RFSGSGSGTDYSLTIGNLEPEDIATYYCQQFNKLPPTFGGGTKLEIKRTVAAPSVFIFPP
seqB  RFSGSGSGTDYSLTISNLEQEDIATYFCQQFNKLPPTFGGGTKLEIKRTVAAPSVFIFPP
seqC  RFSGS-SGTDYSLTISNLEQEDIATYFCQQFNKLFFTFGGGTKLEIKRTVAAFSVFIFFF
seqD  RFSGSGSGTDYSLTISNLEQEDIATYFCQQFNKPPPTFGGGTKLEIKRTVAAPSVFIFPP
seqE  RFSGSGSGTDYSLTISNLEQEDIATYFCQQFNKLPPTFGGGTKLEIKRTVAAPSVFIFPP
      *** *****.* ****:** *********************** seqA  SDEQLKSGTASVVCLLNNFYPREAKVQWKVDNALQSGNSQESVTEQDSKDSTYSLSSTLT
seqB  SDEQLKSGTASVVCLLNNFYPREAKVQWKVDNALQSGNSQESVTEQDSKDSTYSLSSTLT
seqC  SDEQLKSGTASVVCLLNNFYPREAKVQWKVDNALQSGNSQESVTEQDSKDSTYSLSSTLT
seqD  SDEQLKSGTASVVCLLNNFYPREAKVQWKVDNALQSGNSQESVTEQDSKDSTYSLSSTLT
seqE  SDEQLKSGTASVVCLLNNFYPREAKVQWKVDNALQSGNSQESVTEQDSKDSTYSLSSTLT
      ************************************************************ seqA  LSKADYEKHKVYACEVTHQGLSSPVTKSFNRGEC
seqB  LSKADYEKHKVYACEVTHQGLSSPVTKSFNRGEC
seqC  LSKADYEKHKVYACEVTHQGLSSPVTKSFNRGEC
seqD  LSKADYEKHKVYACEVTHQGLSSPVTKSFNRGEC
seqE  LSKADYEKHKVYACEVTHQGLSSPVTKSFNRGEC
      **********************************

(SEQ ID NO.: 24, 25, 26, 27, 28, respectively)
```

Alignment of C268 (seqA) anti-CD4012E12 heavy chain sequence with a variant engineered to retain CD40 binding and to enhance similarity with human light chain variable sequences—and by including preferred codons to enhance expression of secreted product.

```
seqA  EVKLVESGGGLVQPGGSLKLSCATSGFTFSDYYMYWVRQTPEKRLEWVAYTNSGGGSTYY
seqB  EVNLVESGGGLVQPGGSLKVSCVTSGFTFSDYYMYWVRQTPEKRLEWVAYTNSGGGSTYY
      .***********:.************************************** seqA  PDTVKGRFTISRDNAKNTLYLQMSRLKSEDTAMYYCARRGLPFHAMDYWGQGTSVTVSSA
seqB  PDTVKGRFTISRDNAKNSLYLQMSRLKSEDTAMYYCARRGLPFHAMDYWGQGTLVTVSVA
      ***************:****************************** ** * seqA  KTKGPSVFPLAPCSRSTSESTAALGCLVKDYFPEPVTVSWNSGALTSGVHTFPAVLQSSG
seqB  STKGPSVFPLAPCSRSTSESTAALGCLVKDYFPEPVTVSWNSGALTSGVHTFPAVLQSSG
      .*********************************************************** seqA  LYSLSSVVTVPSSSLGTKTYTCNVDHKPSNTKVDKRVESKYGPPCPPCPAPEFEGGPSVF
seqB  LYSLSSVVTVPSSSLGTKTYTCNVDHKPSNTKVDKRVESKYGPPCPPCPAPEFEGGPSVF
      ************************************************************ seqA  LFPPKPKDTLMISRTPEVTCVVVDVSQEDPEVQFNWYVDGVEVHNAKTKPREEQFNSTYR
seqB  LFPPKPKDTLMISRTPEVTCVVVDVSQEDPEVQFNWYVDGVEVHNAKTKPREEQFNSTYR
      ************************************************************ seqA  VVSVLTVLHQDWLNGKEYKCKVSNKGLPSSTEKTISKAKGQPREPQVYTLPPSQEEMTKN
seqB  VVSVLTVLHQDWLNGKEYKCKVSNKGLPSSTEKTISKAKGQPREPQVYTLPPSQEEMTKN
      ************************************************************
```

```
seqA  QVSLTCLVKGFYPSDIAVEWESNGQPENNYKTTPPVLDSDGSFFLYSRLTVDKSRWQEGN
seqB  QVSLTCLVKGFYPSDIAVEWESNGQPENNYKTTPPVLDSDGSFFLYSRLTVDKSRWQEGN
      ************************************************************ seqA  VFSCSVMHEALHNHYTQKSLSLSLGKAS
seqB  VFSCSVMHEALHNHYTQKSLSLSLGKAS
      ***************************
```

(SEQ ID NO.: 29, 30, respectively)

Figure 11:
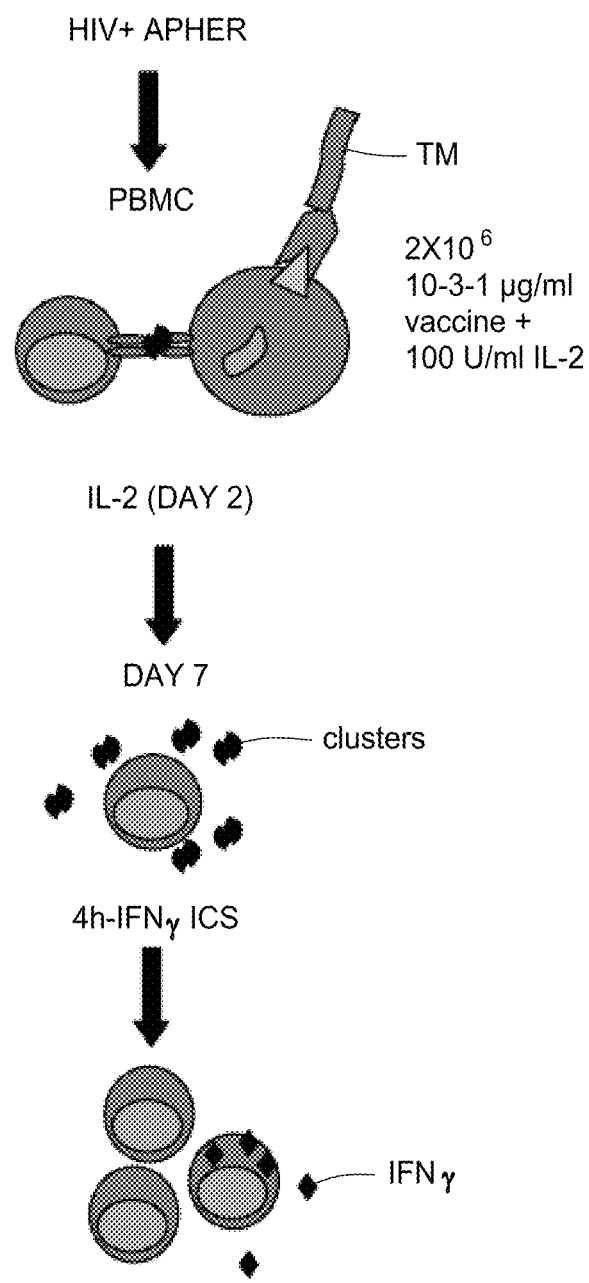
FIG. 11 depicts the protocol used to assay in vitro the potency of anti-DC receptor-antigen Targeting Molecules (TM) to elicit the expansion of antigen-specific T cells in the context of a PBMC culture.

FIG. 11 depicts the protocol used to assay in vitro the potency of anti-DC receptor-antigen targeting molecules [TM] to elicit the expansion of antigen-specific T cells in the context of a PBMC culture. Briefly, 2E6 PBMC from apheresis of HIV patients are incubated with a dose range of the targeting vaccine and 100 U/ml IL-2. Media is changed every two days. On day 7 clusters of peptides corresponding to the antigen are added to induce IFNγ production by T cells with TCR specificities for peptide sequences within each cluster. After 4 hours incubation with the peptide cluster and an agent that blocks cytokine secretion, cells are stained with anti-CD4, anti-CD8, anti-IL-13, and anti-IFNγ reagents and analyzed by FACS.

Figure 12:
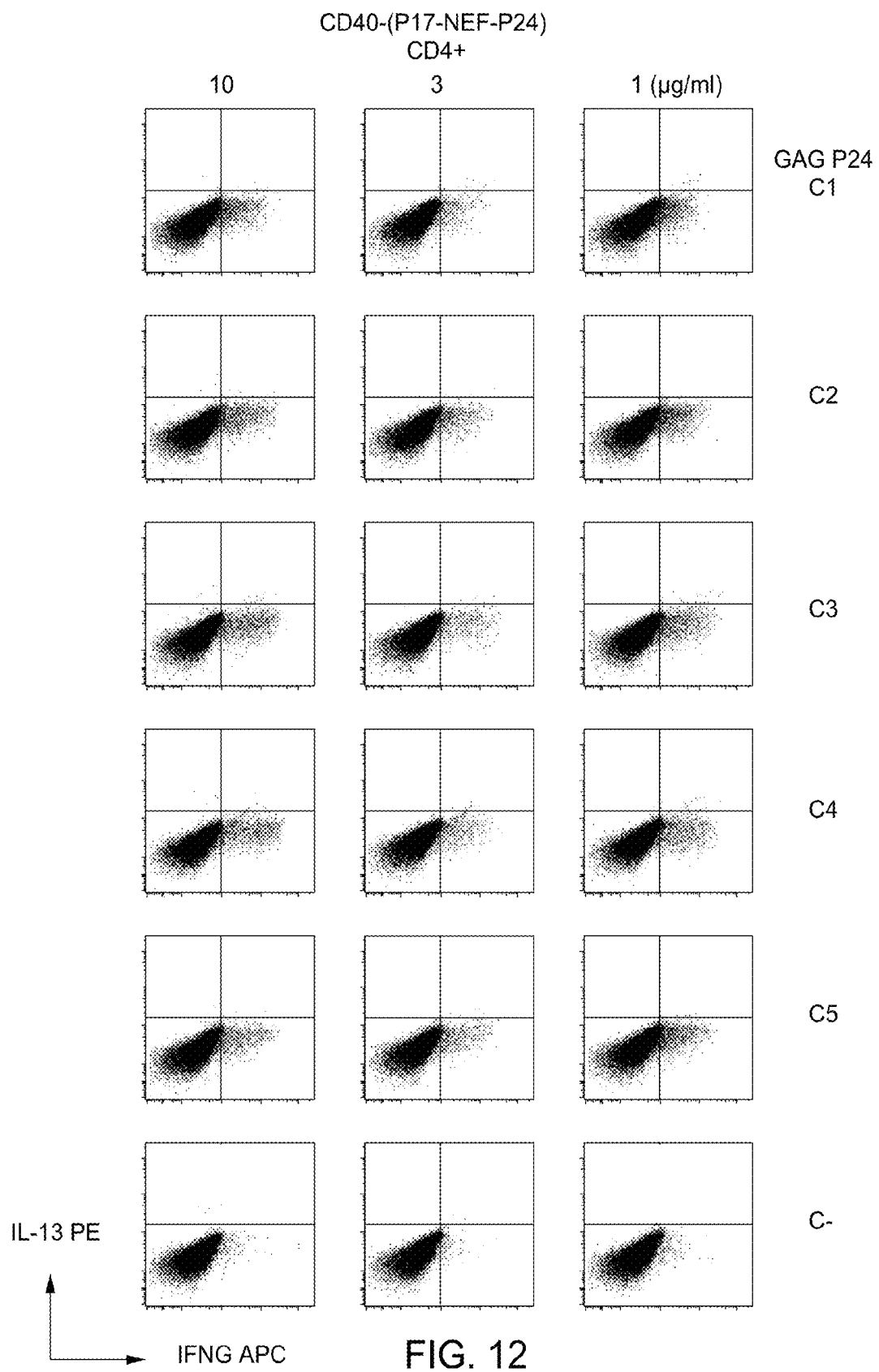
FIG. 12 shows the effects of targeting DC [within the PBMC] with an anti-CD4012E12 gag p17 nef gag p24 vaccine.
Figure 13:
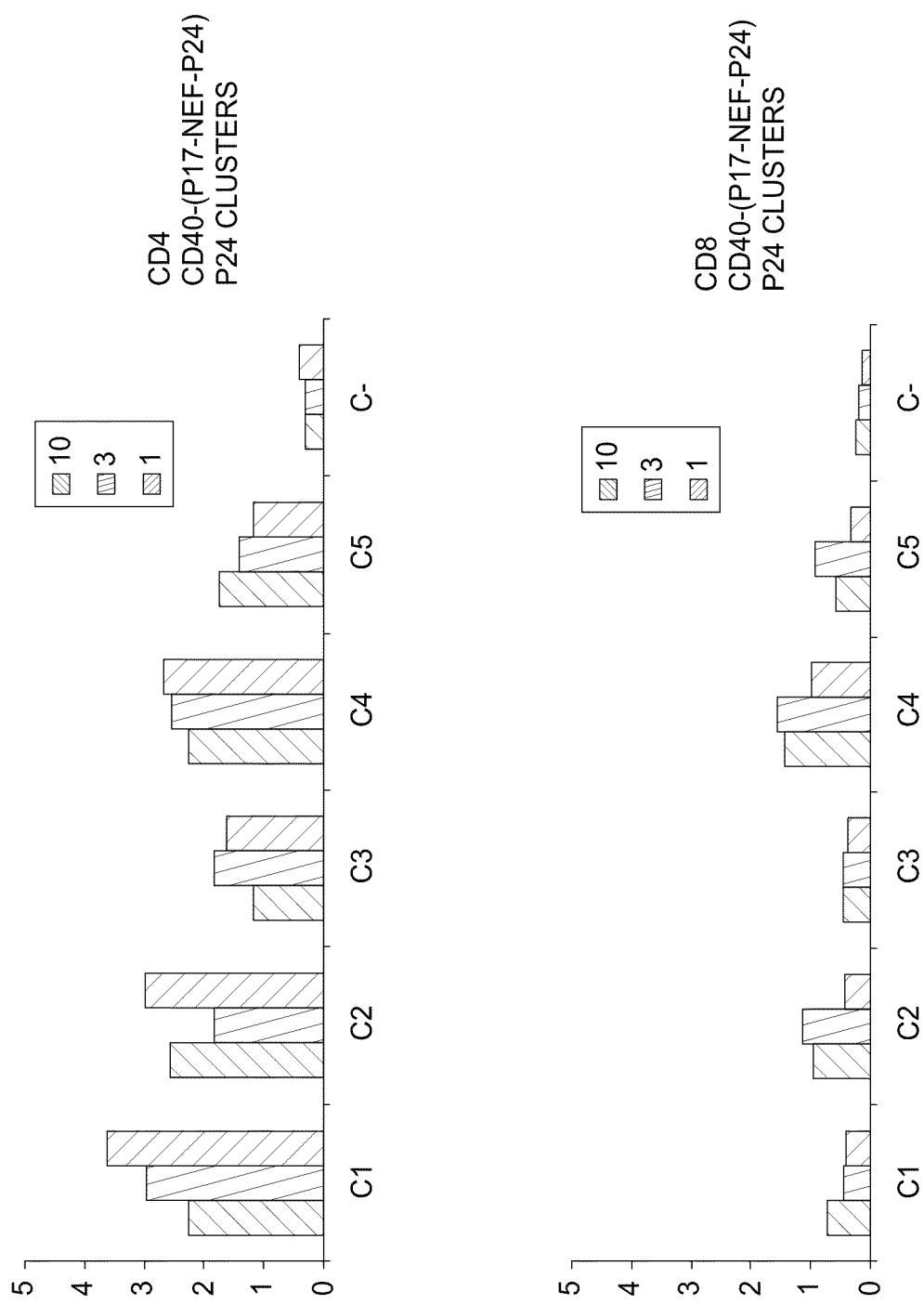
FIG. 13 shows that the vaccine elicits the expansion of CD4+ T cells with specificities to all the gag p24 peptide clusters.

FIGS. 12 and 13 show the effects of targeting DC [within the PBMC] with an anti-CD4012E12 gag p17 nef gag p24 vaccine—the H chain composition is shown below: C818 rAB-cetHS-puro [manti-CD40__12E12.3F3_H-LV-hIgG4H-C-Flex-v1-Viralgag-p17-f3-nef-f4-p24-6×His] joining residues are underlined, flexible linker residues are in bold, and antigen residues are italicized]:

(SEQ ID NO.: 31)
EVKLVESGGGLVQPGGSLKLSCATSGFTFSDYYMYWVRQTPEKRLEWVAY

INSGGGSTYYPDTVKGRFTISRDNAKNTLYLQMSRLKSEDTAMYYCARRG

LPFHAMDYWGQGTSVTVSSAKTKGPSVFPLAPCSRSTSESTAALGCLVKD

YFPEPVTVSWNSGALTSGVHTFPAVLQSSGLYSLSSVVTVPSSSLGTKTY

TCNVDHKPSNTKVDKRVESKYGPPCPPCPAPEFEGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSLGK<u>ASQT</u>

PTNTISVTPTNNSTPTNNSNPKPNP<u>ASLE</u>*MGARASILSGGELDRWEKIRL*

*RPGGKKKYKLKHIVWASRELERFAVNPGLLETSEGCRQILGQLQPSLQTG*

*SEELRSLYNTVATLYCVHQRIEIKDTKEALDKIEEEQNKS*<u>VD</u>TVTPTATA

TPSAIVTTITPTATTKP<u>VD</u>*MGGKWSKRSVVGWPTVRERMRRAEPAADGVG*

*AVSRDLEKHGAITSSNTAANNADCAWLEAQEEEEVGFPVRPQVPLRPMTY*

*KGALDLSHFLKEKGGLEGLIYSQKRQDILDLWVYHTQGYFPDWQNYTPGP*

*GIRYPLTFGWCFKLVPVEPEKVEEANEGENNSLLHPMSLHGMDDPEREVL*

*VWKFDSRLAFHHMARELHPEYYKDC*<u>EF</u>TNGSITVAATAPTVTPTVNATPS

AA<u>QF</u>*AQQAAADTGHSNQVSQNYPIVQNIQGQMVHQAISPRTLNAWVKVVE*

*EKAESREVIPMESALSEGATPQDLNTMLNTVGGHQAAMQMLKETINEFAA*

*EWDRVHPVHAGPIAPGQMREPRGSDIAGTTSTLQEQIGWMTHNPPIPVGE*

*IYKRWIILGLNKIVRMYSPTSILDIRQGPKEPERDYVDREYKTLRAEQAS*

*QEVKNWMTETLLVQNANPDCKTILKALGPGATLEEMMTACQGVG*HHHHHH

FIG. 12 shows that the vaccine elicits the expansion of CD4+ T cells with specificities to all the gag p24 peptide clusters—even at the lowest vaccine does tested the percentage of IFNγ-producing CD4+ T cells was significantly greater than when the cells were not treated with peptides. FIG. 13 [upper panel] shows this data in graph form—the vertical axis shows percent (%) IFNγ-producing cells. The lower panel shows similar data for CD8+ T cells within the PBMC culture, and this data also shows that all peptide clusters covering the gag p24 sequence elicited significantly greater production of IFNγ-producing T cells than the non-peptide control. Thus, the vaccine elicited a potent and responses against multiple epitopes within HIV gag p24.

Figure 14:
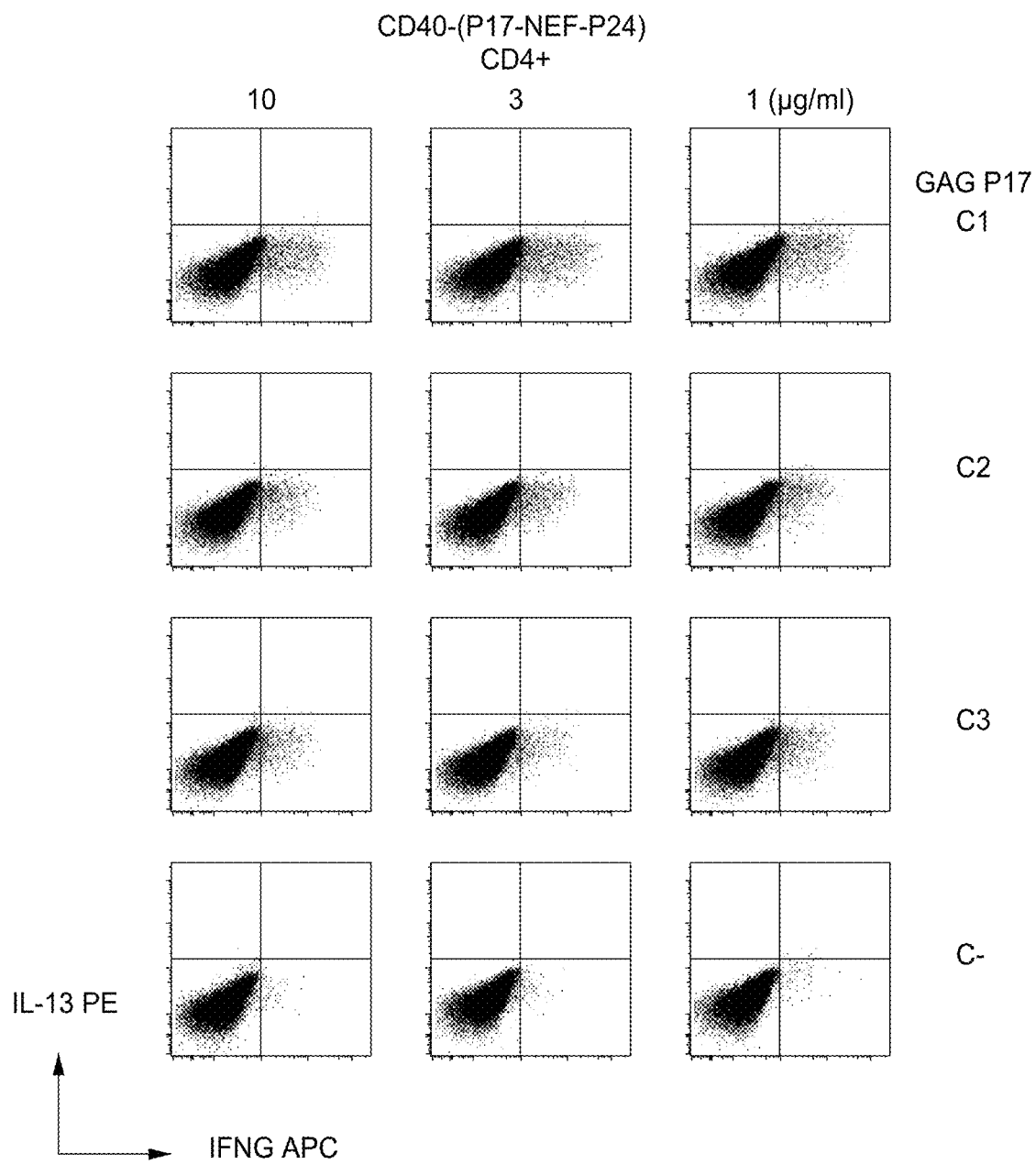
FIG. 14 are FACS data the vertical axis shows percentage IFNγ-producing cells [upper panel]. The lower panel shows similar data for CD8+ T cells within the PBMC culture, and this data also shows that all peptide clusters covering the gag p17 sequence elicited significantly greater production of IFNγ-producing T cells than the non-peptide control.
Figure 15:
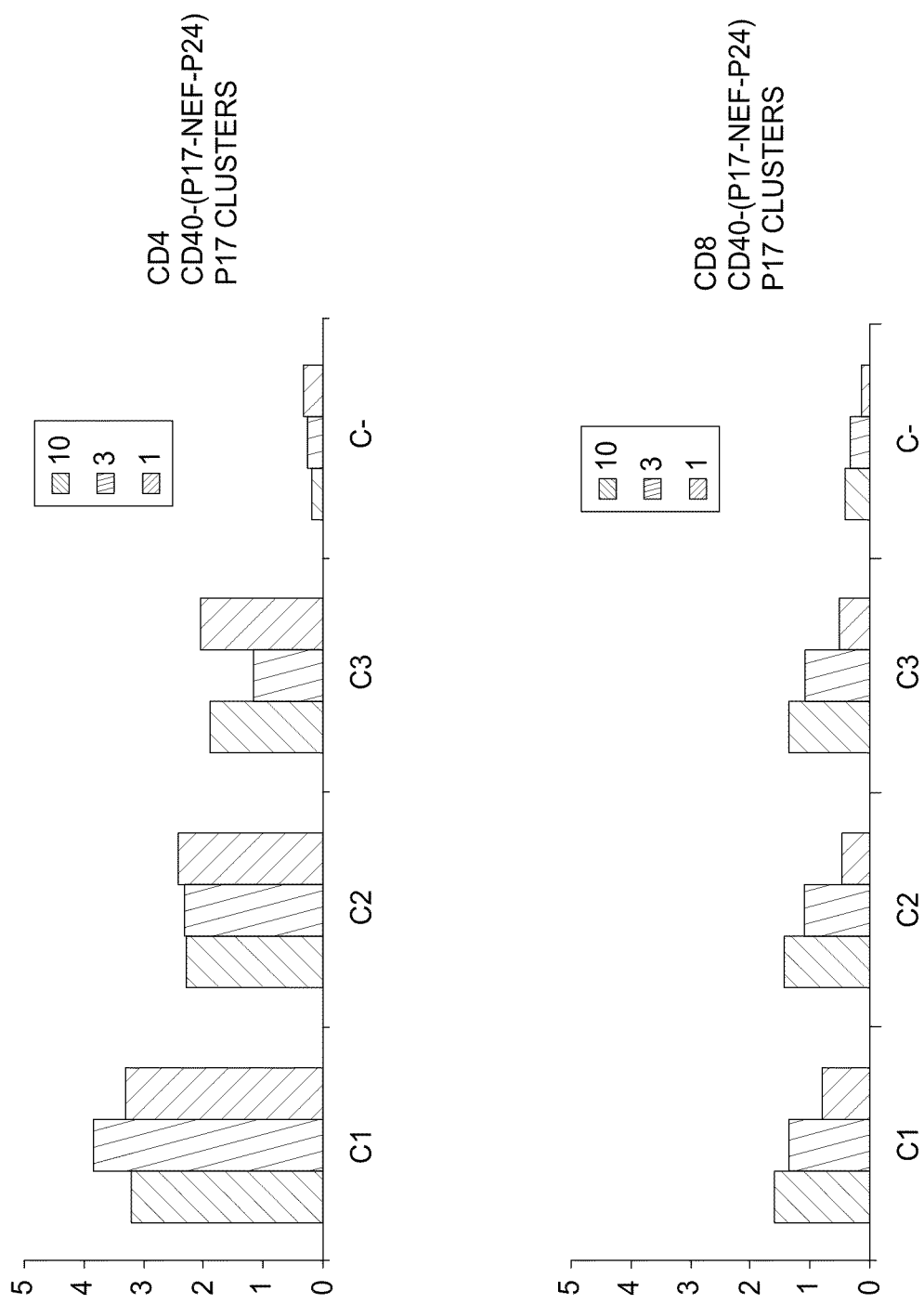
FIG. 15 shows that data in graph form that the vaccine elicits the expansion of CD4+ T cells with specificities to most of the HIV nef peptide clusters—even at the lowest vaccine does tested the percentage of IFNγ-producing CD4+ T cells was significantly greater than when the cells were not treated with peptides.

FIG. 14 shows that the vaccine elicits the expansion of CD4+ T cells with specificities to all the gag p17 peptide clusters—even at the lowest vaccine does tested the percentage of IFNγ-producing CD4+ T cells was significantly greater than when the cells were not treated with peptides. FIG. 15 shows this data in graph form—the vertical axis shows percentage IFNγ-producing cells [upper panel]. The lower panel shows similar data for CD8+ T cells within the PBMC culture, and this data also shows that all peptide clusters covering the gag p17 sequence elicited significantly greater production of IFNγ-producing T cells than the non-peptide control. Thus, the vaccine elicited a potent and responses against multiple epitopes within HIV gag p17.

Figure 16:
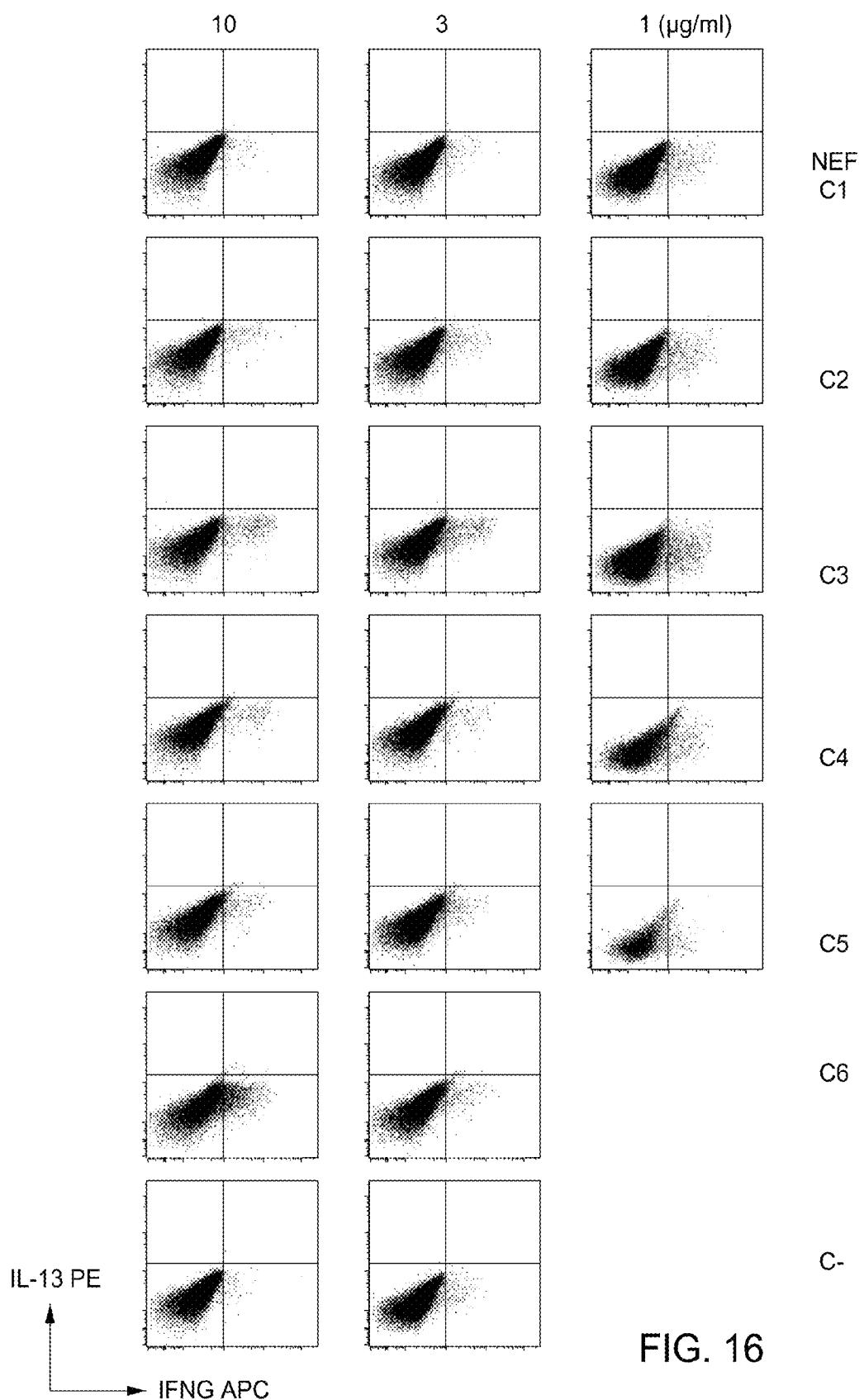
FIG. 16 are FACS data that show that the vaccine elicits the expansion of CD4+ T cells with specificities to most of the HIV nef peptide clusters even at the lowest vaccine does tested the percentage of IFNγ-producing CD4+ T cells was significantly greater than when the cells were not treated with peptides.
Figure 17:
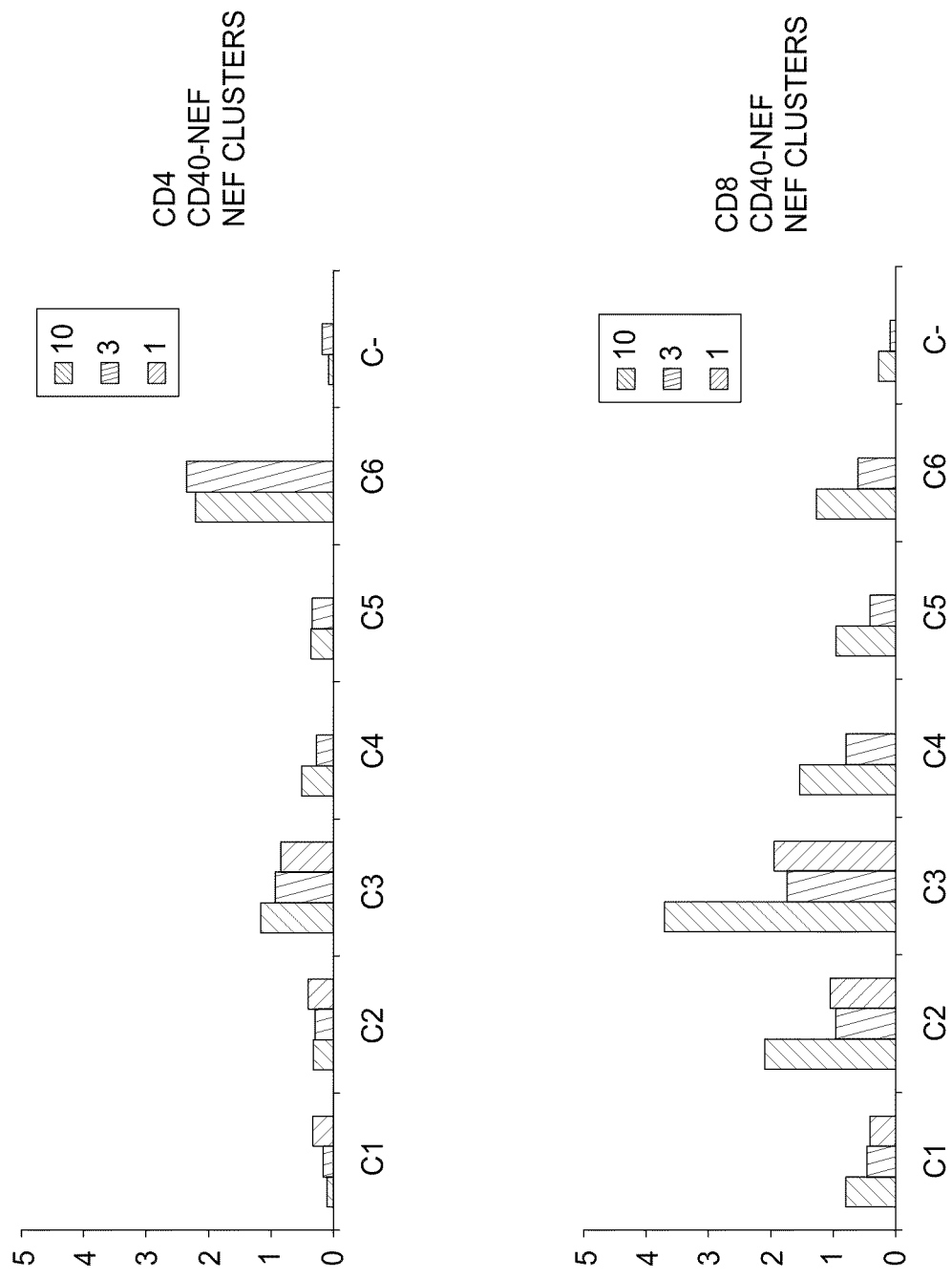
FIG. 17 shows the data in graph form—the vertical axis shows percentage IFNγ-producing cells [upper panel]. The lower panel shows similar data for CD8+ T cells within the PBMC culture, and this data also shows that all peptide clusters covering the nef sequence elicited significantly greater production of IFNγ-producing T cells than the non-peptide control.

FIG. 16 shows that the vaccine elicits the expansion of CD4+ T cells with specificities to most of the HIV nef peptide clusters—even at the lowest vaccine does tested the percentage of IFNγ-producing CD4+ T cells was significantly greater than when the cells were not treated with peptides. FIG. 17 shows this data in graph form—the vertical axis shows percentage IFNγ-producing cells [upper panel]. The lower panel shows similar data for CD8+ T cells within the PBMC culture, and this data also shows that all peptide clusters covering the nef sequence elicited significantly greater production of IFNγ-producing T cells than the non-peptide control. Thus the vaccine elicited a potent and response against multiple epitopes within HIV nef.

It was found that the data show the vaccine [anti-CD4012E12—linked to the specially engineered gag p17 nef gag p24 fusion protein] can, even at low doses, elicit broad immune responses—i.e., wide representation of epitopes in both the CD4+ and CD8+ T cell compartments. This data further demonstrate that each of the two vaccine parts [anti-CD4012E12 and other antibodies with similar special properties, and the gag-nef antigen engineered for maximal epitope representation consistent with efficient production]—i.e., the anti-CD40 component can be a vehicle for delivery of other antigens, and the antigen component can be delivered by other anti-DC receptor vehicles. The results also demonstrate the ability of the CD40-based targeting to expand a wide array of antigen-specific CD4+ and CD8+ T cells from both memory [HIV patients given HIV vaccine] and naïve [normal donors given PSA antigen] T cell populations.

Figure 18:
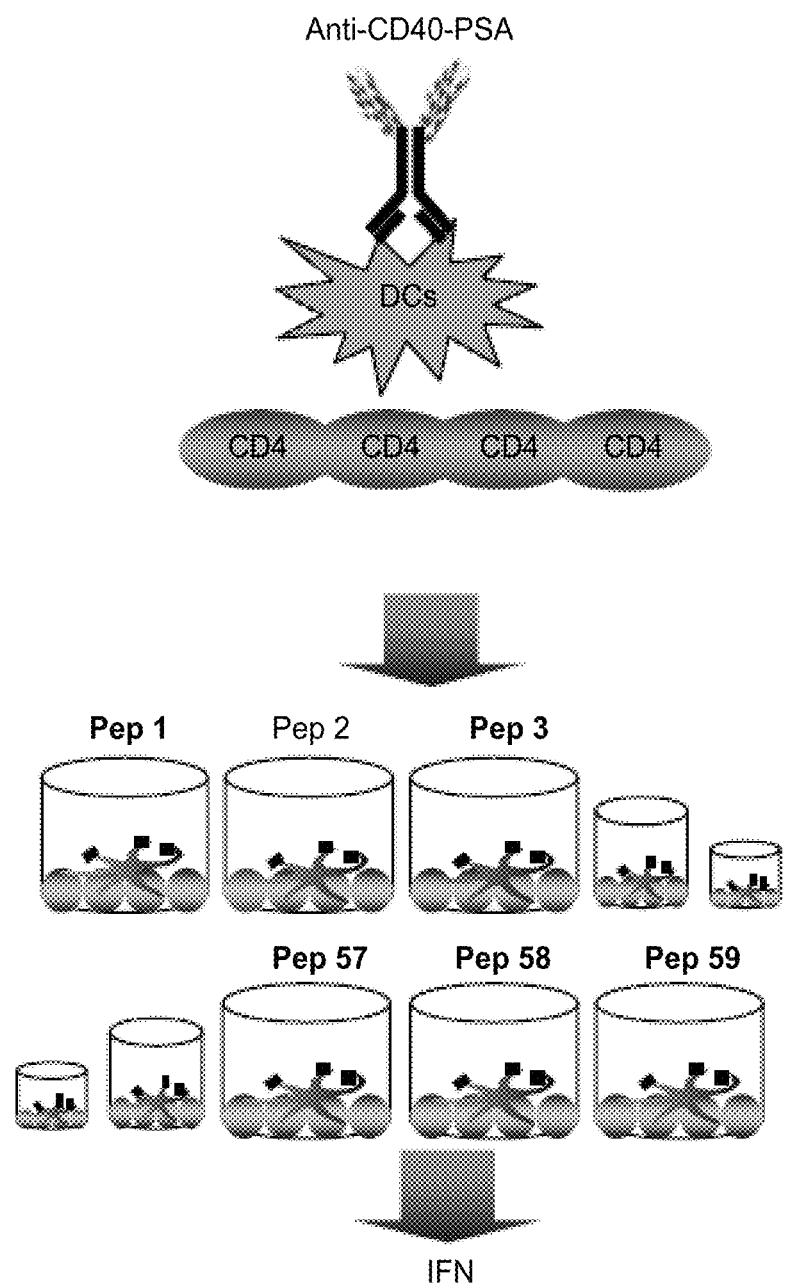
FIG. 18 shows the outline of a protocol to test the ability a vaccine composed of anti-CD40-12E12 linked to PSA [prostate-specific antigen] to elicit the expansion from a naïve T cell population PSA-specific CD4+ T cells corresponding to a broad array of PSA epitopes.

DCs targeted with anti-CD40-PSA induce PSA-specific CD4+ T cell responses. FIG. 18 shows the outline of a protocol to test the ability a vaccine composed of anti-CD40-12E12 linked to PSA [prostate-specific antigen] to elicit the expansion from a naïve T cell population PSA-specific CD4+ T cells corresponding to a broad array of PSA epitopes. Briefly, DCs derived by culture with IFNα and GM-CSF of monocytes from a normal donor are incubated with the vaccine. The next day, cells are placed in fresh medium and pure CD4+ T cells from the same donor are added. Several days later, PSA peptides are added and, after four hours, secreted IFNγ levels in the culture supernatants are determined.

Figure 19:
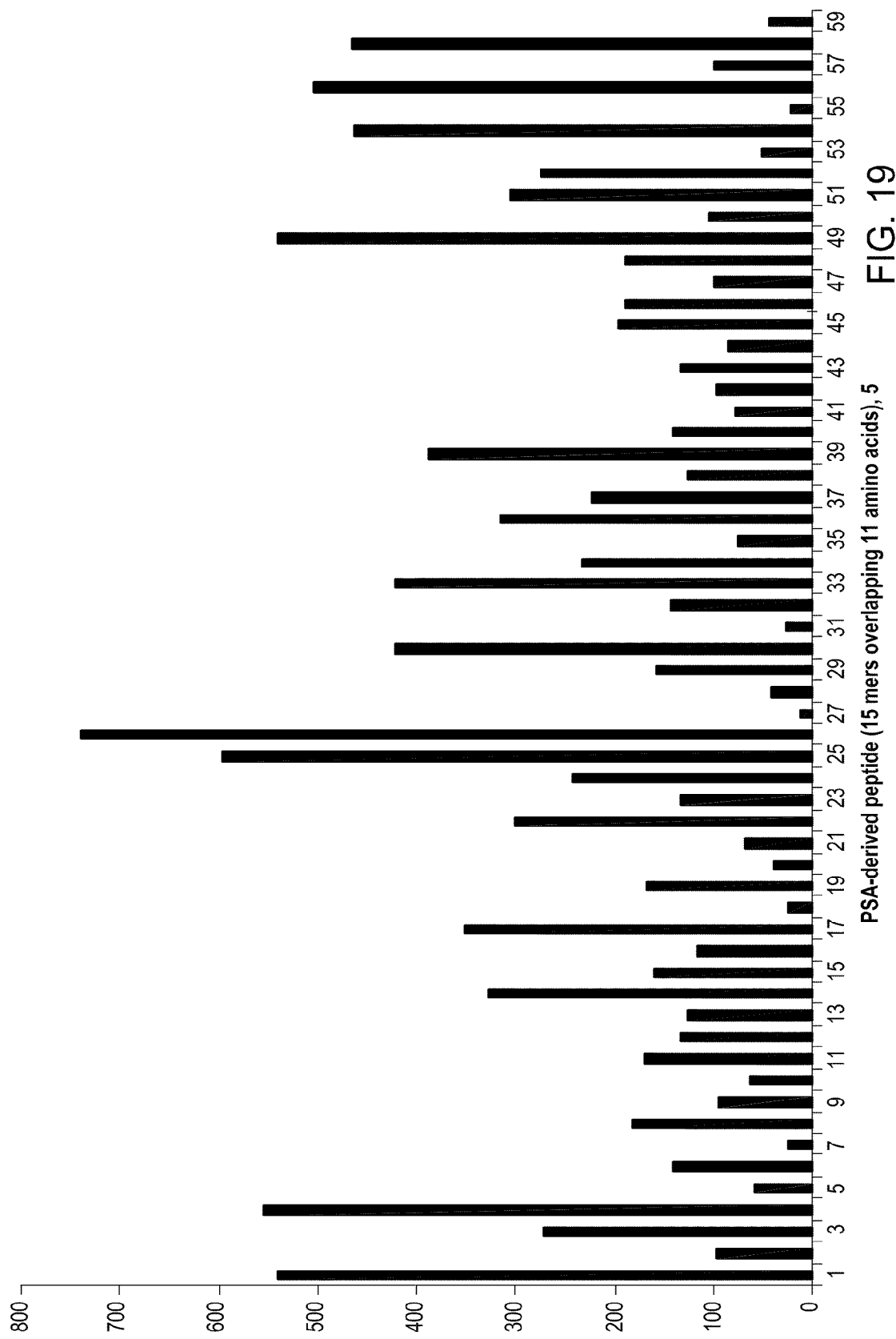
FIG. 19 shows that many PSA peptides elicit potent IFNγ-production responses indicating that anti-CD4012E12 and similar antiCD40 agents can effectively deliver antigen to DC, resulting in the priming of immune responses against multiple epitopes of the antigen.

FIG. 19 shows that many PSA peptides elicit potent IFNγ-production responses indicating that anti-CD4012E12 and similar antiCD40 agents can effectively deliver antigen to DC, resulting in the priming of immune responses against multiple epitopes of the antigen.

FIG. 20 shows that DCs targeted with anti-CD40-PSA targeted to DCs induce PSA-specific CD8+ T cell responses. IFNDCs were targeted with 1 µg mAb fusion protein with PSA. Purified autologous CD8+ T cells were co-cultured for 10 days. Cells were stained with anti-CD8 and PSA (KLQCVDLHV)-tetramer. Cells are from a HLA-A*0201 positive healthy donor. The results demonstrate that anti-CD40 effectively delivers PSA to the DC, which in turn elicit the expansion of PSA-specific CD8+ T cells.

FIG. 21 outlines the DC targeting protocol for testing anti-DC receptor targeting vaccines for their ability to direct the expansion of antigen-specific T cells resulting from targeted uptake by the DC and presentation of antigen epitopes on their cell surface. Briefly, HIV patient monocytes are differentiated into DC by culture for 3 days in IFNα and GM-CSF. Vaccine [FP] is then added at 10 ug/ml along with autologous T cells. After 10 days in culture, antigen peptide clusters are added to the expanded T cells and after 4 hours intracellular IFNα is measured.

FIG. 22 [upper panel] shows comparison of the efficacy of anti-CD4012E12 nef, anti-CD4012E12 gag p24, and anti-CD4012E12 gag p17 nef gag p24 vaccines [patient Aph002]. Anti-CD4012E12 nef vaccine [green bars] stimulated the expansion of IFNα-producing CD4+ T cells responsive only to nef peptide epitopes, anti-CD4012E12 gag p24 [blue bars] stimulated the expansion of IFNα-producing CD4+ T cells responsive to only p24 peptide epitopes, while the anti-CD4012E12 gag p17 nef gag p24 stimulated the expansion of IFNα-producing CD8+ T cells responsive to gag p17, nef, and p24 peptide epitopes.

FIG. 22 [lower panel] shows comparison of the efficacy of anti-CD4012E12 nef, anti-CD4012E12 gag p24, and anti-CD4012E12 gag p17 nef gag p24 vaccines [patient Aph002]. Anti-CD4012E12 nef vaccine [green bars] stimulated the expansion of IFNα-producing CD8+ T cells responsive only to nef peptide epitopes, while anti-CD4012E12 gag p17 nef gag p24 [orange bars] stimulated the expansion of IFNα-producing CD8+ T cells responsive to both gag p17 and nef peptide epitopes.

FIG. 23 [upper panel] shows comparison of the efficacy of anti-CD4012E12 nef, anti-CD4012E12 gag p24, and anti-CD4012E12 gag p17 nef gag p24 vaccines [patient Aph010]. Anti-CD4012E12 nef vaccine [green bars] stimulated the expansion of IFNα-producing CD4+ T cells responsive only to nef peptide epitopes, anti-CD4012E12 gag p24 [blue bars] stimulated the expansion of IFNα-producing CD4+ T cells responsive to only p24 peptide epitopes, while the anti-CD4012E12 gag p17 nef gag p24 stimulated the expansion of IFNα-producing CD8+ T cells responsive to gag p17, nef, and p24 peptide epitopes.

FIG. 23 [lower panel] shows comparison of the efficacy of anti-CD4012E12 nef, anti-CD4012E12 gag p24, and anti-CD4012E12 gag p17 nef gag p24 vaccines [patient Aph002]. Anti-CD4012E12 nef vaccine [green bars] stimulated the expansion of IFNα-producing CD8+ T cells responsive only to nef peptide epitopes, anti-CD4012E12 gag p24 [blue bars] stimulated the expansion of IFNα-producing CD8+ T cells responsive to only p24 peptide epitopes, while anti-CD4012E12 gag p17 nef gag p24 [orange bars] stimulated the expansion of IFNα-producing CD8+ T cells responsive to both gag p17 and nef peptide epitopes.

These data demonstrate that the anti-CD4012E12 gag p17 nef gag p24 vaccine can elicit a broad array of T cell responses covering multiple epitopes within all three antigen elements of the vaccine—HIV gag p17, HIV gag p24, and HIV nef.

The sequence below is the amino acid sequence of the Cohesin [bold residues]—Cyclin D1 [underlined residues] fusion protein expressed by the C515 vector.

C515 *E. coli*-pET28 [Cohesin-hCyclinD1-6×His]

(SEQ ID NO.: 32)
MDLDAVRIKDTVNAKPGDTVNIPVRFSGIPSKGIANCDFVYSYDPNVLEI

IEIKPGELIVDPNPTICSFDTAVYPDRKMIVFLFAEDSGTGAYAITKDGV

FATIVAKVKEGAPNGLSVIKFVEVGGFANNDLVEQKTQFFDGGVNVGDTT

EPATPTTPVTTPTTTDDLDAASLEMEHQLLCCEVETIRRAYPDANLLNDR

VLRAMLKAEETCAPSVSYFKCVQKEVLPSMRKIVATWMLEVCEEQKCEEE

VFPLAMNYLDRFLSLEPVKKSRLQLLGATCMFVASKMKETIPLTAEKLCI

YTDNSIRPEELLQMELLLVNKLKWNLAAMTPHDFIEHFLSKMPEAEENKQ

IIRKHAQTFVALCATDVKFISNPPSMVAAGSVVAAVQGLNLRSPNNFLSY

YRLTRFLSRVIKCDPDCLRACQEQIEALLESSLRQAQQNMDPKAAEEEEE

EEEEVDLACTPTDVRDVDIHHHHHH

Expression and purification of Coh.Cyclin D1 protein produced in *E. coli*.

Coh.Cyclin D1 was expressed in *E. coli* strain T7 Express (NEB) grown in Luria broth (Difco) at 37° C. with selection for kanamycin resistance (40 µg/ml) and shaking at 200 rounds/min to mid-log growth phase. Then 120 mg/L IPTG (Bioline) was added and after a further 3 hrs, the cells were harvested by centrifugation and stored at −80° C. *E. coli* cells from each 1 L fermentation were resuspended in 50 ml ice-cold 50 mM Tris, 1 mM EDTA pH 8.0 with 0.2 ml of protease inhibitor Cocktail II (Calbiochem). The cells were sonicated twice on ice for 4 min at setting 18 (Fisher Sonic Dismembrator 60) with a 5 min rest period and then spun at 17,000 r.p.m. (Sorvall SA-600) for 20 min at 4° C. The 50 ml cell lysate supernatant was passed through 10 ml of ANX Sepharose beads (GE Healthcare), then the flow-through was adjusted to binding buffer with 7.5 ml 160 mM Tris, 40 mM imidazole, 4 M NaCl pH 7.9 and loaded onto a 5 ml HiTrap chelating HP column (GE Healthcare) charged with Ni++. The bound protein was washed with 20 mM NaPO$_4$, 300 mM NaCl, 10 mM imidazole pH 7.6 (buffer A) and eluted with a 10-500 mM imidazole gradient in buffer A. The peak fractions were analyzed by SDS-PAGE gel, pooled. Approximately 15 milligrams of the pooled eluted Cohesin-Cyclin D1 fusion protein was reacted overnight at room temperature with 10 milligrams of mPEG-MAL 20k reagent (Nektar), which attaches a 20 kDa pegyl group to free cysteine residues [of which there are several within the Cyclin D1 domain]. A part of this reaction was dialyzed versus DPBS [Gibco] and part was adjusted to pH 7.5, then DTT was added to 10 mM for 1.5 hours at room temperature to reduce any disulphide bonds, followed by addition of 25 mM iodoacetamide for 1.5 hours at room temperature to alkylate the free cysteine residues, followed by addition of 20 mM DTT for 1.5 hours at room temperature, followed by dialysis versus DPBS. The pegylation was required to ensure the protein remained soluble in DPBS and the alkylation [which was not necessary for the activity of the protein in the context of in vitro anti-CD40 targeting] served to ensure that the product was free of intermolecular disulphide cross-linked forms.

FIG. 24. Analysis of the interaction of Cohesin-Cyclin D1 fusion protein with anti-DC receptor-Dockerin recombinant antibody. Antibody-Dockerin or antibody-HIV nef fusion protein [20 µg] was incubated with 100 µl protein A-Sepharose beads [GE Biosciences] then washed twice with DPBS. Pegylated [peg] or pegylated and alkylated [peg alk] Cohesin-Cyclin D1 [Coh.Cyclin D1] were added [20 µg] and, after 30 minutes at room temperature, the supernatant was separated from the beads by centrifugation. The beads were eluted with 20 mM HCl and the eluate and supernatant were dried, resuspended in SDS.PAGE loading buffer and run on reducing SDS.PAGE and visualized by Coomasssie Blue staining Lane 1 shows the supernatant from beads loaded with antibody-Dockerin+peg Coh.Cyclin D1 and Lane 2 is the corresponding bead eluate. Lane 3 shows the supernatant from beads loaded with antibody-HIV nef+peg Coh.Cyclin D1 and Lane 4 is the corresponding bead eluate. Lane 5 shows the supernatant from beads loaded with antibody-Dockerin+peg alk Coh.Cyclin D1 and Lane 6 is the corresponding bead eluate. Lane 7 shows the supernatant from beads loaded with antibody-HIV nef+peg alk Coh.Cyclin D1 and Lane 8 is the corresponding bead eluate. Lane 9 shows antibody-Dockerin alone, lane 10 shows antibody-HIV nef alone, Lane 11 shows peg Coh.Cyclin D1 alone, and Lane 12 shows peg alk Coh.Cyclin D1 alone. The arrows [top to bottom] show: 1) high molecular weight pegylated forms of Coh.Cyclin D1, 2) the position of antibody heavy chain, 3) the position of non-pegylated Coh.Cyclin D1 [which is about 50% of the preparations], 4) the position of the antibody light chain.

The above analysis shows that antibody-Dockerin, but not antibody-HIV nef, effectively captures most of the Coh.Cyclin D1. This demonstrates that the Coh.Cyclin D1 preparations can assemble a complex with anti-DC receptor-Dockerin targeting vehicles.

Mantle Cell Lymphoma (MCL) is a B-cell non-Hodgkin's lymphoma which represents 5-10% of all non-Hodgkin's lymphoma, predominantly in males with advanced age. It is a very aggressive cancer with the worst prognosis after conventional treatment, frequent relapses, and relatively short survival. It has a genetic hallmark: t (11;14) (q13; q32) translocation—leading to the over expression of Cyclin D1.

G1/S-specific cyclin-D1—alternatively named PRAD1, Bcl-1 functions in cell cycle control of G1 progression and G1/S transition via forming complexes with CDK4 and 6. There is no normal expression in mature lymphocytes since expression is cell cycle dependent with maximal expression in G1, minimal in S. Thus, raising cytotoxic T cell responses specifically directed to cells over expressing Cyclin D1 is an attractive MCL vaccination strategy.

FIG. 25 shows a schema of overlapping peptides from Cyclin D1. These are added to T cell cultures, either as individual peptides or as pools of peptides, where they can be presented on MHC and thereby stimulate proliferation of peptide specific T cells.

FIG. 26 shows a schema [left panel] of the study design for testing the ability of anti-CD40-Cyclin D1 complexes to elicit expansion in vitro of Cyclin D1-specific CD4+ T cells. After incubation of DCs with the targeting complex, autologous CD4+ T cells [i.e., from the same donor] labeled with the dye CFSC are added and culture continues for an additional 8 days with IL-2, then 2 days rest without IL-2. Next, the culture is divided and stimulated with individual Cyclin D peptides, or no peptide, for 8 hours followed by staining for intracellular IFNg and IL-2 [indicators of T cell activation] and analysis by FACS.

The analysis shows that Cyclin D peptides P8, P16, and P54 stimulate significantly greater production of proliferating [i.e., marked by CFSC dilution] CD4+ T cells than cells incubated without peptide [or other Cyclin D1 peptides [not shown]. Thus, the anti-CD40-Cyclin D1 complex functions to elicit the expansion from T cells of a normal donor of Cyclin D1-specific T cells with effector function phenotype.

FIG. 27 shows a study and analysis similar to that detailed in FIG. 26, except that a different normal donor was used—in this case the anti-CD40-Cyclin D1 complex elicited the expansion of IFNg positive proliferating CD4+ T cells specific for Cyclin D1 peptides P4, P43, and P70.

FIG. 28 shows a schema and analysis similar to those described above in FIG. 26, except that CD8+ T cells were used. In this donor, anti-CD40-Cyclin D1 complex elicited the expansion of Cyclin D1-specific CD8+ T cells, in particular those with specificities corresponding to peptides contained within pool I and pool II.

FIG. 29 shows similar data from the same donor, but analyzed with individual peptides from these pools. In particular, these T cells show specificity for peptides P7, P8, and P10.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A composition comprising:
    a dendritic cell (DC)-specific antibody or fragment thereof comprising a light chain sequence selected from the group consisting of SEQ ID NO: 24, 25, 26, 27 and 28 and a heavy chain sequence selected from the group consisting of SEQ ID NO: 29 and 30, to which one or more engineered Gag antigens are attached to form an antibody-antigen fusion protein wherein the engineered Gag antigens are less susceptible to proteolytic degradation by eliminating one or more proteolytic sites; and
    a Nef antigen that is attached to the engineered Gag antigen wherein the composition is able to elicit a human immunodeficiency virus (HIV)-specific T cell immune response to Gag and Nef.

2. The composition of claim 1, wherein the Gag and Nef antigens comprise a fusion protein separated by one or more flexible linkers.

3. The composition of claim 1, wherein the protein comprises SEQ ID NO: 31.

4. The composition of claim 1, wherein the Gag and Nef antigens comprise a fusion protein separated by one or more flexible linkers.

5. The composition of claim 4, wherein the protein comprises SEQ ID NO: 31.

* * * * *